United States Patent
Byrne et al.

(10) Patent No.: US 10,781,459 B2
(45) Date of Patent: Sep. 22, 2020

(54) METHODS OF PACKAGING MULTIPLE ADENO-ASSOCIATED VIRUS VECTORS

(71) Applicant: University of Florida Research Foundation, Inc., Gainesville, FL (US)

(72) Inventors: Barry John Byrne, Gainesville, FL (US); Phillip A. Doerfler, Cordova, TN (US); Nathalie Clement, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 205 days.

(21) Appl. No.: 15/320,707

(22) PCT Filed: Jun. 20, 2015

(86) PCT No.: PCT/US2015/036841
§ 371 (c)(1),
(2) Date: Dec. 20, 2016

(87) PCT Pub. No.: WO2015/196179
PCT Pub. Date: Dec. 23, 2015

(65) Prior Publication Data
US 2017/0218395 A1 Aug. 3, 2017

Related U.S. Application Data

(60) Provisional application No. 62/015,031, filed on Jun. 20, 2014.

(51) Int. Cl.
C12N 7/02 (2006.01)
C12N 15/86 (2006.01)
C12N 7/00 (2006.01)
C12Q 1/70 (2006.01)

(52) U.S. Cl.
CPC ............ C12N 15/86 (2013.01); C12N 7/00 (2013.01); C12Q 1/701 (2013.01); *C12N 2750/14143* (2013.01); *C12N 2750/14152* (2013.01); *C12Q 2600/158* (2013.01)

(58) Field of Classification Search
None
See application file for complete search history.

(56) References Cited

U.S. PATENT DOCUMENTS

2004/0121444 A1* 6/2004 Zolotukhin ............ C12N 15/86
   435/239
2014/0087444 A1   3/2014 Bennett et al.
2014/0336245 A1* 11/2014 Mingozzi ............... C12N 9/644
   514/44 R

OTHER PUBLICATIONS

Clement et al., "Large-Scale Adeno-Associated Viral Vector Production Using a Herpesvirus-Based System Enables Manufacturing for Clinical Studies," Human Gene Therapy 20: 796-806 (Year: 2009).*

(Continued)

*Primary Examiner* — M Franco G Salvoza
(74) *Attorney, Agent, or Firm* — Wolf, Greenfield & Sacks, P.C.

(57) ABSTRACT

Provided herein are methods related to co-packaging of multiple rAAV particles, e.g., by introducing multiple nucleic acid vectors encoding proteins or polypeptides or RNAs of interest into a single cell preparation.

19 Claims, 4 Drawing Sheets

Specification includes a Sequence Listing.

(56) References Cited

OTHER PUBLICATIONS

Sharma et al., "Transduction efficiency of AAV 2/6, 2/8 and 2/9 vectors for delivering genes in human corneal fibroblasts," Brain Res Bull 81(2-3): 273 (Year: 2010).*
Shin et al., "Recombinant Adeno-Associated Viral Vector Production and Purification," Methods Mol Biol 798: 267-284 (Year: 2012).*
Zeltner et al., "Near-perfect infectivity of wild-type AAV as benchmark for infectivity of recombinant AAV vectors," Gene Ther 17(7): 872-879 (Year: 2010).*
International Search Report and Written Opinion dated Sep. 30, 2015 for Application No. PCT/US2015/036841.
International Preliminary Report on Patentability dated Dec. 29, 2016 for Application No. PCT/US2015/036841.

* cited by examiner

SEQUENCE LISTING

```
<160> NUMBER OF SEQ ID NOS: 17

<210> SEQ ID NO 1
<211> LENGTH: 3161
<212> TYPE: DNA
<213> ORGANISM: Artificial Sequence
<220> FEATURE:
<223> OTHER INFORMATION: Synthetic Polynucleotide

<400> SEQUENCE: 1
aggaacccct agtgatggag ttggccactc cctctctgcg cgctcgctcg ctcactgagg     60
ccgcccgggc aaagcccggg cgtcgggcga cctttggtcg cccggcctca gtgagcgagc    120
gagcgcgcag agagggagtg gccaaccccc cccccccccc ccctgcagcc ctgcattaat    180
gaatcggcca acgcgcgggg agaggcggtt tgcgtattgg gcgctcttcc gcttcctcgc    240
tcactgactc gctgcgctcg gtcgttcggc tgcggcgagc ggtatcagct cactcaaagg    300
cggtaatacg gttatccaca gaatcagggg ataacgcagg aaagaacatg tgagcaaaag    360
gccagcaaaa ggccaggaac cgtaaaaagg ccgcgttgct ggcgtttttc cataggctcc    420
gcccccctga cgagcatcac aaaaatcgac gctcaagtca gaggtggcga aacccgacag    480
gactataaag ataccaggcg tttccccctg gaagctccct cgtgcgctct cctgttccga    540
ccctgccgct taccggatac ctgtccgcct ttctcccttc gggaagcgtg gcgctttctc    600
aatgctcacg ctgtaggtat ctcagttcgg tgtaggtcgt tcgctccaag ctgggctgtg    660
tgcacgaacc ccccgttcag cccgaccgct gcgccttatc cggtaactat cgtcttgagt    720
ccaacccggt aagacacgac ttatcgccac tggcagcagc cactggtaac aggattagca    780
gagcgaggta tgtaggcggt gctacagagt tcttgaagtg gtggcctaac tacggctaca    840
ctagaaggac agtatttggt atctgcgctc tgctgaagcc agttaccttc ggaaaaagag    900
ttggtagctc ttgatccggc aaacaaacca ccgctggtag cggtggtttt tttgtttgca    960
agcagcagat tacgcgcaga aaaaaaggat ctcaagaaga tcctttgatc ttttctacgg   1020
ggtctgacgc tcagtggaac gaaaactcac gttaagggat tttggtcatg agattatcaa   1080
aaaggatctt cacctagatc cttttaaatt aaaaatgaag ttttaaatca atctaaagta   1140
tatatgagta aacttggtct gacagttacc aatgcttaat cagtgaggca cctatctcag   1200
cgatctgtct atttcgttca tccatagttg cctgactccc cgtcgtgtag ataactacga   1260
tacgggaggg cttaccatct ggccccagtg ctgcaatgat accgcgagac ccacgctcac   1320
cggctccaga tttatcagca ataaaccagc cagccggaag ggccgagcgc agaagtggtc   1380
ctgcaacttt atccgcctcc atccagtcta ttaattgttg ccgggaagct agagtaagta   1440
gttcgccagt taatagtttg cgcaacgttg ttgccattgc tacaggcatc gtggtgtcac   1500
gctcgtcgtt tggtatggct tcattcagct ccggttccca acgatcaagg cgagttacat   1560
gatcccccat gttgtgcaaa aaagcggtta gctccttcgg tcctccgatc gttgtcagaa   1620
gtaagttggc cgcagtgtta tcactcatgg ttatggcagc actgcataat tctcttactg   1680
tcatgccatc cgtaagatgc ttttctgtga ctggtgagta ctcaaccaag tcattctgag   1740
aatagtgtat gcggcgaccg agttgctctt gcccggcgtc aatacgggat aataccgcgc   1800
```

| | |
|---|---:|
| cacatagcag aactttaaaa gtgctcatca ttggaaaacg ttcttcgggg cgaaaactct | 1860 |
| caaggatctt accgctgttg agatccagtt cgatgtaacc cactcgtgca cccaactgat | 1920 |
| cttcagcatc ttttactttc accagcgttt ctgggtgagc aaaaacagga aggcaaaatg | 1980 |
| ccgcaaaaaa gggaataagg gcgacacgga aatgttgaat actcatactc ttcctttttc | 2040 |
| aatattattg aagcatttat cagggttatt gtctcatgag cggatacata tttgaatgta | 2100 |
| tttagaaaaa taaacaaata ggggttccgc gcacatttcc ccgaaaagtg ccacctgacg | 2160 |
| tctaagaaac cattattatc atgacattaa cctataaaaa taggcgtatc acgaggccct | 2220 |
| ttcgtctcgc gcgtttcggt gatgacggtg aaaacctctg acacatgcag ctcccggaga | 2280 |
| cggtcacagc ttgtctgtaa gcggatgccg ggagcagaca agcccgtcag ggcgcgtcag | 2340 |
| cgggtgttgg cgggtgtcgg gctggctta actatgcggc atcagagcag attgtactga | 2400 |
| gagtgcacca tatgcggtgt gaaataccgc acagatgcgt aaggagaaaa taccgcatca | 2460 |
| ggaaattgta acgttaata tttgttaaa attcgcgtta aattttgtt aaatcagctc | 2520 |
| atttttaac caataggccg aaatcggcaa atcccttat aaatcaaaag aatagaccga | 2580 |
| gatagggttg agtgttgttc cagtttggaa caagagtcca ctattaaaga acgtggactc | 2640 |
| caacgtcaaa gggcgaaaaa ccgtctatca gggcgatggc ccactacgtg aaccatcacc | 2700 |
| ctaatcaagt tttttggggt cgaggtgccg taaagcacta atcggaacc ctaaagggag | 2760 |
| cccccgattt agagcttgac ggggaaagcc ggcgaacgtg gcgagaaagg aagggaagaa | 2820 |
| agcgaaagga gcgggcgcta gggcgctggc aagtgtagcg gtcacgctgc gcgtaaccac | 2880 |
| cacacccgcc gcgcttaatg cgccgctaca gggcgcgtcg cgccattcgc cattcaggct | 2940 |
| acgcaactgt tgggaagggc gatcggtgcg ggcctcttcg ctattacgcc aggctgcagg | 3000 |
| gggggggggg gggggttgg ccactccctc tctgcgcgct cgctcgctca ctgaggccgg | 3060 |
| gcgaccaaag gtcgcccgac gcccgggctt gcccgggcg gcctcagtga gcgagcgagc | 3120 |
| gcgcagagag ggagtggcca actccatcac tagggggttcc t | 3161 |

<210> SEQ ID NO 2
<211> LENGTH: 7200
<212> TYPE: DNA
<213> ORGANISM: Artificial Sequence
<220> FEATURE:
<223> OTHER INFORMATION: Synthetic Polynucleotide

<400> SEQUENCE: 2

| | |
|---|---:|
| gggggggggg ggggggggtt ggccactccc tctctgcgcg ctcgctcgct cactgaggcc | 60 |
| gggcgaccaa aggtcgcccg acgcccgggc tttgcccggg cggcctcagt gagcgagcga | 120 |
| gcgcgcagag agggagtggc caactccatc actaggggtt cctagatctg aattcggtac | 180 |
| cctagttatt aatagtaatc aattacgggg tcattagttc atagcccata tatggagttc | 240 |
| cgcgttacat aacttacggt aaatggcccg cctggctgac cgcccaacga cccccgccca | 300 |
| ttgacgtcaa taatgacgta tgttcccata gtaacgccaa tagggacttt ccattgacgt | 360 |
| caatgggtgg actatttacg gtaaactgcc cacttggcag tacatcaagt gtatcatatg | 420 |
| ccaagtacgc cccctattga cgtcaatgac ggtaaatggc ccgcctggca ttatgcccag | 480 |
| tacatgacct tatgggactt tcctacttgg cagtacatct acgtattagt catcgctatt | 540 |
| accatggtcg aggtgagccc cacgttctgc ttcactctcc ccatctcccc ccctccccca | 600 |
| cccccaattt tgtatttatt tatttttaa ttatttgtg cagcgatggg ggcggggggg | 660 |
| ggggggggc gcgcgccagg cggggcgggg cgggcgagg ggcggggcgg ggcgaggcgg | 720 |

-continued

```
agaggtgcgg cggcagccaa tcagagcggc gcgctccgaa agtttccttt tatggcgagg    780
cggcggcggc ggcggcccta taaaaagcga agcgcgcggc gggcgggagt cgctgcgacg    840
ctgccttcgc cccgtgcccc gctccgccgc cgcctcgcgc cgcccgcccc ggctctgact    900
gaccgcgtta ctcccacagg tgagcgggcg ggacggccct tctcctccgg gctgtaatta    960
gcgcttggtt taatgacggc ttgtttcttt tctgtggctg cgtgaaagcc ttgaggggct   1020 ccggagggc cctttgtgcg gggggagcg gctcggggg tgcgtgcgtg tgtgtgtgcg   1080
tggggagcgc cgcgtgcggc ccgcgctgcc cggcggctgt gagcgctgcg ggcgcggcgc   1140
ggggctttgt gcgctccgca gtgtgcgcga ggggagcgcg gccggggcg gtgccccgcg   1200 gtgcgggggg ggctgcgagg ggaacaaagg ctgcgtgcgg ggtgtgtgcg tggggggtg   1260 agcaggggt gtgggcgcgg cggtcgggct gtaaccccc cctgcacccc cctccccgag   1320
ttgctgagca cggcccggct tcgggtgcgg ggctccgtac ggggcgtggc gcggggctcg   1380
ccgtgccggg cggggtgg cggcaggtgg gggtgccggg cggggcgggg ccgcctcggg   1440
ccggggaggg ctcggggag gggcgcggcg gcccccggag cgccgcggc tgtcgaggcg   1500 cggcgagccg cagccattgc ctttatggt aatcgtgcga gagggcgcag ggacttcctt   1560
tgtcccaaat ctgtgcggag ccgaaatctg ggaggcgccg ccgcacccc tctagcgggc   1620 gcggggcgaa gcggtgcggc gccggcagga aggaaatggg cggggagggc cttcgtgcgt   1680
cgccgcgccg ccgtccccctt ctccctctcc agcctcgggg ctgtccgcgg ggggacggct   1740
gccttcgggg gggacggggc agggcgggggt tcggcttctg gcgtgtgacc ggcggctcta   1800
gagcctctgc taaccatgtt catgccttct tcttttttcct acagtcctg ggcaacgtgc   1860 tggttattgt gctgtctcat cattttggca agaattcct cgaagatcta ggcctgcagg   1920
cggccgccgc caccatgagc aagggcgagg aactgttcac tggcgtggtc ccaattctcg   1980
tggaactgga tggcgatgtg aatgggcaca aattttctgt cagcggagag ggtgaaggtg   2040
atgccacata cggaaagctc accctgaaat tcatctgcac cactggaaag ctccctgtgc   2100
catggccaac actggtcact accctgacct atggcgtgca gtgcttttcc agatacccag   2160
accatatgaa gcagcatgac ttttcaaga gcgccatgcc cgaggctat gtgcaggaga   2220 gaaccatctt tttcaaagat gacgggaact acaagacccg cgctgaagtc aagttcgaag   2280
gtgacaccct ggtgaataga atcgagctga agggcattga cttaaggag gatgaaaaca   2340 ttctcggcca caagctggaa tacaactata actcccacaa tgtgtacatc atggccgaca   2400
agcaaaagaa tggcatcaag gtcaacttca agatcagaca caacattgag gatggatccg   2460
tgcagctggc cgaccattat caacagaaca ctccaatcgg cgacggccct gtgctcctcc   2520
cagacaacca ttacctgtcc acccagtctg ccctgtctaa agatcccaac gaaaagagag   2580
accacatggt cctgctggag tttgtgaccg ctgctgggat cacacatggc atggacgagc   2640
tgtacaagtg agcggccgcg gggatccaga catgataaga tacattgatg agtttggaca   2700
aaccacaact agaatgcagt gaaaaaaatg ctttatttgt gaaatttgtg atgctattgc   2760
tttatttgta accattataa gctgcaataa acaagttaac aacaacaatt gcattcattt   2820
tatgtttcag gttcaggggg aggtgtggga ggttttttag tcgacctcga gcagtgtggt   2880
tttgcaagag gaagcaaaaa gcctctccac ccaggcctgg aatgtttcca cccaagtcga   2940
aggcagtgtg gttttgcaag aggaagcaaa aagcctctcc acccaggcct ggaatgtttc   3000
cacccaatgt cgagcaaccc cgcccagcgt cttgtcattg gcgaattcga acacgcagat   3060
gcagtcgggg cggcgcggtc ccaggtccac ttcgcatatt aaggtgacgc gtgtggcctc   3120
```

```
gaacaccgag cgaccctgca gccaatatgg gatcggccat tgaacaagat ggattgcacg    3180
caggttctcc ggccgcttgg gtggagaggc tattcggcta tgactgggca acagacaa      3240 tcggctgctc tgatgccgcc gtgttccggc tgtcagcgca ggggcgcccg gttcttttg     3300 tcaagaccga cctgtccggt gccctgaatg aactgcagga cgaggcagcg cggctatcgt    3360
ggctggccac gacgggcgtt ccttgcgcag ctgtgctcga cgttgtcact gaagcgggaa    3420
gggactggct gctattgggc gaagtgccgg ggcaggatct cctgtcatct caccttgctc    3480
ctgccgagaa agtatccatc atggctgatg caatgcggcg gctgcatacg cttgatccgg    3540
ctacctgccc attcgaccac caagcgaaac atcgcatcga gcgagcacgt actcggatgg    3600
aagccggtct tgtcgatcag gatgatctgg acgaagagca tcaggggctc gcgccagccg    3660
aactgttcgc caggctcaag gcgcgcatgc ccgacggcga ggatctcgtc gtgacccatg    3720
gcgatgcctg cttgccgaat atcatggtgg aaaatggccg cttttctgga ttcatcgact    3780
gtggccggct gggtgtggcg gaccgctatc aggacatagc gttggctacc cgtgatattg    3840
ctgaagagct tggcggcgaa tgggctgacc gcttcctcgt gctttacggt atcgccgctc    3900
ccgattcgca gcgcatcgcc ttctatcgcc ttcttgacga gttcttctga ggggatccgt    3960
cgactagagc tcgctgatca gcctcgactg tgccttctag ttgccagcca tctgttgttt    4020
gccccctccc cgtgccttcc ttgacctgg aaggtgccac tcccactgtc ctttcctaat     4080
aaaatgagga aattgcatcg cattgtctga gtaggtgtca ttctattctg gggggtgggg    4140
tggggcagga cagcaagggg gaggattggg aagacaatag caggcatgct ggggagagat    4200
ctaggaaccc ctagtgatgg agttggccac tccctctctg cgcgctcgct cgctcactga    4260
ggccgcccgg gcaaagcccg ggcgtcgggc gacctttggt cgcccggcct cagtgagcga    4320
gcgagcgcgc agagagggag tggccaaccc cccccccccc ccccctgcag ccctgcatta    4380
atgaatcggc caacgcgcgg ggagaggcgg tttgcgtatt gggcgctctt ccgcttcctc    4440
gctcactgac tcgctgcgct cggtcgttcg gctgcggcga gcggtatcag ctcactcaaa    4500
ggcggtaata cggttatcca cagaatcagg ggataacgca ggaaagaaca tgtgagcaaa    4560
aggccagcaa aaggccagga accgtaaaaa ggccgcgttg ctggcgtttt tccataggct    4620
ccgcccccct gacgagcatc acaaaaatcg acgctcaagt cagaggtggc gaaacccgac    4680
aggactataa agataccagg cgtttccccc tggaagctcc ctcgtgcgct ctcctgttcc    4740
gaccctgccg cttaccggat acctgtccgc ctttctccct tcgggaagcg tggcgctttc    4800
tcaatgctca cgctgtaggt atctcagttc ggtgtaggtc gttcgctcca agctgggctg    4860
tgtgcacgaa ccccccgttc agcccgaccg ctgcgcctta tccggtaact atcgtcttga    4920
gtccaacccg gtaagacacg acttatcgcc actggcagca gccactggta acaggattag    4980
cagagcgagg tatgtaggcg gtgctacaga gttcttgaag tggtggccta actacggcta    5040
cactagaagg acagtatttg gtatctgcgc tctgctgaag ccagttacct tcggaaaaag    5100
agttggtagc tcttgatccg gcaaacaaac caccgctggt agcggtggtt ttttgtttg    5160 caagcagcag attacgcgca gaaaaaaagg atctcaagaa gatcctttga tcttttctac    5220
ggggtctgac gctcagtgga acgaaaactc acgttaaggg attttggtca tgagattatc    5280
aaaaaggatc ttcacctaga tccttttaaa ttaaaaatga agttttaaat caatctaaag    5340
tatatatgag taaacttggt ctgacagtta ccaatgctta atcagtgagg cacctatctc    5400
agcgatctgt ctatttcgtt catccatagt tgcctgactc cccgtcgtgt agataactac    5460
gatacgggag ggcttaccat ctggccccag tgctgcaatg ataccgcgag acccacgctc    5520
```

-continued

```
accggctcca gatttatcag caataaacca gccagccgga agggccgagc gcagaagtgg    5580
tcctgcaact ttatccgcct ccatccagtc tattaattgt tgccgggaag ctagagtaag    5640
tagttcgcca gttaatagtt tgcgcaacgt tgttgccatt gctacaggca tcgtggtgtc    5700
acgctcgtcg tttggtatgg cttcattcag ctccggttcc caacgatcaa ggcgagttac    5760
atgatccccc atgttgtgca aaaaagcggt tagctccttc ggtcctccga tcgttgtcag    5820
aagtaagttg gccgcagtgt tatcactcat ggttatggca gcactgcata attctcttac    5880
tgtcatgcca tccgtaagat gcttttctgt gactggtgag tactcaacca agtcattctg    5940
agaatagtgt atgcggcgac cgagttgctc ttgcccggcg tcaatacggg ataataccgc    6000
gccacatagc agaactttaa aagtgctcat cattggaaaa cgttcttcgg ggcgaaaact    6060
ctcaaggatc ttaccgctgt tgagatccag ttcgatgtaa cccactcgtg cacccaactg    6120
atcttcagca tcttttactt tcaccagcgt ttctgggtga gcaaaaacag gaaggcaaaa    6180
tgccgcaaaa aagggaataa gggcgacacg gaaatgttga atactcatac tcttcctttt    6240
tcaatattat tgaagcattt atcagggtta ttgtctcatg agcggataca tatttgaatg    6300
tatttagaaa aataaacaaa tagggggttcc gcgcacattt ccccgaaaag tgccacctga    6360
cgtctaagaa accattatta tcatgacatt aacctataaa aataggcgta tcacgaggcc    6420
ctttcgtctc gcgcgtttcg gtgatgacgg tgaaaacctc tgacacatgc agctcccgga    6480
gacggtcaca gcttgtctgt aagcggatgc cgggagcaga caagcccgtc agggcgcgtc    6540
agcgggtgtt ggcgggtgtc ggggctggct taactatgcg gcatcagagc agattgtact    6600
gagagtgcac catatgcggt gtgaaatacc gcacagatgc gtaaggagaa ataccgcat    6660 caggaaattg taaacgttaa tattttgtta aaattcgcgt taaattttg ttaaatcagc    6720 tcatttttta accataggc cgaaatcggc aaaatccctt ataaatcaaa agaatagacc    6780
gagatagggt tgagtgttgt tccagtttgg aacaagagtc cactattaaa gaacgtggac    6840
tccaacgtca aagggcgaaa aaccgtctat cagggcgatg gcccactacg tgaaccatca    6900
ccctaatcaa gttttttggg gtcgaggtgc cgtaaagcac taaatcggaa ccctaaaggg    6960
agcccccgat ttagagcttg acggggaaag ccggcgaacg tggcgagaaa ggaagggaag    7020
aaagcgaaag gagcgggcgc tagggcgctg gcaagtgtag cggtcacgct gcgcgtaacc    7080
accacacccg ccgcgcttaa tgcgccgcta caggcgcgt cgcgccattc gccattcagg    7140
ctacgcaact gttgggaagg gcgatcggtg cgggcctctt cgctattacg ccaggctgca    7200
```

```
<210> SEQ ID NO 3
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 3
gagtggtacc accgccggcg taagaata                                        28

<210> SEQ ID NO 4
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 4
cctgatgtgg tagcacccgc cggcgtaaga ata                                  33
```

<210> SEQ ID NO 5
<211> LENGTH: 712
<212> TYPE: DNA
<213> ORGANISM: Artificial Sequence
<220> FEATURE:
<223> OTHER INFORMATION: Synthetic Polynucleotide

<400> SEQUENCE: 5

```
gatcttaccc cctgcccccc acagctcctc tcctgtgcct tgtttcccag ccatgcgttc      60
tcctctataa ataccgctc tggtatttgg ggttggcagc tgttgctgcc agggagatgg     120
ttgggttgac atgcggctcc tgacaaaaca caaaccctg gtgtgtgtgg cgtgggtgg      180
tgtgagtagg gggatgaatc agggagggg cggggaccc aggggcagg agccacacaa       240
agtctgtgcg ggggtgggag cgcacatagc aattggaaac tgaaagctta tcagaccctt    300
tctggaaatc agcccactgt ttataaactt gaggccccac cctcgagata accagggctg    360
aaagaggccc gcctgggggc tggagacatg cttgctgcct gccctggcga aggattggca    420
ggcttgcccg tcacaggacc cccgctggct gactcagggg cgcaggcctc ttgcggggga    480
gctggcctcc ccgccccac ggccacgggc cgccctttcc tggcaggaca gcgggatctt     540
gcagctgtca ggggagggga ggcggggct gatgtcagga gggatacaaa tagtgccgac     600
ggctggggc cctgtctccc ctcgccgcat ccactctccg gccggccgcc tgtccgccgc     660
ctcctccgtg cgcccgccag cctcgcccgc gccgtcaccg tgaggcactg gg            712
```

<210> SEQ ID NO 6
<211> LENGTH: 410
<212> TYPE: DNA
<213> ORGANISM: Artificial Sequence
<220> FEATURE:
<223> OTHER INFORMATION: Synthetic Polynucleotide

<400> SEQUENCE: 6

```
ccctaaaatg ggcaaacatt gcaagcagca acagcaaac acacagccct ccctgcctgc      60
tgaccttgga gctggggcag aggtcagaga cctctctggg gactgtccca ggtcagtggt    120
ggtgcctgaa gctgaggaga cagggccctg tcctcgtccg tatttaagca gtggatccag    180
aggggcaacg ggggaggctg ctggtgaata ttaaccaagg tcaccccagt tatcggagga    240
gcaaacaggg gctaagtcca ctggctggga tctgagtcgc ccgcctacgc tgcccggacg    300
cttgcctgg gcagtgtaca gcttccactg cacttaccga aaggagtcat tgtagggccc     360
tgtctcctca gcttcaggca ccaccactga cctgggacag tgaatccgga                410
```

<210> SEQ ID NO 7
<211> LENGTH: 7390
<212> TYPE: DNA
<213> ORGANISM: Artificial Sequence
<220> FEATURE:
<223> OTHER INFORMATION: Synthetic Polynucleotide

<400> SEQUENCE: 7

```
tcgaggacaa ccttagtgaa ggaattcgcg agtggtgggc tttgaaacct ggagcccctc      60
aacccaaggc aaatcaacaa catcaagaca acgtcgagg tcttgtgctt ccgggttaca     120
aataccttgg acccggcaac ggactcgaca aggggagcc ggtcaacgca gcagacgcgg     180
cggccctcga gcacgacaag gcctacgacc agcagctcaa ggccggagac aacccgtacc    240
tcaagtacaa ccacgccgac gccgagttcc aggagcggct caaagaagat acgtcttttg    300
ggggcaaccct cggcgagca gtcttccagg ccaaaaagag gcttcttgaa cctcttggtc    360
```

```
tggttgagga agcggctaag acggctcctg gaaagaagag gcctgtagag cagtctcctc    420
aggaaccgga ctcctccgcg ggtattggca atcgggtgc acagcccgct aaaaagagac    480
tcaatttcgg tcagactggc gacacagagt cagtcccaga ccctcaacca atcggagaac    540
ctcccgcagc cccctcaggt gtgggatctc ttacaatggc ttcaggtggt ggcgcaccag    600
tggcagacaa taacgaaggt gccgatggag tgggtagttc ctcgggaaat tggcattgcg    660
attcccaatg gctggggggac agagtcatca ccaccagcac ccgaacctgg gccctgccca    720
cctacaacaa tcacctctac aagcaaatct ccaacagcac atctggagga tcttcaaatg    780
acaacgccta cttcggctac agcaccccct ggggtattt tgacttcaac agattccact    840
gccacttctc accacgtgac tggcagcgac tcatcaacaa caactgggga ttccggccta    900
agcgactcaa cttcaagctc ttcaacattc aggtcaaaga ggttacggac aacaatggag    960
tcaagaccat cgccaataac cttaccagca cggtccaggt cttcacggac tcagactatc    1020
agctcccgta cgtgctcggg tcggctcacg agggctgcct cccgccgttc ccagcggacg    1080
ttttcatgat tcctcagtac gggtatctga cgcttaatga tggaagccag gccgtgggtc    1140
gttcgtcctt ttactgcctg aatatttccc cgtcgcaaat gctaagaacg ggtaacaact    1200
tccagttcag ctacgagttt gagaacgtac ctttccatag cagctacgct cacagccaaa    1260
gcctggaccg actaatgaat ccactcatcg accaatactt gtactatctc tcaaagacta    1320
ttaacggttc tggacagaat caacaaacgc taaaattcag tgtggccgga cccagcaaca    1380
tggctgtcca gggaagaaac tacatacctg acccagcta ccgacaacaa cgtgtctcaa    1440
ccactgtgac tcaaaacaac aacagcgaat ttgcttggcc tggagcttct tcttgggctc    1500
tcaatggacg taatagcttg atgaatcctg gacctgctat ggccagccac aaagaaggag    1560
aggaccgttt cttttccttg tctggatctt taattttgg caaacaagga actgaaagag    1620
acaacgtgga tgcggacaaa gtcatgataa ccaacgaaga agaaattaaa actactaacc    1680
cggtagcaac ggagtcctat ggacaagtgg ccacaaacca ccagagtgcc caagcacagg    1740
cgcagaccgg ctgggttcaa aaccaaggaa tacttccggg tatggtttgg caggacagag    1800
atgtgtacct gcaaggaccc atttgggcca aaattcctca cacggacggc aactttcacc    1860
cttctccgct gatgggaggg tttggaatga agcacccgcc tcctcagatc ctcatcaaaa    1920
acacacctgt acctgcggat cctccaacgg ccttcaacaa ggacaagctg aactcttca    1980 tcacccagta ttctactggc caagtcagcg tggagatcga gtgggagctg cagaaggaaa    2040
acagcaagcg ctggaacccg gagatccagt acacttccaa ctattacaag tctaataatg    2100
ttgaatttgc tgttaatact gaaggtgtat atagtgaacc ccgccccatt ggcaccagat    2160
acctgactcg taatctgtaa ttgcttgtta atcaataaac cgtttaattc gtttcagttg    2220
aactttggtc tctgcgaagg gcgaattcgt ttaaacctgc aggactagag tcctgtatta    2280
gaggtcacgt gagtgttttg cgacattttg cgacaccatg tggtcacgct gggtatttaa    2340
gcccgagtga gcacgcaggg tctccatttt gaagcgggag gtttgaacgc gcagccgcca    2400
agccgaattc tgcagatatc catcacactg gcggccgctc gactagagcg gccgccaccg    2460
cggtggagct ccagcttttg ttcccttag tgagggttaa ttgcgcgctt ggcgtaatca    2520
tggtcatagc tgtttcctgt gtgaaattgt tatccgctca caattccaca acatacga    2580 gccggaagca taaagtgtaa agcctggggt gcctaatgag tgagctaact cacattaatt    2640
gcgttgcgct cactgcccgc tttccagtcg ggaaacctgt cgtgccagct gcattaatga    2700
atcggccaac gcgcggggag aggcggtttg cgtattgggc gctcttccgc ttcctcgctc    2760
```

```
actgactcgc tgcgctcggt cgttcggctg cggcgagcgg tatcagctca ctcaaaggcg    2820
gtaatacggt tatccacaga atcaggggat aacgcaggaa agaacatgtg agcaaaaggc    2880
cagcaaaagg ccaggaaccg taaaaaggcc gcgttgctgg cgttttccca taggctccgc    2940 cccctgacg agcatcacaa aaatcgacgc tcaagtcaga ggtggcgaaa cccgacagga    3000
ctataaagat accaggcgtt tccccctgga agctccctcg tgcgctctcc tgttccgacc    3060
ctgccgctta ccggatacct gtccgccttt ctcccttcgg gaagcgtggc gctttctcat    3120
agctcacgct gtaggtatct cagttcggtg taggtcgttc gctccaagct gggctgtgtg    3180
cacgaacccc ccgttcagcc cgaccgctgc gccttatccg gtaactatcg tcttgagtcc    3240
aacccggtaa gacacgactt atcgccactg gcagcagcca ctggtaacag gattagcaga    3300
gcgaggtatg taggcggtgc tacagagttc ttgaagtggt ggcctaacta cggctacact    3360
agaaggacag tatttggtat ctgcgctctg ctgaagccag ttaccttcgg aaaaagagtt    3420
ggtagctctt gatccggcaa acaaaccacc gctggtagcg gtggtttttt tgtttgcaag    3480
cagcagatta cgcgcagaaa aaaggatctc aagaagatc ctttgatctt ttctacgggg    3540
tctgacgctc agtggaacga aaactcacgt taagggattt tggtcatgag attatcaaaa    3600
aggatcttca cctagatcct tttaaattaa aaatgaagtt ttaaatcaat ctaaagtata    3660
tatgagtaaa cttggtctga cagttaccaa tgcttaatca gtgaggcacc tatctcagcg    3720
atctgtctat ttcgttcatc catagttgcc tgactcccg tcgtgtagat aactacgata    3780
cgggagggct taccatctgg ccccagtgct gcaatgatac cgcgagaccc acgctcaccg    3840
gctccagatt tatcagcaat aaaccagcca gccggaaggg ccgagcgcag aagtggtcct    3900
gcaactttat ccgcctccat ccagtctatt aattgttgcc gggaagctag agtaagtagt    3960
tcgccagtta atagtttgcg caacgttgtt gccattgcta caggcatcgt ggtgtcacgc    4020
tcgtcgtttg gtatggcttc attcagctcc ggttcccaac gatcaaggcg agttacatga    4080
tcccccatgt tgtgcaaaaa agcggttagc tccttcggtc ctccgatcgt tgtcagaagt    4140
aagttggccg cagtgttatc actcatggtt atggcagcac tgcataattc tcttactgtc    4200
atgccatccg taagatgctt tctgtgactg gtgagtactc aaccaagtca ttctgagaat    4260
agtgtatgcg gcgaccgagt tgctcttgcc cggcgtcaat acgggataat accgcgccac    4320
atagcagaac tttaaaagtg ctcatcattg gaaaacgttc ttcggggcga aaactctcaa    4380
ggatcttacc gctgttgaga tccagttcga tgtaacccac tcgtgcaccc aactgatctt    4440
cagcatcttt tactttcacc agcgtttctg ggtgagcaaa aacaggaagg caaaatgccg    4500
caaaaaaggg aataagggcg acacggaaat gttgaatact catactcttc ctttttcaat    4560
attattgaag catttatcag ggttattgtc tcatgagcgg atacatattt gaatgtattt    4620
agaaaaataa acaaataggg gttccgcgca catttccccg aaaagtgcca cctaaattgt    4680
aagcgttaat attttgttaa aattcgcgtt aaattttgt taaatcagct catttttaa    4740 ccaataggcc gaaatcggca aaatccctta taatcaaaa gaatagaccg agatagggtt    4800
gagtgttgtt ccagtttgga acaagagtcc actattaaag aacgtggact ccaacgtcaa    4860
agggcgaaaa accgtctatc agggcgatgg cccactacgt gaaccatcac cctaatcaag    4920
ttttttgggg tcgaggtgcc gtaaagcact aaatcggaac cctaaaggga gcccccgatt    4980
tagagcttga cggggaaagc cggcgaacgt ggcgagaaag gaagggaaga aagcgaaagg    5040
agcgggcgct agggcgctgg caagtgtagc ggtcacgctg cgcgtaacca ccacacccgc    5100
```

```
cgcgcttaat gcgccgctac agggcgcgtc ccattcgcca ttcaggctgc gcaactgttg    5160
ggaagggcga tcggtgcggg cctcttcgct attacgccag ctggcgaaag ggggatgtgc    5220
tgcaaggcga ttaagttggg taacgccagg gttttcccag tcacgacgtt gtaaaacgac    5280
ggccagtgag cgcgcgtaat acgactcact atagggcgaa ttgggtaccg ggccccccct    5340
cgatcgaggt cgacggtatc gggggagctc ggatccacta gtaacggccg ccagtgtgct    5400
ggattcggct ttatttaagc ccgagtgagc acgcagggtc tccattttga agcgggaggt    5460
ttgaacgcgc agccgccatg ccggggtttt acgagattgt gattaaggtc cccagcgacc    5520
ttgacgggca tctgcccggc atttctgaca gctttgtgaa ctgggtggcc gagaaggaat    5580
gggagttgcc gccagattct gacatggatc tgaatctgat tgagcaggca ccctgaccg     5640
tggccgagaa gctgcagcgc gactttctga cggaatggcg ccgtgtgagt aaggccccgg    5700
aggcccttt ctttgtgcaa tttgagaagg gagagagcta cttccacatg cacgtgctcg     5760
tggaaaccac cggggtgaaa tccatggttt tgggacgttt cctgagtcag attcgcgaaa    5820
aactgattca gagaatttac cgcgggatcg agccgacttt gccaaactgg ttcgcggtca    5880
caaagaccag aaatggcgcc ggaggcggga acaaggtggt ggatgagtgc tacatcccca    5940
attacttgct ccccaaaacc cagcctgagc tccagtgggc gtggactaat atggaacagt    6000
atttaagcgc ctgtttgaat ctcacggagc gtaaacggtt ggtggcgcag catctgacgc    6060
acgtgtcgca gacgcaggag cagaacaaag agaatcagaa tcccaattct gatgcgccgg    6120
tgatcagatc aaaaacttca gccaggtaca tggagctggt cgggtggctc gtggacaagg    6180
ggattacctc ggagaagcag tggatccagg aggaccaggc ctcatacatc tccttcaatg    6240
cggcctccaa ctcgcggtcc caaatcaagg ctgccttgga caatgcggga aagattatga    6300
gcctgactaa aaccgccccc gactacctgg tgggccagca gcccgtggag gacatttcca    6360
gcaatcggat ttataaaatt ttggaactaa acgggtacga tccccaatat gcggcttccg    6420
tctttctggg atgggccacg aaaaagttcg gcaagaggaa caccatctgg ctgtttgggc    6480
ctgcaactac cgggaagacc aacatcgcgg aggccatagc ccacactgtg cccttctacg    6540
ggtgcgtaaa ctggaccaat gagaactttc ccttcaacga ctgtgtcgac aagatggtga    6600
tctggtggga ggaggggaag atgaccgcca aggtcgtgga gtcggccaaa gccattctcg    6660
gaggaagcaa ggtgcgcgtg gaccagaaat gcaagtcctc ggcccagata gacccgactc    6720
ccgtgatcgt cacctccaac accaacatgt gcgccgtgat tgacgggaac tcaacgacct    6780
tcgaacacca gcagccgttg caagaccgga tgttcaaatt tgaactcacc cgccgtctgg    6840
atcatgactt tgggaaggtc accaagcagg aagtcaaaga cttttttccgg tgggcaaagg    6900
atcacgtggt tgaggtggag catgaattct acgtcaaaaa gggtggagcc aagaaaagac    6960
ccgcccccag tgacgcagat ataagtgagc caaacgggt gcgcgagtca gttgcgcagc     7020
catcgacgtc agacgcggaa gcttcgatca actacgcgga caggtaccaa aacaaatgtt    7080
ctcgtcacgt gggcatgaat ctgatgctgt ttccctgcag acaatgcgag agactgaatc    7140
agaattcaaa tatctgcttc actcacggtg tcaaagactg tttagagtgc tttcccgtgt    7200
cagaatctca acccgtttct gtcgtcaaaa aggcgtatca gaaactgtgc tacattcatc    7260
acatcatggg aaaggtgcca gacgcttgca ctgcttgcga cctggtcaat gtggacttgg    7320
atgactgtgt ttctgaacaa taaatgactt aaaccaggta tggctgccga tggttatctt    7380
ccagattggc                                                           7390
```

<210> SEQ ID NO 8
<211> LENGTH: 18930
<212> TYPE: DNA
<213> ORGANISM: Artificial Sequence
<220> FEATURE:
<223> OTHER INFORMATION: Synthetic Polynucleotide

<400> SEQUENCE: 8

| | | | | | |
|---|---|---|---|---|---|
| tcttccgctt | cctcgctcac | tgactcgctg | cgctcggtcg | ttcggctgcg | gcgagcggta | 60 |
| tcagctcact | caaaggcggt | aatacggtta | tccacagaat | caggggataa | cgcaggaaag | 120 |
| aacatgtgag | caaaaggcca | gcaaaaggcc | aggaaccgta | aaaaggccgc | gttgctggcg | 180 |
| tttttccata | ggctccgccc | ccctgacgag | catcacaaaa | atcgacgctc | aagtcagagg | 240 |
| tggcgaaacc | cgacaggact | ataaagatac | caggcgtttc | ccctggaag | ctccctcgtg | 300 |
| cgctctcctg | ttccgaccct | gccgcttacc | ggatacctgt | ccgcctttct | cccttcggga | 360 |
| agcgtggcgc | tttctcatag | ctcacgctgt | aggtatctca | gttcggtgta | ggtcgttcgc | 420 |
| tccaagctgg | gctgtgtgca | cgaaccccc | gttcagcccg | accgctgcgc | cttatccggt | 480 |
| aactatcgtc | ttgagtccaa | cccggtaaga | cacgacttat | cgccactggc | agcagccact | 540 |
| ggtaacagga | ttagcagagc | gaggtatgta | ggcggtgcta | cagagttctt | gaagtggtgg | 600 |
| cctaactacg | gctacactag | aagaacagta | tttggtatct | gcgctctgct | gaagccagtt | 660 |
| accttcggaa | aaagagttgg | tagctcttga | tccggcaaac | aaaccaccgc | tggtagcggt | 720 |
| ggtttttttg | tttgcaagca | gcagattacg | cgcagaaaaa | aaggatctca | agaagatcct | 780 |
| ttgatctttt | ctacggggtc | tgacgctcag | tggaacgaaa | actcacgtta | agggattttg | 840 |
| gtcatgagat | tatcaaaaag | gatcttcacc | tagatccttt | taaattaaaa | atgaagtttt | 900 |
| aaatcaatct | aaagtatata | tgagtaaact | tggtctgaca | gttaccaatg | cttaatcagt | 960 |
| gaggcaccta | tctcagcgat | ctgtctattt | cgttcatcca | tagttgcctg | actccccgtc | 1020 |
| gtgtagataa | ctacgatacg | ggagggctta | ccatctggcc | ccagtgctgc | aatgataccg | 1080 |
| cgagacccac | gctcaccggc | tccagattta | tcagcaataa | accagccagc | cggaagggcc | 1140 |
| gagcgcagaa | gtggtcctgc | aactttatcc | gcctccatcc | agtctattaa | ttgttgccgg | 1200 |
| gaagctagag | taagtagttc | gccagttaat | agtttgcgca | acgttgttgc | cattgctaca | 1260 |
| ggcatcgtgg | tgtcacgctc | gtcgtttggt | atggcttcat | tcagctccgg | ttcccaacga | 1320 |
| tcaaggcgag | ttacatgatc | ccccatgttg | tgcaaaaaag | cggttagctc | cttcggtcct | 1380 |
| ccgatcgttg | tcagaagtaa | gttggccgca | gtgttatcac | tcatggttat | ggcagcactg | 1440 |
| cataattctc | ttactgtcat | gccatccgta | agatgctttt | ctgtgactgg | tgagtactca | 1500 |
| accaagtcat | tctgagaata | gtgtatgcgg | cgaccgagtt | gctcttgccc | ggcgtcaata | 1560 |
| cgggataata | ccgcgccaca | tagcagaact | ttaaaagtgc | tcatcattgg | aaaacgttct | 1620 |
| tcggggcgaa | aactctcaag | gatcttaccg | ctgttgagat | ccagttcgat | gtaacccact | 1680 |
| cgtgcaccca | actgatcttc | agcatctttt | actttcacca | gcgtttctgg | gtgagcaaaa | 1740 |
| acaggaaggc | aaaatgccgc | aaaaaaggga | ataagggcga | cacggaaatg | ttgaatactc | 1800 |
| atactcttcc | tttttcaata | ttattgaagc | atttatcagg | gttattgtct | catgagcgga | 1860 |
| tacatatttg | aatgtattta | gaaaaataaa | caaatagggg | ttccgcgcac | atttccccga | 1920 |
| aaagtgccac | ctgacgtcta | agaaaccatt | attatcatga | cattaaccta | taaaaatagg | 1980 |
| cgtatcacga | ggccctttcg | tctcgcgcgt | ttcggtgatg | acggtgaaaa | cctctgacac | 2040 |
| atgcagctcc | cggagacggt | cacagcttgt | ctgtaagcgg | atgccgggag | cagacaagcc | 2100 |

```
cgtcagggcg cgtcagcggg tgttggcggg tgtcggggct ggcttaacta tgcggcatca   2160
gagcagattg tactgagagt gcaccataaa attgtaaacg ttaatatttt gttaaaattc   2220
gcgttaaatt tttgttaaat cagctcattt tttaaccaat aggccgaaat cggcaaaatc   2280
ccttataaat caaagaata gcccgagata gggttgagtg ttgttccagt ttggaacaag   2340
agtccactat taaagaacgt ggactccaac gtcaaagggc gaaaaaccgt ctatcagggc   2400
gatggcccac tacgtgaacc atcacccaaa tcaagttttt tggggtcgag gtgccgtaaa   2460
gcactaaatc ggaaccctaa agggagcccc cgatttagag cttgacgggg aaagccggcg   2520
aacgtggcga aaaggaagg gaagaaagcg aaaggagcgg gcgctagggc gctggcaagt   2580
gtagcggtca cgctgcgcgt aaccaccaca cccgccgcgc ttaatgcgcc gctacagggc   2640
gcgtactatg gttgctttga cgtatgcggt gtgaaatacc gcacagatgc gtaaggagaa   2700
aataccgcat caggcgccat cgccattca ggctgcgcaa ctgttgggaa gggcgatcgg   2760
tgcgggcctc ttcgctatta cgccagctgg cgaaaggggg atgtgctgca aggcgattaa   2820
gttgggtaac gccagggttt cccagtcac gacgttgtaa aacgacggcc agtgccaagc   2880
ttaaggtgca cggcccacgt ggccactagt acttctcgac agaagcacca tgtccttggg   2940
tccggcctgc tgaatgcgca ggcggtcggc catgccccag gcttcgtttt gacatcggcg   3000
caggtctttg tagtagtctt gcatgagcct ttctaccggc acttcttctt ctccttcctc   3060
ttgtcctgca tctcttgcat ctatcgctgc ggcggcggcg gagtttggcc gtaggtggcg   3120
ccctcttcct cccatgcgtg tgaccccgaa gcccctcatc ggctgaagca gggctaggtc   3180
ggcgacaacg cgctcggcta atatggcctg ctgcacctgc gtgagggtag actggaagtc   3240
atccatgtcc acaaagcggt ggtatgcgcc cgtgttgatg gtgtaagtgc agttggccat   3300 aacgaccag ttaacggtct ggtgaccgg ctgcgagagc tcggtgtacc tgagacgcga   3360
gtaagccctc gagtcaaata cgtagtcgtt gcaagtccgc accaggtact ggtatcccac   3420 caaaagtgc ggcggcggct ggcggtagag gggccagcgt agggtggccg gggctccggg   3480
ggcgagatct tccaacataa ggcgatgata tccgtagatg tacctggaca tccaggtgat   3540
gccggcggcg gtggtggagg cgcgcggaaa gtcgcggacg cggttccaga tgttgcgcag   3600
cggcaaaaag tgctccatgg tcgggacgct ctggccggtc aggcgcgcgc aatcgttgac   3660
gctctaccgt gcaaaaggag agcctgtaag cgggcactct tccgtggtct ggtgataaa   3720 ttcgcaaggg tatcatggcg gacgaccggg gttcgagccc cgtatccggc cgtccgccgt   3780
gatccatgcg gttaccgccc gcgtgtcgaa cccaggtgtg cgacgtcaga caacggggga   3840
gtgctccttt tggcttcctt ccaggcgcgg cggctgctgc gctagctttt ttggccactg   3900
gccgcgcgca gcgtaagcgg ttaggctgga aagcgaaagc attaagtggc tcgctccctg   3960
tagccggagg gttatttttcc aagggttgag tcgcgggacc cccggttcga gtctcggacc   4020
ggccggactg cggcgaacgg gggtttgcct ccccgtcatg caagaccccg cttgcaaatt   4080
cctccggaaa cagggacgag ccccttttttt gcttttccca gatgcatccg gtgctgcggc   4140
agatgcgccc ccctcctcag cagcggcaag agcaagagca gcggcagaca tgcagggcac   4200
cctcccctcc tcctaccgcg tcaggagggg cgacatccgc ggttgacgcg gcagcagatg   4260
gtgattacga acccccgcgg cgccgggccc ggcactacct ggacttggag gagggcgagg   4320
gcctggcgcg gctaggagcg ccctctcctg agcggtaccc aagggtgcag ctgaagcgtg   4380
atacgcgtga ggcgtacgtg ccgcggcaga acctgtttcg cgaccgcgag ggagaggagc   4440
ccgaggagat gcgggatcga aagttccacg cagggcgcga gctgcggcat ggcctgaatc   4500
```

```
gcgagcggtt gctgcgcgag gaggactttg agcccgacgc gcgaaccggg attagtcccg    4560
cgcgcgcaca cgtggcggcc gccgacctgg taaccgcata cgagcagacg gtgaaccagg    4620
agattaactt tcaaaaaagc tttaacaacc acgtgcgtac gcttgtggcg cgcgaggagg    4680
tggctatagg actgatgcat ctgtgggact ttgtaagcgc gctggagcaa aacccaaata    4740
gcaagccgct catggcgcag ctgttcctta tagtgcagca cagcagggac aacgaggcat    4800
tcagggatgc gctgctaaac atagtagagc ccgagggccg ctggctgctc gatttgataa    4860
acatcctgca gagcatagtg gtgcaggagc gcagcttgag cctggctgac aaggtggccg    4920
ccatcaacta ttccatgctt agcctgggca agttttacgc ccgcaagata taccataccc    4980
cttacgttcc catagacaag gaggtaaaga tcgaggggtt ctacatgcgc atggcgctga    5040
aggtgcttac cttgagcgac gacctgggcg tttatcgcaa cgagcgcatc cacaaggccg    5100
tgagcgtgag ccggcggcgc gagctcagcg accgcgagct gatgcacagc ctgcaaaggg    5160
ccctggctgg cacgggcagc ggcgatagag aggccgagtc ctactttgac gcgggcgctg    5220
acctgcgctg ggccccaagc cgacgcgccc tggaggcagc tggggccgga cctgggctgg    5280
cggtggcacc cgcgcgcgct ggcaacgtcg gcggcgtgga ggaatatgac gaggacgatg    5340
agtacgagcc agaggacggc gagtactaag cggtgatgtt tctgatcaga tgatgcaaga    5400
cgcaacggac ccggcggtgc gggcggcgct gcagagccag ccgtccggcc ttaactccac    5460
ggacgactgg cgccaggtca tggaccgcat catgtcgctg actgcgcgca atcctgacgc    5520
gttccggcag cagccgcagg ccaaccggct ctccgcaatt ctggaagcgg tggtcccggc    5580
gcgcgcaaac cccacgcacg agaaggtgct ggcgatcgta aacgcgctgg ccgaaaacag    5640
ggccatccgg cccgacgagg ccggcctggt ctacgacgcg ctgcttcagc gcgtggctcg    5700
ttacaacagc ggcaacgtgc agaccaacct ggaccggctg gtgggggatg tgcgcgaggc    5760
cgtggcgcag cgtgagcgcg cgcagcagca gggcaacctg gctccatgg ttgcactaaa    5820 cgccttcctg agtacacagc ccgccaacgt gccgcgggga caggaggact acaccaactt    5880
tgtgagcgca ctgcggctaa tggtgactga dacaccgcaa agtgaggtgt accagtctgg    5940
gccagactat tttttccaga ccagtagaca aggcctgcag accgtaaacc tgagccaggc    6000
tttcaaaaac ttgcaggggc tgtgggggt gcgggctccc acaggcgacc gcgcgaccgt    6060
gtctagcttg ctgacgccca actcgcgcct gttgctgctg ctaatagcgc ccttcacgga    6120
cagtggcagc gtgtcccggg acacatacct aggtcacttg ctgacactgt accgcgaggc    6180
cataggtcag gcgcatgtgg acgagcatac tttccaggag attacaagtg tcagccgcgc    6240
gctggggcag gaggacacgg gcagcctgga ggcaaccta aactacctgc tgaccaaccg    6300
gcggcagaag atcccctcgt tgcacagttt cgcaccctt ggcgcatccc attctccagt    6360
aactttatgt ccatgggcgc actcacagac ctgggccaaa accttctcta cgccaactcc    6420
gcccacgcgc tagacatgac ttttgaggtg gatcccatgg acgagcccac ccttctttat    6480
gttttgtttg aagtctttga cgtggtccgt gtgcaccggc cgcaccgcgg cgtcatcgaa    6540
accgtgtacc tgcgcacgcc cttctcggcc ggcaacgcca caacataaag aagcaagcaa    6600
catcaacaac agctgccgcc atgggctcca gtgagcagga actgaaagcc attgtcaaag    6660
atcttggttg tgggccatat ttttgggca cctatgacaa gcgctttcca ggctttgttt    6720
ctccacacaa gctcgcctgc gccatagtca atacggccgg tcgcgagact gggggcgtac    6780
actggatggc ctttgcctgg aacccgcact caaaaacatg ctacctcttt gagcccttttg    6840 gcttttctga ccagcgactc aagcaggttt accagtttga gtacgagtca ctcctgcgcc    6900
```

```
gtagcgccat tgcttcttcc cccgaccgct gtataacgct ggaaaagtcc acccaaagcg   6960
tacaggggcc caactcggcc gcctgtggac tattctgctg catgtttctc cacgcctttg   7020
ccaactggcc ccaaactccc atggatcaca accccaccat gaaccttatt accggggtac   7080
ccaactccat gctcaacagt ccccaggtac agcccacccg cgtcgcaac caggaacagc    7140 tctacagctt cctggagcgc cactcgccct acttccgcag ccacagtgcg cagattagga   7200
gcgccacttc tttttgtcac ttgaaaaaca tgtaaaaata atgtactaga gacactttca   7260
ataaaggcaa atgcttttat ttgtacactc tcgggtgatt atttaccccc acccttgccg   7320
tctgcgccgt ttaaaaatca aagggggttct gccgcgcatc gctatgcgcc actggcaggg  7380
acacgttgcg atactggtgt ttagtgctcc acttaaactc aggcacaacc atccgcggca   7440
gctcggtgaa gttttcactc cacaggctgc gcaccatcac caacgcgttt agcaggtcgg   7500
gcgccgatat cttgaagtcg cagttggggc ctccgccctg cgcgcgcgag ttgcgataca   7560
cagggttgca gcactggaac actatcagcg ccgggtggtg cacgctggcc agcacgctct   7620
tgtcggagat cagatccgcg tccaggtcct ccgcgttgct cagggcgaac ggagtcaact   7680
ttggtagctg ccttcccaaa aagggcgcgt gcccaggctt tgagttgcac tcgcaccgta   7740
gtggcatcaa aaggtgaccg tgcccggtct gggcgttagg atacagcgcc tgcataaaag   7800
ccttgatctg cttaaaagcc acctgagcct ttgcgccttc agagaagaac atgccgcaag   7860
acttgccgga aaactgattg gccggacagg ccgcgtcgtg cacgcagcac cttgcgtcgg   7920
tgttggagat ctgcaccaca tttcggcccc accggttctt cacgatcttg gccttgctag   7980
actgctcctt cagcgcgcgc tgcccgtttt cgctcgtcac atccatttca atcacgtgct   8040
ccttatttat cataatgctt ccgtgtagac acttaagctc gccttcgatc tcagcgcagc   8100
ggtgcagcca caacgcgcag cccgtgggct cgtgatgctt gtaggtcacc tctgcaaacg   8160
actgcaggta cgcctgcagg aatcgcccca tcatcgtcac aaaggtcttg ttgctggtga   8220
aggtcagctg caacccgcgg tgctcctcgt tcagccaggt cttgcatacg gccgccagag   8280
cttccacttg gtcaggcagt agtttgaagt tcgcctttag atcgttatcc acgtggtact   8340
tgtccatcag cgcgcgcgca gcctccatgc ccttctccca cgcagacacg atcggcacac   8400
tcagcgggtt catcaccgta atttcacttt ccgcttcgct gggctcttcc tcttcctctt   8460
gcgtccgcat accacgcgcc actgggtcgt cttcattcag ccgccgcact gtgcgcttac   8520
ctcctttgcc atgcttgatt agcaccggtg ggttgctgaa acccaccatt tgtagcgcca   8580
catcttctct ttcttcctcg ctgtccacga ttacctctgg tgatggcggg cgctcgggct   8640
tgggagaagg gcgcttcttt ttcttcttgg gcgcaatggc caaatccgcc gccgaggtcg   8700
atggccgcgg gctgggtgtg cgcggcacca gcgcgtcttg tgatgagtct tcctcgtcct   8760
cggactcgat acgccgcctc atccgctttt ttggggggcgc ccggggaggc ggcggcgacg   8820
gggacgggga cgacacgtcc tccatggttg ggggacgtcg cgccgcaccg cgtccgcgct   8880
cgggggtggt ttcgcgctgc tcctcttccc gactggccat ttccttctcc tataggcaga   8940
aaaagatcat ggagtcagtc gagaagaagg acagcctaac cgcccctct gagttcgcca    9000 ccaccgcctc caccgatgcc gccaacgcgc taccaccttc cccgtcgag gcaccccgc     9060 ttgaggagga ggaagtgatt atcgagcagg acccaggttt tgtaagcgaa gacgacgagg   9120
accgctcagt accaacagag gataaaaagc aagaccagga caacgcagag gcaaacgagg   9180
aacaagtcgg gcgggggggac gaaaggcatg gcgactacct agatgtggga gacgacgtgc   9240
tgttgaagca tctgcagcgc cagtgcgcca ttatctgcga cgcgttgcaa gagcgcagcg   9300
```

```
atgtgcccct cgccatagcg gatgtcagcc ttgcctacga acgccaccta ttctcaccgc   9360
gcgtacccccc caaacgccaa gaaaacggca catgcgagcc caacccgcgc ctcaacttct   9420
accccgtatt tgccgtgcca gaggtgcttg ccacctatca catcttttc caaaactgca   9480
agatacccct atcctgccgt gccaaccgca gccgagcgga caagcagctg gccttgcggc   9540
agggcgctgt catacctgat atcgcctcgc tcaacgaagt gccaaaaatc tttgagggtc   9600
ttggacgcga cgagaagcgc gcggcaaacg ctctgcaaca ggaaaacagc gaaaatgaaa   9660
gtcactctgg agtgttggtg gaactcgagg gtgacaacgc gcgcctagcc gtactaaaac   9720
gcagcatcga ggtcacccac tttgcctacc cggcacttaa cctaccccccc aaggtcatga   9780
gcacagtcat gagtgagctg atcgtgcgcc gtgcgcagcc cctggagagg gatgcaaatt   9840
tgcaagaaca aacagaggag ggcctacccg cagttggcga cgagcagcta gcgcgctggc   9900
ttcaaacgcg cgagcctgcc gacttggagg agcgacgcaa actaatgatg gccgcagtgc   9960
tcgttaccgt ggagcttgag tgcatgcagc ggttctttgc tgacccggag atgcagcgca  10020
agctagagga aacattgcac tacacctttc gacagggcta cgtacgccag gcctgcaaga  10080
tctccaacgt ggagctctgc aacctggtct cctaccttgg aattttgcac gaaaaccgcc  10140
ttgggcaaaa cgtgcttcat tccacgctca agggcgaggc gcgccgcgac tacgtccgcg  10200
actgcgttta cttatttcta tgctacacct ggcagacggc catgggcgtt tggcagcagt  10260
gcttggagga gtgcaacctc aaggagctgc agaaactgct aaagcaaaac ttgaaggacc  10320
tatggacggc cttcaacgag cgctccgtgg ccgcgcacct ggcggacatc attttccccg  10380
aacgcctgct taaacccctg caacagggtc tgccagactt caccagtcaa gcatgttgc   10440
agaactttag gaactttatc ctagagcgct caggaatctt gcccgccacc tgctgtgcac  10500
ttcctagcga ctttgtgccc attaagtacc gcgaatgccc tccgccgctt tggggccact  10560
gctaccttct gcagctagcc aactaccttg cctaccactc tgacataatg gaagacgtga  10620
gcggtgacgg tctactggag tgtcactgtc gctgcaacct atgcaccccg caccgctccc  10680
tggtttgcaa ttcgcagctg cttaacgaaa gtcaaattat cggtaccttt gagctgcagg  10740
gtccctcgcc tgacgaaaag tccgcggctc cggggttgaa actcactccg gggctgtgga  10800
cgtcggctta ccttcgcaaa tttgtacctg aggactacca cgcccacgag attaggttct  10860
acgaagacca atcccgcccg ccaaatgcgg agcttaccgc ctgcgtcatt acccagggcc  10920
acattcttgg ccaattgcaa gccatcaaca aagcccgcca agagttttctg ctacgaaagg  10980
gacgggggt ttacttggac ccccagtccg gcgaggagc caacccaatc ccccgccgc    11040
cgcagcccta tcagcagcag ccgcgggccc ttgcttccca ggatggcacc caaaaagaag  11100
ctgcagctgc cgccgccacc cacggacgag gaggaatact gggacagtca ggcagaggag  11160
gttttggacg aggaggagga ggacatgatg gaagactggg agagcctaga cgaggaagct  11220
tccgaggtcg aagaggtgtc agacgaaaca ccgtcaccct cggtcgcatt ccctctcccg  11280
gcgccccaga aatcggcaac cggttccagc atggctacaa cctccgctcc tcaggcgccg  11340
ccggcactgc ccgttcgccg acccaaccgt agatgggaca ccactggaac cagggccggt  11400
aagtccaagc agccgccgcc gttagcccaa gagcaacaac agcgccaagg ctaccgctca  11460
tggcgcgggc acaagaacgc catagttgct tgcttgcaag actgtggggg caacatctcc  11520
ttcgcccgcc gctttcttct ctaccatcac ggcgtggcct tccccgtaa catcctgcat   11580
tactaccgtc atctctacag cccatactgc accggcggca gcggcagcgg cagcaacagc  11640
agcggccaca cagaagcaaa ggcgaccgga tagcaagact ctgacaaagc ccaagaaatc  11700
```

```
cacagcggcg gcagcagcag gaggaggagc gctgcgtctg gcgcccaacg aacccgtatc   11760
gacccgcgag cttagaaaca ggattttttcc cactctgtat gctatatttc aacagagcag   11820
gggccaagaa caagagctga aaataaaaaa caggtctctg cgatccctca cccgcagctg   11880
cctgtatcac aaaagcgaag atcagcttcg gcgcacgctg gaagacgcgg aggctctctt   11940
cagtaaatac tgcgcgctga ctcttaagga ctagtttcgc gccctttctc aaatttaagc   12000
gcgaaaacta cgtcatctcc agcggccaca cccggcgcca gcacctgtcg tcagcgccat   12060
tatgagcaag gaaattccca cgccctacat gtggagttac cagccacaaa tgggacttgc   12120
ggctggagct gcccaagact actcaacccg aataaactac atgagcgcgg accccacat    12180 gatatcccgg gtcaacggaa tccgcgccca ccgaaaccga attctcttgg aacaggcggc   12240
tattaccacc acacctcgta ataaccttaa tccccgtagt tggcccgctg ccctggtgta   12300
ccaggaaagt cccgctccca ccactgtggt acttcccaga gacgcccagg ccgaagttca   12360
gatgactaac tcaggggcgc agcttgcggg cggctttcgt cacagggtgc ggtcgcccgg   12420
gcagggtata actcacctga caatcagagg gcgaggtatt cagctcaacg acgagtcggt   12480
gagctcctcg cttggtctcc gtccggacgg gacatttcag atcggcggcg ccggccgtcc   12540
ttcattcacg cctcgtcagg caatcctaac tctgcagacc tcgtcctctg agccgcgctc   12600
tggaggcatt ggaactctgc aatttattga ggagtttgtg ccatcggtct actttaaccc   12660
cttctcggga cctcccggcc actatccgga tcaatttatt cctaactttg acgcggtaaa   12720
ggactcggcg gacggctacg actgaatgtt aagtggagag gcagagcaac tgcgcctgaa   12780
acacctggtc cactgtcgcc gccacaagtg cttttgcccgc gactccggtg agttttgcta   12840
ctttgaattg cccgaggatc atatcgaggg cccggcgcac ggcgtccggc ttaccgccca   12900
gggagagctt gcccgtagcc tgattcggga gtttacccag cgcccctgc tagttgagcg    12960 ggacaggga ccctgtgttc tcactgtgat ttgcaactgt cctaaccttg gattacatca     13020
agatcctcta gttaattaac tagagtaccc ggggatctta ttccctttaa ctaataaaaa    13080
aaaataataa agcatcactt acttaaaatc agttagcaaa tttctgtcca gtttattcag   13140
cagcacctcc ttgccctcct cccagctctg gtattgcagc ttcctcctgg ctgcaaactt   13200
tctccacaat ctaaatggaa tgtcagtttc ctcctgttcc tgtccatccg cacccactat   13260
cttcatgttg ttgcagatga agcgcgcaag accgtctgaa gataccttca accccgtgta   13320
tccatatgac acgaaaccg gtcctccaac tgtgcctttt cttactcctc cctttgtatc    13380
ccccaatggg tttcaagaga gtccccctgg ggtactctct ttgcgcctat ccgaaccttct  13440 agttacctcc aatggcatgc ttgcgctcaa aatgggcaac ggcctctctc tggacgaggc   13500
cggcaacctt acctcccaaa atgtaaccac tgtgagccca cctctcaaaa aaaccaagtc   13560
aaacataaac ctggaaatat ctgcacccct cacagttacc tcagaagccc taactgtggc   13620
tgccgccgca cctctaatgg tcgcgggcaa cacactcacc atgcaatcac aggcccccgct  13680 aaccgtgcac gactccaaac ttagcattgc cacccaagga cccctcacag tgtcagaagg   13740
aaagctagcc ctgcaaacat caggccccct caccaccacc gatagcagta cccttactat   13800
cactgcctca cccctctaa ctactgccac tggtagcttg ggcattgact tgaaagagcc    13860
catttataca caaaatggaa aactaggact aaagtacggg gctccttgc atgtaacaga    13920 cgacctaaac actttgaccg tagcaactgg tccaggtgtg actattaata atacttcctt   13980
gcaaactaaa gttactggag ccttgggttt tgattcacaa ggcaatatgc aacttaatgt   14040
agcaggagga ctaaggattg attctcaaaa cagacgcctt atacttgatg ttagttatcc   14100
```

-continued

```
gtttgatgct caaaaccaac taaatctaag actaggacag ggccctcttt ttataaactc   14160
agcccacaac ttggatatta actacaacaa aggcctttac ttgtttacag cttcaaacaa   14220
ttccaaaaag cttgaggtta acctaagcac tgccaagggg ttgatgtttg acgctacagc   14280
catagccatt aatgcaggag atgggcttga atttggttca cctaatgcac caaacacaaa   14340
tcccctcaaa acaaaaattg gccatggcct agaatttgat tcaaacaagg ctatggttcc   14400
taaactagga actggcctta gttttgacag cacaggtgcc attacagtag aaacaaaaa    14460
taatgataag ctaactttgt ggaccacacc agctccatct cctaactgta gactaaatgc   14520
agagaaagat gctaaactca ctttggtctt aacaaaatgt ggcagtcaaa tacttgctac   14580
agtttcagtt ttggctgtta aaggcagttt ggctccaata tctggaacag ttcaaagtgc   14640
tcatcttatt ataagatttg acgaaaatgg agtgctacta acaattcct tcctggaccc    14700
agaatattgg aactttagaa atggagatct tactgaaggc acagcctata caaacgctgt   14760
tggatttatg cctaacctat cagcttatcc aaaatctcac ggtaaaactg ccaaaagtaa   14820
cattgtcagt caagtttact aaacggaga caaaactaaa cctgtaacac taaccattac    14880
actaaacggt acacaggaaa caggagacac aactccaagt gcatactcta tgtcattttc   14940
atgggactgg tctggccaca actacattaa tgaaatattt gccacatcct cttacacttt   15000
ttcatacatt gcccaagaat aaagaatcgt ttgtgttatg tttcaacgtg tttatttttc   15060
aattgcagaa aatttcaagt catttttcat tcagtagtat agccccacca ccacatagct   15120
tatacagatc accgtacctt aatcaaactc acagaaccct agtattcaac ctgccacctc   15180
cctcccaaca cacagagtac acagtccttt ctccccggct ggccttaaaa agcatcatat   15240
catgggtaac agacatattc ttaggtgtta tattccacac ggtttcctgt cgagccaaac   15300
gctcatcagt gatattaata aactccccgg gcagctcact taagttcatg tcgctgtcca   15360
gctgctgagc cacaggctgc tgtccaactt gcggttgctt aacgggcggc gaaggagaag   15420
tccacgccta catgggggta gagtcataat cgtgcatcag gataggcgg tggtgctgca     15480
gcagcgcgcg aataaactgc tgccgccgcc gctccgtcct gcaggaatac aacatggcag   15540
tggtctcctc agcgatgatt cgcaccgccc gcagcataag gcgccttgtc ctccgggcac   15600
agcagcgcac cctgatctca cttaaatcag cacagtaact gcagcacagc accacaatat   15660
tgttcaaaat cccacagtgc aaggcgctgt atccaaagct catggcgggg accacagaac   15720
ccacgtggcc atcataccac aagcgcaggt agattaagtg gcgacccctc ataaacacgc   15780
tggacataaa cattacctct tttgcatgt tgtaattcac cacctcccgg taccatataa     15840
acctctgatt aaacatggcg ccatccacca ccatcctaaa ccagctggcc aaaacctgcc   15900
cgccggctat acactgcagg gaaccgggac tggaacaatg acagtggaga gcccaggact   15960
cgtaaccatg gatcatcatg ctcgtcatga tatcaatgtt ggcacaacac aggcacacgt   16020
gcatacactt cctcaggatt acaagctcct cccgcgttag aaccatatcc cagggaacaa   16080
cccattcctg aatcagcgta aatcccacac tgcaggaag acctcgcacg taactcacgt     16140
tgtgcattgt caaagtgtta cattcgggca gcagcggatg atcctccagt atggtagcgc   16200
gggtttctgt ctcaaaagga ggtagacgat ccctactgta cggagtgcgc cgagacaacc   16260
gagatcgtgt tggtcgtagt gtcatgccaa atggaacgcc ggacgtagtc atatttcctg   16320
aagcaaaacc aggtgcgggc gtgacaaaca gatctgcgtc tccggtctcg ccgcttagat   16380
cgctctgtgt agtagttgta gtatatccac tctctcaaag catccaggcg cccccctggct 16440
tcgggttcta tgtaaactcc ttcatgcgcc gctgccctga taacatccac caccgcagaa   16500
```

```
taagccacac ccagccaacc tacacattcg ttctgcgagt cacacacggg aggagcggga   16560
agagctggaa gaaccatgtt ttttttttta ttccaaaaga ttatccaaaa cctcaaaatg   16620
aagatctatt aagtgaacgc gctcccctcc ggtggcgtgg tcaaactcta cagccaaaga   16680
acagataatg gcatttgtaa gatgttgcac aatggcttcc aaaaggcaaa cggccctcac   16740
gtccaagtgg acgtaaaggc taaacccttc agggtgaatc tcctctataa acattccagc   16800
accttcaacc atgcccaaat aattctcatc tcgccacctt ctcaatatat ctctaagcaa   16860
atcccgaata ttaagtccgg ccattgtaaa aatctgctcc agagcgccct ccaccttcag   16920
cctcaagcag cgaatcatga ttgcaaaaat tcaggttcct cacagacctg tataagattc   16980
aaaagcggaa cattaacaaa ataccgcga tcccgtaggt cccttcgcag ggccagctga    17040
acataatcgt gcaggtctgc acggaccagc gcggccactt ccccgccagg aaccttgaca   17100
aaagaaccca cactgattat gacacgcata ctcggagcta tgctaaccag cgtagccccg   17160
atgtaagctt tgttgcatgg gcggcgatat aaaatgcaag gtgctgctca aaaaatcagg   17220
caaagcctcg cgcaaaaaag aaagcacatc gtagtcatgc tcatgcagat aaaggcaggt   17280
aagctccgga accaccacag aaaaagacac catttttctc tcaaacatgt ctgcgggttt   17340
ctgcataaac acaaaataaa ataacaaaaa acatttaaaa cattagaagc ctgtcttaca   17400
acaggaaaaa caaccttat aagcataaga cggactacgg ccatgccggc gtgaccgtaa    17460
aaaaactggt caccgtgatt aaaaagcacc accgacagct cctcggtcat gtccggagtc   17520
ataatgtaag actcggtaaa cacatcaggt tgattcatcg gtcagtgcta aaaagcgacc   17580
gaaatagccc gggggaatac ataccccgcag gcgtagagac aacattacag cccccatagg   17640
aggtataaca aaattaatag gagagaaaaa cacataaaca cctgaaaaac cctcctgcct   17700
aggcaaaata gcaccctccc gctccagaac aacatacagc gcttcacagc ggcagcctaa   17760
cagtcagcct taccagtaaa aaagaaaacc tattaaaaaa acaccactcg acacggcacc   17820
agctcaatca gtcacagtgt aaaaaagggc caagtgcaga gcgagtatat ataggactaa   17880
aaaatgacgt aacggttaaa gtccacaaaa acacccagaa aaccgcacg cgaacctacg    17940 cccagaaacg aaagccaaaa aacccacaac ttcctcaaat cgtcacttcc gttttcccac   18000
gttacgtaac ttcccatttt aagaaaacta caattcccaa cacatacaag ttactccgcc   18060
ctaaaaccta cgtcacccgc cccgttccca cgccccgcgc cacgtcacaa actccacccc   18120
ctcattatca tattggcttc aatccaaaat aaggtatatt attgatgatt tattttggat   18180
tgaagccaat atgataatga gggggtggag tttgtgacgt ggcgcggggc gtgggaacgg   18240
ggcgggtgac gtagtagtgt ggcggaagtg tgatgttgca agtgtggcgg aacacatgta   18300
agcgacggat gtggcaaaag tgacgttttt ggtgtgcgcc ggatccacag gacgggtgtg   18360
gtcgccatga tcgcgtagtc gatagtggct ccaagtagcg aagcgagcag gactgggcgg   18420
cggccaaagc ggtcggacag tgctccgaga acgggtgcgc atagaaattg catcaacgca   18480
tatagcgcta gcagcacgcc atagtgactg gcgatgctgt cggaatggac gatatcccgc   18540
aagaggcccg gcagtaccgg cataaccaag cctatgccta cagcatccag ggtgacggta   18600
ccgaggatga cgatgagcgc attgttagat ttcatacacg gtgcctgact gcgttagcaa   18660
tttaactgtg ataaactacc gcattaaagc ttatcgaatt cgtaatcatg gtcatagctg   18720
tttcctgtgt gaaattgtta tccgctcaca attccacaca acatacgagc cggaagcata   18780
aagtgtaaag cctggggtgc ctaatgagtg agctaactca cattaattgc gttgcgctca   18840
```

-continued

```
ctgcccgctt tccagtcggg aaacctgtcg tgccagctgc attaatgaat cggccaacgc    18900
gcggggagag gcggtttgcg tattgggcgc                                     18930
```

<210> SEQ ID NO 9
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 9

```
tcccatagta acgccaatag g                                              21
```

<210> SEQ ID NO 10
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 10

```
cttggcatat gatacacttg atg                                            23
```

<210> SEQ ID NO 11
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 11

```
atggaaacat tctcggccac aagc                                           24
```

<210> SEQ ID NO 12
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 12

```
tcgccgattg gagtgttctg ttg                                            23
```

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13

```
ggacggcgag ttcatctaca                                                20
```

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14

```
ttgacctcag cgtcgtagtg                                                20
```

```
<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
ggctgatgtc aggagggata                                                     20

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 16
gggacagtga atccggaaag                                                     20

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
aagtcgtgca gcaggatatg                                                     20
```

METHODS OF PACKAGING MULTIPLE ADENO-ASSOCIATED VIRUS VECTORS

CROSS-REFERENCED TO RELATED APPLICATIONS

This application is a national stage filing under 35 U.S.C. § 371 of International PCT application PCT/US2015/036841, filed Jun. 20, 2015 which claims the benefit under 35 U.S.C. § 119(e) of U.S. provisional application No. 62/015,031, filed Jun. 20, 2014, all of which are incorporated by reference herein in their entirety.

FEDERALLY SPONSORED RESEARCH OR DEVELOPMENT

This invention was made with government support under HL059412 awarded by the National Institutes of Health. The government has certain rights in the invention.

BACKGROUND OF THE INVENTION

Recombinant adeno-associated virus (rAAV) particles are a promising method for therapeutic gene delivery to treat a multitude of diseases. In some cases, use of multiple rAAV particles, as a mixed population, is desirable. For example, it may be that the transgene is too large to be effectively packaged into a single rAAV particle, such that two rAAV particles must be used to package the entire transgene. Alternatively, multiple transgenes may be required for effective treatment, for instance if multiple proteins are involved in disease progression. Further, it may be desirable to use multiple promoters to target different tissues. For these reasons, mixed populations of rAAV particles may be appropriate for certain types of gene therapy. Unfortunately, hurdles still exist for rapidly and cost-effectively producing mixed populations of rAAV particles.

SUMMARY OF THE INVENTION

Aspects of the disclosure are based, in part, on the development of an efficient and inexpensive method of co-packaging of multiple plasmids containing different expression cassettes using a single transfection step to produce preparations of recombinant adeno-associated virus (rAAV) particles containing a desired ratio of the different expression cassette plasmids. It was found that two plasmids, either encoding different transgenes or encoding the same transgenes but under the control of different promoters, could be transfected simultaneously into cells at several ratios. It was surprisingly found that the transduced cells produced a mixed population of rAAV particles having a ratio that was approximately the same as the input ratio of the two plasmids at the transfection step. This study showed that mixed rAAV particle preparations containing rAAV particles encapsidating different nucleic acid molecules could be prepared using a single step for introducing the plasmids into producer cells.

Accordingly, aspects of the disclosure relate to methods of co-packaging rAAV particles.

Some aspects of the disclosure relate to methods of producing a recombinant adeno-associated virus rAAV particle preparation having a target ratio of at least a first rAAV particle to a second rAAV particle (e.g., a target ratio of a first rAAV particle to a second rAAV particle, or a target ratio of a first rAAV particle to a second rAAV particle to a third rAAV particle, or a target ratio of a first rAAV particle to a second rAAV particle to a third rAAV particle to a fourth rAAV particle, etc.), the method comprising
(a) contacting a cell preparation with
  (i) at least two (e.g., two, three, four, five, or more) nucleic acid vectors described herein (e.g., each containing a construct comprising a heterologous nucleic acid region encoding a protein or polypeptide or an RNA and nucleic acid regions comprising an inverted terminal repeat (ITR) flanking each side of the heterologous nucleic acid region);
  wherein the cell preparation is contacted under conditions sufficient for producing at least two (e.g., two, three, four, five, or more) rAAV particles comprising the constructs of the at least two (e.g., two, three, four, five, or more) nucleic acid vectors; and
(b) isolating the at least two (e.g., two, three, four, five, or more) rAAV particles from the cell preparation, thereby producing a rAAV preparation having a target ratio of the at least two (e.g., two, three, four, five, or more) rAAV particles.

In some embodiments, a method of producing a recombinant adeno-associated virus (rAAV) particle preparation having a target ratio of a first rAAV particle to a second rAAV particle is provided, the method comprising:
(a) contacting a cell preparation with:
  (i) a first nucleic acid vector containing a first construct comprising a heterologous nucleic acid region encoding a first protein or polypeptide and nucleic acid regions comprising an inverted terminal repeat (ITR) flanking each side of the heterologous nucleic acid region;
  (ii) a second nucleic acid vector containing a second construct comprising a heterologous nucleic acid region encoding a second protein or polypeptide and nucleic acid regions comprising an inverted terminal repeat (ITR) flanking each side of the heterologous nucleic acid region,
  wherein the cell preparation is contacted under conditions sufficient for producing a first rAAV particle comprising the first construct and a second rAAV particle comprising the second construct; and
(b) isolating the first rAAV particle and the second rAAV particle from the cell preparation, thereby producing a rAAV preparation having a target ratio of the first rAAV particle to the second rAAV particle.

In some embodiments, the cell preparation is contacted simultaneously with the first nucleic acid vector and the second nucleic acid vector. In some embodiments, the first nucleic acid vector and the second nucleic acid vector are present in an initial ratio of the first nucleic acid vector to the second nucleic acid vector when contacted with the cell preparation. In some embodiments, the target ratio of the first rAAV particle and the second rAAV particle is compared to the initial ratio of the first nucleic acid vector to the second nucleic acid vector. In some embodiments, the target ratio of the first rAAV particle to the second rAAV particle is within 10% of the initial ratio of the first nucleic acid vector to the second nucleic acid vector. In some embodiments, the initial ratio is 1:1, 1:9 or 9:1 of the first nucleic acid vector to the second nucleic acid vector. In some embodiments, the target ratio of the first rAAV particle to the second rAAV particle is measured after isolating the first rAAV particle and the second rAAV particle from the cell preparation. In some embodiments, the target ratio of the first rAAV particle to the second rAAV particle is measured by measuring a level of DNA from the first rAAV particle and a level of DNA from the second rAAV particle. In some embodiments, the level of DNA is measured using PCR, sequencing or flow cytometry. In some embodiments, the level of DNA is measured using PCR and the PCR is quantitative PCR.

In some embodiments of any one of the methods described herein, step (a) comprises transfecting the cell preparation with the first nucleic acid vector and the second nucleic acid vector. In some embodiments, the first nucleic acid vector and the second nucleic acid vector are a first plasmid and a second plasmid. In some embodiments, the method further comprises contacting the cell preparation with at least one helper plasmid. In some embodiments, the at least one helper plasmid is a first helper plasmid comprising a rep gene and a cap gene and a second helper plasmid comprising a E1a gene, a E1b gene, a E4 gene, a E2a gene, and a VA gene.

In some embodiments of any one of the methods described herein, step (a) comprises infecting the cell preparation with the first nucleic acid vector and the second nucleic acid vector. In some embodiments, the first nucleic acid vector is contained within a first herpes simplex virus type 1 (HSV) particle and the second nucleic acid vector is contained within a second HSV particle. In some embodiments, the first nucleic acid vector is contained within a first baculovirus particle and the second nucleic acid vector is contained within a second baculovirus particle.

In some embodiments of any one of the methods described herein, step (a) comprises incubating the cell preparation for at least 60 hours after contacting the cell preparation with the first nucleic acid vector and the second nucleic acid vector.

In some embodiments of any one of the methods described herein, step (b) comprises lysing the cell preparation and extracting the first rAAV particle and the second rAAV particle. In some embodiments, the first rAAV particle and the second rAAV particle are extracted simultaneously.

In some embodiments, two or more vectors are provided in a ratio of interest (e.g., a specified ratio or range of ratios) to produce different rAAVs in the cell preparation, and a preparation of the different rAAV particles is prepared from the cell preparation. In some embodiments, the different rAAV particles are isolated together (e.g., using an isolation procedure that isolates a mixture of the different rAAV particles).

In some embodiments, a preparation of two rAAV particles described herein can be used to deliver different genes, different gene fragments (e.g., different regions of the same gene or different genes), with or without promoters, and/or with or without other regulatory nucleic acid sequences to a cell (e.g., in vitro or in a subject). In some embodiments, the genes or gene fragments are human genes. In some embodiments, a protein or polypeptide encoded by a nucleic acid described herein is a full length protein or polypeptide. In some embodiments, a protein or polypeptide encoded by a nucleic acid described herein is a fragment of a full length protein or polypeptide (e.g., a functional fragment). In some embodiments, the nucleic acids (e.g., genes or gene fragments) are recombinant nucleic acids (e.g., recombinant genes). In some embodiments, the genes or gene fragments are used for gene rescue. In some embodiments, the genes or gene fragments are used to provide one or more RNAs or proteins to a cell or a subject. In some embodiments, the one or more RNAs or proteins are therapeutic RNAs or proteins (e.g., they encode a naturally occurring or recombinant enzyme, cytokine, receptor, kinase, regulatory protein, ligand, antibody, or other RNA or protein that is useful to assist in the treatment of a disease or condition). In some embodiments, a preparation of rAAV particles are delivered to a subject (e.g., a human subject) for example via injection or other delivery route. In some embodiments, the subject is a subject having a disease or condition that can be treated with the one or more nucleic acids that are delivered using the rAAV particles. In some embodiments, a preparation of rAAV particles are contacted to a preparation of cells in vitro. In some embodiments, the cells are cells from a subject (e.g., isolated from a human subject) and the cells are administered (e.g., re-administered to the human subject) after being modified by the nucleic acids in the rAAV particles (e.g., after genome editing or after receiving one or more constructs that express an RNA or protein of interest such as a therapeutic RNA or protein).

In some embodiments of any one of the methods described herein, the first rAAV particle and the second rAAV particle are each rAAV 2/9 pseudotyped particles. In some embodiments of any one of the methods described herein, more than two rAAV particles are each rAAV 2/9 pseudotyped particles.

The details of one or more embodiments of the disclosure are set forth in the description below. Other features or advantages of the present disclosure will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 5A) AAV9-LSP-coGAA and AAV9-DES-coGAA were co-packaged and purified at 1:9 (lanes 1, 4 and 7), 1:1 (lanes 2, 5 and 8) and 9:1 ratios (lanes 3, 6 and 9), respectively. AAV9-LSP-coGAA band is 288 bp and AAV9-DES-coGAA is 453 bp. DNA was amplified from each preparation and ran on 1.5% agarose gel.

DETAILED DESCRIPTION OF THE INVENTION

Figure 1:
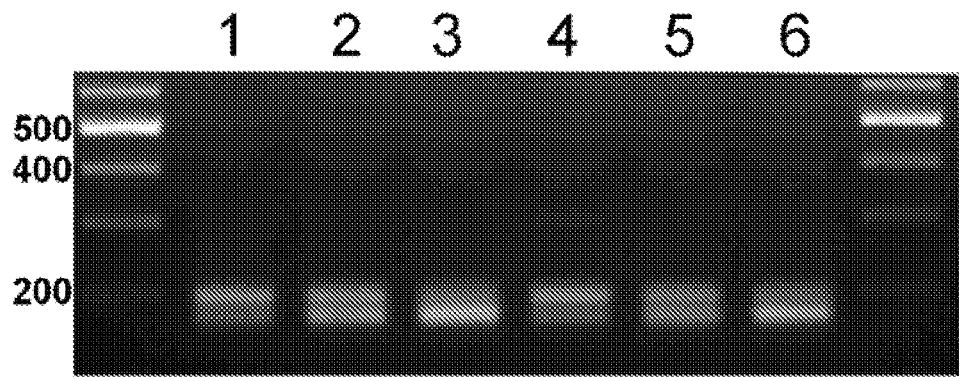
FIG. 1 is a photograph of a DNA gel showing differential packaging of expression cassettes combined prior to transfection. The vectors contained different transgenes which were used for delineation. DNA was amplified from each preparation and ran on 2% agarose gel. GFP band is 171 bp and mCherry is 191 bp. Lanes 1-3 contain DNA amplified from vectors in crude lysate (post-benzonase treatment); lanes 4-6 contain DNA amplified from vectors purified via iodixanol gradient originating from the crude lysates in lanes 1-3. Vector constructs were co-packaged in AAV9 at ratios of GFP to mCherry 1:9, 1:1 and 9:1, respectively. Gel is one representative image of three separate co-packaging experiments.

Limiting factors in large pre-clinical and clinical studies utilizing adeno-associated virus (AAV) particles for gene therapy are focused on the restrictive packaging capacity, the overall yields and the versatility of the production methods for single AAV vector production. Furthermore, applications where multiple vectors are needed to provide long expression cassettes, whether due to long cDNA sequences or the need of different regulatory elements, require that each vector be packaged and characterized separately, directly affecting labor and cost associated with such manufacturing strategies.

As described herein, a rapid and inexpensive method was devised for co-packaging multiple expression constructs encoding different proteins or encoded the same proteins with different promoters into multiple recombinant adeno-associated virus (rAAV) particles, to produce a mixed population of rAAV particles. It was surprisingly found that the input ratio of two plasmids containing two different expression constructs correlated well with the output ratio of rAAV particles containing the two different expression constructs, demonstrating that the method could be used to reliably predict output ratios of rAAV particles based on the initial ratio of plasmids. This study showed feasibility and reproducibility of a method that allows for two constructs, differing in either transgene or control elements, to be efficiently co-packaged and characterized simultaneously, reducing time and cost of manufacturing and release testing.

Accordingly, aspects of the disclosure relate to methods of producing a recombinant adeno-associated virus rAAV particle preparation having a target ratio of at least a first rAAV particle to a second rAAV particle (e.g., a target ratio of a first rAAV particle to a second rAAV particle, or a target ratio of a first rAAV particle to a second rAAV particle to a third rAAV particle to a fourth rAAV particle, etc.), the method comprising
(a) contacting a cell preparation with
(i) at least two (e.g., two, three, four, five, or more) nucleic acid vectors described herein (e.g., each containing a construct comprising a heterologous nucleic acid region encoding a protein or polypeptide or an RNA and nucleic acid regions comprising an inverted terminal repeat (ITR) flanking each side of the heterologous nucleic acid region);
wherein the cell preparation is contacted under conditions sufficient for producing at least two (e.g., two, three, four, five, or more) rAAV particles comprising the constructs of the at least two (e.g., two, three, four, five, or more) nucleic acid vectors; and
(b) isolating the at least two (e.g., two, three, four, five, or more) rAAV particles from the cell preparation, thereby producing a rAAV preparation having a target ratio of the at least two (e.g., two, three, four, five, or more) rAAV particles.

In some embodiments, the method comprises:
(a) contacting a cell preparation with
(i) a first nucleic acid vector described herein (e.g., containing a first construct comprising a heterologous nucleic acid region encoding a first protein or polypeptide and nucleic acid regions comprising an inverted terminal repeat (ITR) flanking each side of the heterologous nucleic acid region);
(ii) a second nucleic acid vector described herein (e.g., containing a second construct comprising a heterologous nucleic acid region encoding a second protein or polypeptide and nucleic acid regions comprising an inverted terminal repeat (ITR) flanking each side of the heterologous nucleic acid region),
wherein the cell preparation is contacted under conditions sufficient for producing a first rAAV particle comprising the first construct and a second rAAV particle comprising the second construct; and
(b) isolating the first rAAV particle and the second rAAV particle from the cell preparation, thereby producing a rAAV preparation having a target ratio of the first rAAV particle to the second rAAV particle.

In some embodiments, the method comprises:
(a) contacting a cell preparation with
(i) a first nucleic acid vector described herein (e.g., containing a first construct comprising a heterologous nucleic acid region encoding a first protein or polypeptide or RNA and nucleic acid regions comprising an inverted terminal repeat (ITR) flanking each side of the heterologous nucleic acid region);
(ii) a second nucleic acid vector described herein (e.g., containing a second construct comprising a heterologous nucleic acid region encoding a second protein or polypeptide or RNA and nucleic acid regions comprising an inverted terminal repeat (ITR) flanking each side of the heterologous nucleic acid region),
(iii) a third nucleic acid vector described herein (e.g., containing a third construct comprising a heterologous nucleic acid region encoding a third protein or polypeptide or RNA and nucleic acid regions comprising an inverted terminal repeat (ITR) flanking each side of the heterologous nucleic acid region), wherein the cell preparation is contacted under conditions sufficient for producing a first rAAV particle comprising the first construct, a second rAAV particle comprising the second construct, and a third rAAV particle comprising the third construct; and (b) isolating the first rAAV particle, the second rAAV particle, and the third rAAV particle from the cell preparation, thereby producing a rAAV preparation having a target ratio of the first rAAV particle to the second rAAV particle to the third rAAV particle.

In some embodiments, the method comprises:
(a) contacting a cell preparation with
  (i) a first nucleic acid vector described herein (e.g., containing a first construct comprising a heterologous nucleic acid region encoding a first protein or polypeptide or RNA and nucleic acid regions comprising an inverted terminal repeat (ITR) flanking each side of the heterologous nucleic acid region);
  (ii) a second nucleic acid vector described herein (e.g., containing a second construct comprising a heterologous nucleic acid region encoding a second protein or polypeptide or RNA and nucleic acid regions comprising an inverted terminal repeat (ITR) flanking each side of the heterologous nucleic acid region),
  (iii) a third nucleic acid vector described herein (e.g., containing a third construct comprising a heterologous nucleic acid region encoding a third protein or polypeptide or RNA and nucleic acid regions comprising an inverted terminal repeat (ITR) flanking each side of the heterologous nucleic acid region),
  (iv) a fourth nucleic acid vector described herein (e.g., containing a fourth construct comprising a heterologous nucleic acid region encoding a fourth protein or polypeptide or RNA and nucleic acid regions comprising an inverted terminal repeat (ITR) flanking each side of the heterologous nucleic acid region),
wherein the cell preparation is contacted under conditions sufficient for producing a first rAAV particle comprising the first construct, a second rAAV particle comprising the second construct, a third rAAV particle comprising the third construct, and a fourth rAAV particle comprising the fourth construct; and (b) isolating the first rAAV particle, the second rAAV particle, the third rAAV particle, and the fourth rAAV particle from the cell preparation, thereby producing a rAAV preparation having a target ratio of the first rAAV particle to the second rAAV particle to the third rAAV particle to the fourth rAAV particle.

Ratios

In some embodiments, the first nucleic acid vector and the second nucleic acid vector are present in an initial ratio of the first nucleic acid vector to the second nucleic acid vector when contacted with the cell preparation. In some embodiments, the initial ratio is determined by adding a known concentration of the first nucleic acid vector and a known concentration of the second nucleic acid vector to a composition and contacting the composition with the cell preparation. In some embodiments, the initial ratio is determined by measuring the concentration of the first nucleic acid vector and the second nucleic acid vector, e.g., when present together in a composition. The measuring may be done using any method known in the art, e.g., by PCR.

The initial ratio of the first nucleic acid vector to the second nucleic acid vector (and optionally third nucleic acid vector, fourth nucleic acid vector, etc.) may be any ratio that is suitable for obtaining a desired target ratio. The target ratio will depend upon the disease to be treated, the proteins or polypeptides to be delivered, the tissue(s) to be targeted, the promoter to be used, the size of nucleic acid vectors and other such considerations within the knowledge of the person skilled in the art. In some embodiments, if the sizes of the nucleic acid vectors are not approximately equal, the ratios may be adjusted to compensate for differences in packaging efficiency. For example, the molar ratios of the nucleic acid vectors may be adjusted to produce equimolar input ratios that result in appropriate ratios of output rAAV particles, as smaller vectors, e.g., of about 4.2-4.7 kb in size, are generally packaged more abundantly. In some embodiments, for instance, if one nucleic acid vector (e.g., pTR-X plasmid) is ¾ the size of the other nucleic acid vector (e.g., pTR-Y plasmid), then the amount of pTR-Y may be increased to compensate for the size difference between the two vectors. An exemplary calculation for determining molar ratio is shown below:

$$\frac{\text{Amount of } pTR\text{-}X(ng) \times \text{Size of } pTR\text{-}Y(bp)}{\text{Size of } pTR\text{-}X(bp)} \times \frac{1}{1} =$$

Amount of $pTR\text{-}Y$ to add for 1:1 molar ratio

Calculating and producing equimolar ratios of nucleic acid vectors, e.g., upon transfection, can be done using routine techniques. In some embodiments, the initial ratio (e.g., initial molar ratio) is 1:1, 1:2, 1:3, 1:4, 1:5, 1:6, 1:7, 1:8, 1:9, 1:10, 1:20, 1:30, 1:40, 1:50, 1:60, 1:70, 1:80, 1:90 or 1:100 (or any ratio in between 1:1 and 1:100) of the first nucleic acid vector to the second nucleic acid vector. In some embodiments, if more than two nucleic acid vectors (e.g., three or four nucleic acid vectors) are utilized, then the initial ratio is, for example, 1:1:1, 1:1:1:1, 1:2:2, 1:2:2:1, 1:2:2:2, 1:2:3, 1:2:3:4, 1:2:1, 1:2:1:2, 1:2:1:1 (or any ratio between 1:1:1 and 1:100:100 or between 1:1:1:1 and 1:100:100:100) of the more than two nucleic acid vectors. It should be appreciated the ratio of any two particular nucleic acid vectors can be different (e.g., 1:2 or 1:2:3 or 1:2:1:2). In some embodiments, the target ratio is 1:1, 1:2, 1:3, 1:4, 1:5, 1:6, 1:7, 1:8, 1:9, 1:10, 1:20, 1:30, 1:40, 1:50, 1:60, 1:70, 1:80, 1:90 or 1:100 (or any ratio in between 1:1 and 1:100) of the first rAAV particle to the second rAAV particle. In some embodiments, if more than two nucleic acid vectors (e.g., three or four nucleic acid vectors) are utilized, then the target ratio is, for example, 1:1:1, 1:1:1:1, 1:2:2, 1:2:2:1, 1:2:2:2, 1:2:3, 1:2:3:4, 1:2:1, 1:2:1:2, 1:2:1:1 (or any ratio between 1:1:1 and 1:100:100 or between 1:1:1:1 and 1:100:100:100) of the more than two rAAV particles (e.g., three or four rAAV particles). However, it should be appreciated that any initial ratio of interest between two or more vectors or constructs can be used.

In some embodiments, the target ratio is compared to the initial ratio. In some embodiments, the target ratio of the first rAAV particle to the second rAAV particle is compared to the initial ratio of the first nucleic acid vector to the second nucleic acid vector. The comparison may be done, e.g., with the assistance of software on a computer. In some embodiments, the target ratio is within a certain percentage of the initial ratio. In some embodiments, the target ratio is within 20%, 15%, 10%, 9%, 8%, 7%, 6%, 5%, 4%, 3%, 2%, or 1% of the initial ratio. In some embodiments, the target ratio of the first rAAV particle to the second rAAV particle is within a certain percentage of the initial ratio of the first nucleic acid vector to the second nucleic acid vector. In some embodiments, the target ratio of the first rAAV particle to the second rAAV particle is within 20%, 15%, 10%, 9%, 8%, 7%, 6%, 5%, 4%, 3%, 2%, or 1% of the initial ratio of the first nucleic acid vector to the second nucleic acid vector. The percentage may be determined, e.g., by comparing the amount of the first rAAV particle and the second rAAV particle in the rAAV preparation. In some embodiments, the target ratio is within 0-20%, 0-15%, 0-10%, 0-9%, 0-8%, 0-7%, 0-6%, 0-5%, 1-10%, 1-9%, 1-8%, 1-7%, 1-6%, 1-5%, 2-10%, 2-9%, 2-8%, 2-7%, 2-6%, 2-5%, 3-10%, 3-9%, 3-8%, 3-7%, 3-6%, or 3-5% of the initial ratio. In some embodiments, the target ratio of the first rAAV particle to the second rAAV particle is within 0-20%, 0-15%, 0-10%, 0-9%, 0-8%, 0-7%, 0-6%, 0-5%, 1-10%, 1-9%, 1-8%, 1-7%, 1-6%, 1-5%, 2-10%, 2-9%, 2-8%, 2-7%, 2-6%, 2-5%, 3-10%, 3-9%, 3-8%, 3-7%, 3-6%, or 3-5% of the initial ratio of the first nucleic acid vector to the second nucleic acid vector.

In some embodiments, the initial ratio and/or the target ratio are measured. The initial and/or target ratio may be measured using any method known in the art or described herein (see, e.g., Current Protocols in Molecular Biology, Wiley Intersciences), e.g., using a DNA-detection assay (e.g., PCR, sequencing, or probes), a protein detection assay (e.g., Western blot, silver stain, coomassie stain, immunohistochemistry, flow cytometry or immunofluorescence), or a virus infectivity assay (e.g., a green cell assay). A PCR assay may be any type of PCR known in the art including, but not limited to quantitative PCR. A sequencing assay may be any type of sequencing known in the art including, Sanger sequencing or massive parallel sequencing (e.g., Ion Torrent, pyrosequencing, sequencing by synthesis, and sequencing by ligation). In some embodiments, the target ratio of the first rAAV particle to the second rAAV particle is measured after isolating the first rAAV particle and the second rAAV particle from the cell preparation. In some embodiments, the target ratio of the first rAAV particle to the second rAAV particle is measured by measuring a level of DNA from the first rAAV particle and a level of DNA from the second rAAV particle.

Nucleic Acid Vectors and rAAV Particles

Aspects of the disclosure relate to nucleic acid vectors for co-packaging into rAAV (recombinant adeno-associated virus) particles. The produced rAAV particles have many uses, e.g., in methods and pharmaceutical compositions for treating a disease in a subject in need thereof (e.g., a subject having a disease involving reduced protein expression that may be treated with gene therapy), for infecting cells to screen rAAV particles for a desired phenotype (e.g., upregulation of a protein or polypeptide of interest in the cell), or for infecting animals to screen for pharmacokinetics and/or therapeutic efficacy of an rAAV.

In some embodiments, a first nucleic acid vector and a second nucleic acid vector are contemplated for use in a method described herein. In some embodiments, further nucleic acid vectors are contemplated for use in a method described herein (a first, second, third, fourth, and/or fifth nucleic acid vector, etc.). The terms "first", "second", "third", etc., are not meant to imply a specific order or importance unless explicitly indicated otherwise.

In some embodiments, each nucleic acid vector comprises a construct (e.g., an expression construct) comprising (a) one or more heterologous nucleic acid regions comprising a sequence encoding a protein or polypeptide of interest or encoding an RNA of interest (e.g., a microRNA or a small hairpin RNA (shRNA)) and (b) one or more regions comprising inverted terminal repeat (ITR) sequences (e.g., wild-type ITR sequences or engineered ITR sequences) flanking the one or more heterologous nucleic acid regions. In some embodiments, each nucleic acid vector is circular. In some embodiments, each nucleic acid vector is a plasmid (e.g., comprising an origin of replication (such as an $E.$ $coli$ ORI) and optionally a selectable marker (such as an Ampicillin or Kanamycin selectable marker)). In some embodiments, each nucleic acid vector is single-stranded. In some embodiments, each nucleic acid vector is double-stranded. In some embodiments, a double-stranded nucleic acid vector may be, for example, a self-complimentary vector that contains a region of the nucleic acid vector that is complementary to another region of the nucleic acid vector, initiating the formation of the double-strandedness of the nucleic acid vector. In some embodiments, the nucleic acid vector comprises a baculovirus or a HSV genomic sequence. In some embodiments the genomic sequence is modified to remove genes for replication of a baculovirus or HSV. Baculovirus and HSV nucleic acid vectors and genomic sequences are known in the art (see, e.g., Clement et al. Large-Scale Adeno-Associated Viral Vector Production Using a Herpesvirus-Based System Enables Manufacturing for Clinical Studies. Human Gene Therapy. 20:796-806; and Kotin. Large-scale recombinant adeno-associated virus production. Human Molecular Genetics, 2011, Vol. 20, Review Issue 1, R2-R6).

In some embodiments, as part of a method described herein, each construct contained within each nucleic acid vector is packaged within a viral capsid to produce one or more rAAV particles (e.g., a first rAAV particle comprising a first construct and a second rAAV particle comprising a second construct). Accordingly, in some embodiments, each rAAV particle comprises a viral capsid and a construct as described herein, which is encapsidated by the viral capsid.

In some embodiments, each construct comprises (1) one or more heterologous nucleic acid regions comprising a sequence encoding a protein or polypeptide of interest, (2) one or more nucleic acid regions comprising a sequence that facilitates expression of the heterologous nucleic acid region (e.g., a promoter and/or enhancer), and (3) one or more nucleic acid regions comprising a sequence that facilitates integration of the heterologous nucleic acid region (optionally with the one or more nucleic acid regions comprising a sequence that facilitates expression) into the genome of the subject. In some embodiments, viral sequences that facilitate integration comprise Inverted Terminal Repeat (ITR) sequences. In some embodiments, each construct comprises one or more heterologous nucleic acid regions comprising a sequence encoding a protein or polypeptide of interest or an RNA of interest operably linked to a promoter, wherein the one or more heterologous nucleic acid regions are flanked on each side (e.g., flanked on each the 5' and 3' side of the one or more heterologous nucleic acid regions) with a nucleic acid region comprising an ITR sequence. The ITR sequences can be derived from any AAV serotype (e.g., 1, 2, 3, 4, 5, 6, 7, 8, 9, or 10) or can be derived from more than one serotype. In some embodiments, the ITR sequences are derived from AAV2. ITR sequences and plasmids containing ITR sequences are known in the art and commercially available (see, e.g., products and services available from Vector Biolabs, Philadelphia, Pa.; Cellbiolabs, San Diego, Calif.; Agilent Technologies, Santa Clara, Ca; and Addgene, Cambridge, Mass.; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene TherapyMethods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962, 313, all of which are incorporated herein by reference).

In some embodiments, each nucleic acid vector comprises a pTR-UF-11 plasmid backbone, which is a plasmid that contains AAV2 ITRs. This plasmid is commercially available from the American Type Culture Collection (ATCC MBA-331).

In some embodiments, the construct comprises one or more regions comprising a sequence that facilitates expression of the heterologous nucleic acid, e.g., expression control sequences operatively linked to the heterologous nucleic acid. Numerous such sequences are known in the art. Non-limiting examples of expression control sequences include promoters, insulators, silencers, response elements, introns, enhancers, initiation sites, termination signals, and poly(A) tails. Any combination of such control sequences is completed herein (e.g., a promoter and an enhancer).

To achieve appropriate expression levels of the protein or polypeptide of interest, any of a number of promoters suitable for use in the selected host cell may be employed. The promoter may be, for example, a constitutive promoter, tissue-specific promoter, inducible promoter, or a synthetic promoter. For example, constitutive promoters of different strengths can be used. A construct described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and cytomegalovirus (CMV) promoters. Non-limiting examples of constitutive mammalian promoters include various housekeeping gene promoters, as exemplified by the (3-actin promoter.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. Non-limiting examples of such promoters that may be used include (1) desmin (DES), creatine kinase, myogenin, alpha myosin heavy chain, human brain and natriuretic peptide, specific for muscle cells, and (2) liver specific promoter [LSP, (GENEART®, LIFE TECHNOLOGIES™)], albumin, alpha-1-antitrypsin, hepatitis B virus core protein promoters, specific for liver cells.

Synthetic promoters are also contemplated herein. A synthetic promoter may comprise, for example, regions of known promoters, regulatory elements, transcription factor binding sites, enhancer elements, repressor elements, and the like.

In some embodiments, a first construct described herein comprises a first promoter and a second construct described herein comprises a second promoter. In some embodiments, the first promoter and the second promoter are different (e.g., the first promoter is DES and the second promoter is LSP). In some embodiments, the first and second promoters are selected from DES, LSP, parathyroid hormone receptor; kidney-specific promoter (P1), Synapsin, minimal human glucose-6-phosphatase promoter, MTM1, CMV and chicken beta-actin. Exemplary first and second promoter pairs include (a) DES and LSP, (b) LSP and P1, (c) Synapsin and DES, (d) LSP and minimal human glucose-6-phosphatase promoter, and (e) MTM1 and LSP. Such promoters are known in the art and described herein (see, e.g., Synapsin (neuronal specific; commercially available at Addgene. ID #22907); P1 [parathyroid hormone receptor; kidney-specific promoter (McCuaig K A, Lee H S, Clarke J C, Assar H, Horsford J, White J H. Parathyroid hormone/parathyroid hormone related peptide receptor gene transcripts are expressed from tissue-specific and ubiquitous promoters. Nucleic Acids Res 1995; 23: 1948-1955)]; minimal human glucose-6-phosphatase promoter (Lin B, Morris D W, Chou J Y. The role of HNF1alpha, HNF3gamma, and cyclic AMP in glucose-6-phosphatase gene activation. Biochemistry 1997; 36: 14096-14106; Schmoll D, Wasner C, Hinds C J, Allan B B, Walther R, Burchell A. Identification of a cAMP response element within the glucose-6-phosphatase hydrolytic subunit gene promoter which is involved in the transcriptional regulation by cAMP and glucocorticoids in H4IIE hepatoma cells. Biochem J 1999; 338: 457-463; Vander Kooi B T, Streeper R S, Svitek C A, Oeser J K, Powell D R, O'Brien R M. The three insulin response sequences in the glucose-6-phosphatase catalytic subunit gene promoter are functionally distinct. J Biol Chem 2003; 278: 11782-11793); and Endogenous MTM1 promoter (commercially available at GeneCopoeia; Accession # NM_000252; Product ID: HPRM15185)). In some embodiments, the first promoter and the second promoter are the same (e.g., the first promoter is DES and the second promoter is DES). In some embodiments, the first and second promoter are both CMV promoters, both chicken beta-actin promoters, both LSPs, both P1 promoters, both Synapsin promoters, both minimal human glucose-6-phosphatase promoters, or both MTM1 promoters.

In some embodiments, each construct comprises one or more heterologous nucleic acid regions comprising a sequence encoding a protein or polypeptide of interest. In some embodiments, the first construct and the second construct (and optionally third, fourth, fifth constructs, etc.) each comprise a sequence encoding the same protein or polypeptide of interest (e.g., both the first and second constructs encode GAA). In some embodiments, the first construct and the second construct (and optionally third, fourth, fifth constructs, etc.) each comprise a sequence encoding different proteins or polypeptides of interest (e.g., the first construct encodes a first protein or polypeptide of interest and second construct encodes a second protein or polypeptide of interest, etc.). In some embodiments, the constructs each encode a fragment of dystrophin, e.g., three fragments within three constructs (see, e.g., Lostal et al., Full-Length Dystrophin Reconstitution with Adeno-Associated Viral Vectors. Hum. Gene Ther., 2014. PMID: 24580018). In some embodiments, the first construct encodes beta-hexosaminidase alpha and the second construct encodes beta-hexosaminidase-beta (see, e.g., Cachon-Gonzalez et al., Gene transfer corrects acute GM2 gangliosidosis—potential therapeutic contribution of perivascular enzyme flow. Mol. Ther., 2012. PMID: 22453766). In some embodiments, the constructs each encode a fragment of myosin 7A, e.g., two fragments within two constructs (see, e.g., Dyka et al., Dual AAV Vectors Result in Efficient In Vitro and In Vivo expression of an Oversized Gene, MYO7A. Hum Gene Ther., 2014. PMID: 24568220). In some embodiments, the first construct encodes Vascular endothelial growth factor-A (VEGF-A, VEGF) and the second construct encodes fibroblast growth factor 4 (FGF4) (see, e.g., Jazwa et al., Arteriogenic therapy based on simultaneous delivery of VEGF-A and FGF4 genes improves the recovery from acute limb ischemia. Vasc. Cell. 2013. PMID: 23816205). In some embodiments, the first construct encodes Vascular endothelial growth factor-A (VEGF-A, VEGF) and the second construct encodes Angiopoietin-1 (see, e.g., Arsic et al., Induction of functional neovascularization by combined VEGF and Angiopoietin-1 gene transfer using AAV vectors. Mol. Ther., 2003. PMID: 12727107). In some embodiments, the first construct encodes the heavy chain of factor VIII and the second construct encodes the light chain of factor VII (see, e.g., Mah et al., Dual vectors expressing murine factor VIII result in sustained correction of hemophilia A mice. Hum. Gene Ther., 2003. PMID: 12614565). In some embodiments of any of the constructs above, the promoter for each construct is a tissue-specific or a constitutive promoter. In some embodiments of any of the constructs above, the promoter for each construct is CMV or chicken beta-actin.

In some embodiments, each construct comprises one or more heterologous nucleic acid regions comprising a sequence encoding a protein or polypeptide of interest and a promoter. In some embodiments, the first construct and the construct each encode the same protein or polypeptide of interest but comprise different promoter regions (e.g., the first construct comprises GAA operably linked to a DES promoter and the second construct comprises GAA operably linked to a LSP). In some embodiments, the first construct and the second construct encode the different proteins or polypeptides of interest and comprise different promoter regions (e.g., the first construct comprises hexosaminidase A operably linked to a DES promoter and the second construct comprises hexosaminidase B operably linked to a CMV promoter).

In some embodiments, the first and second constructs do not include a promoter region. In some embodiments, the first and second constructs include different regions of a nucleic acid encoding a protein or polypeptide of interest (e.g., different regions each encoding only a portion of a protein or polypeptide of interest). In some embodiments, the different regions are overlapping regions of the same gene. In some embodiments, the different regions are non-overlapping regions of the same gene. In some embodiments, more than two different constructs (e.g., 3, 4, 5, 6, 7, 8, 9, 10 or more) are packaged together. In some embodiments, the more than two different constructs include more than two different (e.g., overlapping or non-overlapping) regions of a gene of interest. In some embodiments, a resulting AAV preparation can be used to deliver two or more regions of a gene to a cell, for example, to be used as templates for altering (e.g., for correcting one or more mutations associated with a disease or condition) a genomic sequence in the cell (e.g., as a form of gene therapy). In some embodiments, these two or more regions can act as rescue sequences in a procedure that also involves delivering one or more genome editing nucleases to the cell.

The protein or polypeptide of interest may be, e.g., a polypeptide or protein of interest provided in Table 1. The sequences of the polypeptide or protein of interest may be obtained, e.g., using the non-limiting National Center for Biotechnology Information (NCBI) Protein IDs or SEQ ID NOs from patent applications provided in Table 1.

TABLE 1

Non-limiting examples of proteins or polypeptides of interest and associated diseases, disorders, or phenotypes

| Protein or Polypeptide | Non-limiting Exemplary diseases, disorders, or phenotypes | Non-limiting NCBI Protein IDs or Patent SEQ ID NOs |
|---|---|---|
| acid alpha-glucosidase (GAA) | Pompe disease | NP_000143.2, NP_001073271.1, NP_001073272.1 |
| Methyl CpG binding protein 2 (MECP2) | Rett syndrome | NP_001104262.1, NP_004983.1 |
| Aromatic L-amino acid decarboxylase (AADC) | Parkinson's disease | NP_000781.1, NP_001076440.1, NP_001229815.1, NP_001229816.1, NP_001229817.1, NP_001229818.1, NP_001229819.1 |
| Glial cell-derived neurotrophic factor (GDNF) | Parkinson's disease | NP_000505.1, NP_001177397.1, NP_001177398.1, NP_001265027.1, NP_954701.1 |
| Cystic fibrosis transmembrane conductance regulator (CFTR) | Cystic fibrosis | NP_000483.3 |
| Tumor necrosis factor receptor fused to an antibody Fc (TNFR:Fc) | Arthritis, Rheumatoid arthritis | SEQ ID NO. 1 of WO2013025079 |
| HIV-1 gag-proΔrt (tgAAC09) | HIV infection | SEQ ID NOs. 1-5 of WO2006073496 |
| Sarcoglycan alpha, beta, gamma, delta, epsilon, or zeta (SGCA, SGCB, SGCG, SGCD, SGCE, or SGCZ) | Muscular dystrophy | SGCA NP_000014.1, NP_001129169.1 SGCB NP_000223.1 |

TABLE 1-continued

Non-limiting examples of proteins or polypeptides of interest
and associated diseases, disorders, or phenotypes

| Protein or Polypeptide | Non-limiting Exemplary diseases, disorders, or phenotypes | Non-limiting NCBI Protein IDs or Patent SEQ ID NOs |
|---|---|---|
| | | SGCG NP_000222.1 SGCD NP_000328.2, NP_001121681.1, NP_758447.1 SGCE NP_001092870.1, NP_001092871.1, NP_003910.1 SGCZ NP_631906.2 |
| Alpha-1-antitrypsin (AAT) | Hereditary emphysema or Alpha-1-antitrypsin Deficiency | NP_000286.3, NP_001002235.1, NP_001002236.1, NP_001121172.1, NP_001121173.1, NP_001121174.1, NP_001121175.1, NP_001121176.1, NP_001121177.1, NP_001121178.1, NP_001121179.1 |
| Glutamate decarboxylase 1 (GAD1) | Parkinson's disease | NP_000808.2, NP_038473.2 |
| Glutamate decarboxylase 2 (GAD2) | Parkinson's disease | NP_000809.1, NP_001127838.1 |
| Aspartoacylase (ASPA) | Canavan's disease | NP_000040.1, NP_001121557.1 |
| Nerve growth factor (NGF) | Alzheimer's disease | NP_002497.2 |
| Granulocyte-macrophage colonystimulating factory (GM-CSF) | Prostate cancer | NP_000749.2 |
| Cluster of Differentiation 86 (CD86 or B7-2) | Malignant melanoma | NP_001193853.1, NP_001193854.1, NP_008820.3, NP_787058.4, NP_795711.1 |
| Interleukin 12 (IL-12) | Malignant melanoma | NP_000873.2, NP_002178.2 |
| neuropeptide Y (NPY) | Parkinson's disease, epilepsy | NP_000896.1 |
| ATPase, Ca++ transporting, cardiac muscle, slow twitch 2 (SERCA2) | Chronic heart failure | NP_001672.1, NP_733765.1 |
| Dystrophin or Minidystrophin | Muscular dystrophy | NP_000100.2, NP_003997.1, NP_004000.1, NP_004001.1, NP_004002.2, NP_004003.1, NP_004004.1, NP_004005.1, NP_004006.1, NP_004007.1, NP_004008.1, NP_004009.1, NP_004010.1, NP_004011.2, NP_004012.1, NP_004013.1, NP_004014.1 |
| Ceroid lipofuscinosis neuronal 2 (CLN2) | Late infantile neuronal ceroidlipofuscinosis or Batten's disease | NP_000382.3 |
| Neurturin (NRTN) | Parkinson's disease | NP_004549.1 |
| N-acetylglucosaminidase, alpha (NAGLU) | Sanfilippo syndrome (MPSIIIB) | NP_000254.2 |
| Iduronidase, alpha-1 (IDUA) | MPSI-Hurler | NP_000194.2 |
| Iduronate 2-sulfatase (IDS) | MPSII-Hunter | NP_000193.1, NP_001160022.1, NP_006114.1 |
| Glucuronidase, beta (GUSB) | MPSVII-Sly | NP_000172.2, NP_001271219.1 |

TABLE 1-continued

Non-limiting examples of proteins or polypeptides of interest
and associated diseases, disorders, or phenotypes

| Protein or Polypeptide | Non-limiting Exemplary diseases, disorders, or phenotypes | Non-limiting NCBI Protein IDs or Patent SEQ ID NOs |
|---|---|---|
| Hexosaminidase A, α polypeptide, also called beta-Hexosaminidase alpha (HEXA) | Tay-Sachs | NP_000511.2 |
| Hexosaminidase B, β polypeptide, also called beta-Hexosaminidase beta (HEXB) | Tay-Sachs | NP_000512.1, NP_001278933.1 |
| Retinal pigment epithelium-specific protein 65 kDa (RPE65) | Leber congenital amaurosis | NP_000320.1 |
| Factor IX (FIX) | Hemophilia B | NP_000124.1 |
| Adenine nucleotide translocator (ANT-1) | progressive external ophthalmoplegia | NP_001142.2 |
| ApaLI | mitochondrial heteroplasmy, myoclonic epilepsy with ragged red fibers (MERRF) or mitochondrial encephalomyopathy, lactic acidosis, and stroke-like episodes (MELAS) | YP_007161330.1 |
| NADH ubiquinone oxidoreductase subunit 4 (ND4) | Leber hereditary Optic | YP_003024035.1 |
| very long-acyl-CoA dehydrogenase (VLCAD) | very long-chain acyl-CoA dehydrogenase (VLCAD) deficiency | NP_000009.1, NP_001029031.1, NP_001257376.1, NP_001257377.1 |
| short-chain acyl-CoA dehydrogenase (SCAD) | short-chain acyl-CoA dehydrogenase (SCAD) deficiency | NP_000008.1 |
| medium-chain acyl-CoA dehydrogenase (MCAD) | medium-chain acyl-CoA dehydrogenase (MCAD) deficiency | NP_000007.1, NP_001120800.1, NP_001272971.1, NP_001272972.1, NP_001272973.1 |
| Myotubularin 1 (MTM1) | X-linked myotubular myopathy | NP_000243.1 |
| Myophosphorylase (PYGM) | McArdle disease (glycogen storage disease type V, myophosphorylase deficiency) | NP_001158188.1, NP_005600.1 |
| Lipoprotein lipase (LPL) | LPL deficiency | NP_000228.1 |
| sFLT01 (VEGF/PlGF (placental growth factor) binding domain of human VEGFR1/Flt-1 (hVEGFR1) fused to the Fc portion of human IgG(1) through a polyglycine linker) | Age-related macular degeneration | SEQ ID NO: 2, 8, 21, 23, or 25 of WO2009105669 |
| Glucocerebrosidase (GC) | Gaucher disease | NP_000148.2, NP_001005741.1, NP_001005742.1, NP_001165282.1, NP_001165283.1 |
| UDP glucuronosyltransferase 1 family, polypeptide A1 (UGT1A1) | Crigler-Najjar syndrome | NP_000454.1 |
| Glucose 6-phosphatase (G6Pase) | GSD-Ia | NP_000142.2, NP_001257326.1 |
| Ornithine carbamoyltransferase (OTC) | OTC deficiency | NP_000522.3 |
| Cystathionine-beta-synthase (CBS) | Homocystinuria | NP_000062.1, NP_001171479.1, NP_001171480.1 |
| Factor VIII (F8) | Haemophilia A | NP_000123.1, NP_063916.1 |
| Hemochromatosis (HFE) | Hemochromatosis | NP_000401.1, NP_620572.1, NP_620573.1, NP_620575.1, NP_620576.1, NP_620577.1, NP_620578.1, NP_620579.1, NP_620580.1 |
| Low density lipoprotein receptor (LDLR) | Phenylketonuria (PKU) | NP_000518.1, NP_001182727.1, NP_001182728.1, NP_001182729.1, NP_001182732.1 |

TABLE 1-continued

Non-limiting examples of proteins or polypeptides of interest
and associated diseases, disorders, or phenotypes

| Protein or Polypeptide | Non-limiting Exemplary diseases, disorders, or phenotypes | Non-limiting NCBI Protein IDs or Patent SEQ ID NOs |
|---|---|---|
| Galactosidase, alpha (AGA) | Fabry disease | NP_000160.1 |
| Phenylalanine hydroxylase (PAH) | Hypercholesterolaemia or Phenylketonuria (PKU) | NP_000268.1 |
| Propionyl CoA carboxylase, alpha polypeptide (PCCA) | Propionic acidaemias | NP_000273.2, NP_001121164.1, NP_001171475.1 |
| myosin 7A (MYO7A) | Usher syndrome 1B | NP_000251.3, NP_001120651.2, NP_001120652.1 |
| Vascular endothelial growth factor-A (VEGF-A, VEGF) | Ischemia, Vascular defects, Heart failure | NP_001020537.2, NP_001020538.2, NP_001020539.2, NP_001020540.2, NP_001020541.2, NP_001028928.1, NP_001165093.1, NP_001165094.1, NP_001165095.1, NP_001165096.1, NP_001165097.1, NP_001165098.1, NP_001165099.1, NP_001165100.1, NP_001165101.1, NP_001191313.1, NP_001191314.1, NP_001273973.1, NP_003367.4 |
| Fibroblast growth factor 4 (FGF4) | Ischemia, Heart failure | NP_001998.1 |
| Angiopoietin-1 (ANGPT1) | Vascular defects, Heart failure | NP_001137.2, NP_001186788.1 |
| cystinosin, lysosomal cystine transporter (CTNS) | Cystinosis | NP_001026851.2, NP_004928.2 |
| Insulin-like growth factor (IGF-1) | amyotrophic lateral sclerosis | NP_000609.1, NP_001104753.1, NP_001104754.1, NP_001104755.1 |
| adenosine deaminase, RNA-specific, B1 (ADARB1) | amyotrophic lateral sclerosis | NP_001103.1, NP_001153702.1, NP_056648.1, NP_056649.1 |
| peripherin 2 (PRPH2) | retinitis pigmentosa | NP_000313.2 |
| c-mer proto-oncogene tyrosine kinase (MERTK) | retinitis pigmentosa | NP_006334.2 |

The polypeptides and proteins provided in Table 1 are known in the art for use in rAAV particles (see, e.g., Adeno-Associated Virus Vectors in Clinical Trials. Barrie J. Carter. Human Gene Therapy. May 2005, 16(5): 541-550. doi:10.1089/hum.2005.16.541. Published in Volume: 16 Issue 5: May 25, 2005; Neuropharmacology. 2013 June; 69:82-8. doi: 10.1016/j.neuropharm.2012.03.004. Epub 2012 Mar. 17; Adeno-associated virus (AAV) gene therapy for neurological disease. Weinberg MS1, Samulski R J, McCown T J. Gene therapy for lysosomal storage disorders. Yew N S, Cheng S H. Pediatr Endocrinol Rev. 2013 November; 11 Suppl 1:99-109; Directed evolution of novel adeno-associated viruses for therapeutic gene delivery. Bartel M A, Weinstein J R, Schaffer D V. Gene Ther. 2012 June; 19(6): 694-700. doi: 10.1038/gt.2012.20. Epub 2012 Mar. 8; Therapeutic in vivo gene transfer for genetic disease using AAV: progress and challenges. Mingozzi F, High K A. Nat Rev Genet. 2011 May; 12(5):341-55. doi: 10.1038/nrg2988). In some embodiments, the polypeptide or protein of interest is a human protein or polypeptide.

In some embodiments, each construct comprises one or more heterologous nucleic acid regions comprising a sequence encoding a RNA of interest (e.g., an shRNA or microRNA) and a promoter. Exemplary RNAs of interest and AAV vectors comprising such RNAs include, e.g., AAVsh2.4, AAVsh8.2, AAVsh30.1, AAV-shHD2, siRNAs Targeting TGFβ1, TGFβR2, and CTGF, scAAV2-IRE1alpha, XBP1 and ATF6. Such RNAs are known in the art (see, e.g., McBride et al., Artificial miRNAs mitigate shRNA-mediated toxicity in the brain: Implications for the therapeutic development of RNAi. PNAS, 2008. doi: 10.1073/pnas.0801775105; Franich et al., AAV Vector-mediated RNAi of Mutant Huntingtin Expression Is Neuroprotective in a Novel Genetic Rat Model of Huntington's Disease. Mol. Ther., 2008. doi:10.1038/mt.2008.50; Sriram et al., Triple Combination of siRNAs Targeting TGFβ1, TGFβR2, and CTGF Enhances Reduction of Collagen I and Smooth Muscle Actin in Corneal Fibroblasts. IOVS., 2013. doi: 10.1167/iovs.13-12758; and Ruan et al., Development of an anti-angiogenic therapeutic model combining scAAV2-delivered siRNAs and noninvasive photoacoustic imaging of tumor vasculature development. Cancer Letters, 2013. DOI: 10.1016/j.canlet.2012.11.016). Other exemplary RNAs of interest include RNAs (e.g., microRNAs or shRNAs) that target Huntingtin (HTT, see, e.g., NM_002111.7), Ataxin-1 (ATXN1, see, e.g., NM_000332.3 or NM_001128164.1), TGFβ1 (TGFB1, see, e.g., NM_000660.5), TGFβR2 (TGFBR2, see, e.g., NM_001024847.2 or NM_003242.5), connective tissue growth factor (CTGF, see, e.g., NM_001901.2), IRE1alpha (IRE1a, see, e.g., NM_001433.3), X-box binding protein 1 (XBP1, see, e.g., NM_001079539.1 or NM_005080.3) and activating transcription factor 6 (ATF6, see, e.g., NM_007348.3). Such RNAs of interest may be used to treat, e.g., Huntington's disease, cancer, hypervascularization, and spinocerebellar ataxia type 1.

In some embodiments, a nucleic acid vector or construct described herein may also contain marker or reporter genes, e.g., LacZ or a florescent protein.

In some embodiments, a nucleic acid vector or construct described herein can be used to deliver a genome editing nuclease to a cell (for example by delivering a nucleic acid encoding a genome editing nuclease), for example an engineered nuclease that can be useful to target genomic nucleic acid for cleavage (e.g., to create a double-stranded break at a known target position in the genome of a cell that receives the genome editing nuclease). In some embodiments, a genome editing nuclease is a zinc finger nuclease (ZFN), a transcription activator-like effector nuclease (TALEN), a meganuclease, an RNA-guided DNA endonuclease (e.g., a CRISPR Cas9 related nuclease), or a combination thereof. In some embodiments, a Cas9 related nuclease is a naturally occurring endonuclease. In some embodiments, a Cas9 related nuclease is a sequence variant or a fragment of a naturally occurring Cas9 endonuclease and/or a chimeric nuclease including a naturally occurring or variant Cas9 endonuclease (or a fragment of one or more thereof). In some embodiments, a nucleic acid encoding a Cas9 related nuclease is delivered along with a nucleic acid encoding a guide RNA. In some embodiments, a guide RNA is a synthetic RNA that includes a targeting segment that is complementary to a strand of a target region (e.g., a genomic target region of interest), and a nuclease interacting segment that interacts with (e.g., binds or guides) an RNA-guided nuclease. In some embodiments, a guide RNA includes a sequence that targets a gene to be edited to restore its function (e.g., for therapeutic purposes). In some embodiments, a guide RNA targets a dystrophin gene (e.g., a region of a dystrophin gene that contains a mutation associated with DMD).

In some embodiments, a genome editing nuclease (e.g., a Cas9 related nuclease and a guide RNA) are delivered along with a rescue nucleic acid (e.g., a rescue DNA or RNA molecule) that can be used as a template for genomic repair after cleavage by the genome editing nuclease. In some embodiments, the rescue nucleic acid has a sequence of a target nucleic acid that does not include a mutation associated with a disease. For example, in some embodiments, a rescue nucleic acid includes a portion of a DMD-associated nucleic acid (e.g., a region of a dystrophin gene) that does not contain a mutation associated with DMD (e.g., a wild-type DMD genomic sequence).

In some embodiments, two or more different rAAV particles are used to deliver a rescue nucleic acid and a nucleic acid encoding a genome editing nuclease. In some embodiments, two or more different rAAV particles are used to deliver a Cas9 related nuclease (e.g., a nucleic acid encoding a Cas9 related nuclease) and a guide RNA (e.g., a nucleic acid encoding a guide RNA). In some embodiments, the rescue nucleic acid provides a region of a DMD associated gene that does not contain a mutation associated with DMD, and the guide RNA includes a targeting portion that targets a Cas9 related nuclease to cleave genomic DNA in or near the region of the DMD associated gene corresponding to the rescue nucleic acid. In some embodiments, the different AAV vectors are delivered together (e.g., simultaneously) to a cell (for example a cell from a subject, e.g., a human subject) that is being targeted for genomic editing.

Accordingly, in some embodiments methods and compositions described herein can be used to package two or more different nucleic acid vectors (e.g., including a rescue nucleic acid, and/or a nucleic acid encoding a genomic editing nuclease, and/or a nucleic acid encoding a guide RNA) simultaneously into a rAAV in order to produce an rAAV preparation including different rAAV particles each containing one of the nucleic acid vectors. For example, methods and compositions described herein can be used to prepare and deliver combinations of these different vectors in different ratios of interest.

Nucleic acid vectors containing constructs (e.g., expression constructs) and methods of producing such nucleic acid vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.).

Producing rAAV Particle Preparations

Other aspects of the disclosure relate to producing rAAV particle preparations, e.g., by contacting a cell preparation with a first nucleic acid vector comprising a first construct as described herein and a second nucleic acid vector comprising a second construct as described herein, permitting the cell preparation to produce a first rAAV particle comprising the first construct and a second rAAV particle comprising the second construct, and isolating the first rAAV particle and the second rAAV particle from the cell preparation. In some embodiments, further nucleic acid vectors (e.g., third, fourth, fifth, etc.) and further rAAV particles (third, fourth, fifth, etc.) are also contemplated herein.

In some embodiments, the cell preparation is a mammalian cell preparation or an insect cell preparation. In some embodiments, the mammalian cell preparation comprises 293 cells or baby hamster kidney cells (BHK) (available, e.g., from ATCC® CRL-1573™ (293 [HEK-293]) for 293 cells and ATCC® CCL-10™ (BHK-21 [C-13]) for BHK cells). In some embodiments, the insect cell preparation comprises Sf9 cells (available, e.g., from ATCC® CRL-1711™ (Sf9 cells)).

In some embodiments, the cell preparation, after contact with the first and second nucleic acid vector (and optionally third, fourth, fifth, etc. nucleic acid vectors), is maintained under conditions sufficient for producing a first rAAV particle comprising the first construct and a second rAAV particle comprising the second construct (and optionally third, fourth, fifth, etc. rAAV particles comprising third, fourth, fifth, etc. constructs). In some embodiments, the conditions sufficient for producing comprise incubating the cell preparation for an appropriate length of time, in an appropriate medium, and at an appropriate temperature. In some embodiments, the length of time is 12 to 72 hours, 24 to 72 hours, or 48 to 72 hours. In some embodiments, the length of time is at least 24 hours, at least 48 hours, at least 60 hours or at least 72 hours. In some embodiments, the temperature is 37 degrees Celsius. In some embodiments, the medium comprises nutrients for maintaining cell health and/or growth. In some embodiments, the medium comprises Dulbecco's modified Eagle's medium, 293 SFM II, GIBCO® FREESTYLE™ 293 Expression Medium (serum-free, protein-free medium), CD 293 Medium, EXPI293™ Expression Medium (serum-free, protein-free medium for HEK 293 cells), SF-900™ III SFM (serum-free, protein-free, insect cell culture medium), EXPRESS FIVE® SFM (serum-free, protein-free, insect cell culture medium), or SF-900™ II SFM (serum-free, protein free, insect cell culture medium) (available from LIFE TECHNOLOGIES™).

In some embodiments, the cell preparation is contacted simultaneously with the first nucleic acid vector and the second nucleic acid vector (and optionally third, fourth, fifth, etc. nucleic acid vectors). In some embodiments, the cell preparation is contacted with a composition comprising the first nucleic acid vector and the second nucleic acid vector (and optionally third, fourth, fifth, etc. nucleic acid vectors). In some embodiments, the composition comprises calcium chloride and/or hank's balanced saline solution. In some embodiments, the composition further comprises one or more helper plasmids as described herein.

In some embodiments, contacting a cell preparation with a first and second nucleic acid vector (and optionally third, fourth, fifth, etc. nucleic acid vectors) comprises transfecting the cell preparation with the first nucleic acid vector and the second nucleic acid vector (and optionally third, fourth, fifth, etc. nucleic acid vectors). In some embodiments, the transfection is calcium phosphate transfection. In some embodiments, the method further comprises contacting the cell preparation with at least one helper plasmid described herein. In some embodiments, the cell preparation is transfected simultaneously with the first nucleic acid vector and the second nucleic acid vector (e.g., as plasmids) and the at least one helper plasmid (e.g., one, two, or three helper plasmids). In some embodiments, the first nucleic acid vector and the second nucleic acid vector (e.g., as plasmids) and the at least one helper plasmid are comprised within a composition before contacting with the cell preparation. In some embodiments, the composition comprises calcium chloride and/or hank's balanced saline solution.

In some embodiments, the at least one helper plasmid is a first helper plasmid comprising a rep gene and a cap gene and a second helper plasmid comprising a E1a gene, a E1b gene, a E4 gene, a E2a gene, and a VA gene. In some embodiments, the rep gene is a rep gene derived from AAV2 and the cap gene is derived from AAV9. Helper plasmids, and methods of making such plasmids, are described herein and also known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Ca; and Addgene, Cambridge, Mass.; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adenoassociated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adenoassociated viral vector reference standards, Molecular Therapy, Vol. 16, 1185-1188).

An exemplary, non-limiting transfection method is described in Example 1. Another exemplary, non-limiting, transfection method is described next. One or more helper plasmids are produced or obtained, which comprise rep and cap genes for the desired AAV serotype or pseudotype (e.g., rep2/cap9) and the adenoviral VA, E2A (DBP), and E4 genes under the transcriptional control of their native promoters. 293 cells are transfected via $CaPO_4$-mediated transfection with the helper plasmids and a first and second nucleic acid vector described herein (e.g., as plasmids).

In some embodiments, contacting a cell preparation with a first and second nucleic acid vector (and optionally third, fourth, fifth, etc. nucleic acid vectors) comprises infecting the cell preparation with the first nucleic acid vector and the second nucleic acid vector (and optionally third, fourth, fifth, etc. nucleic acid vectors). The cell preparation may be infected using any method known in the art, e.g., herpes simplex virus type 1 (HSV) infection or baculovirus infection (see, e.g., Clement et al. Large-Scale Adeno-Associated Viral Vector Production Using a Herpesvirus-Based System Enables Manufacturing for Clinical Studies. Human Gene Therapy. 20:796-806; and Kotin. Large-scale recombinant adeno-associated virus production. Human Molecular Genetics, 2011, Vol. 20, Review Issue 1, R2-R6).

In some embodiments, the first nucleic acid vector is contained within a first herpes simplex virus type 1 (HSV) particle and the second nucleic acid vector is contained within a second HSV particle (and optionally third, fourth, fifth, etc. nucleic acid vectors are contained within a third, fourth, fifth, etc. HSV particle). In some embodiments, the first HSV particle and the second HSV particle are contacted with the cell preparation (e.g., comprising 293 cells or BHK cells). In some embodiments, further HSV particles comprising one or more helper nucleic acids (e.g., comprising rep genes, cap genes, a E1a gene, a E1b gene, a E4 gene, a E2a gene, and/or a VA gene) are contacted with the cell preparation. In some embodiments, the one or more helper nucleic acids are stably integrated into the cell preparation such that the further HSV particles are optional.

In some embodiments, the first nucleic acid vector is contained within a first baculovirus particle and the second nucleic acid vector is contained within a second baculovirus particle (and optionally third, fourth, fifth, etc. nucleic acid vectors are contained within a third, fourth, fifth, etc. baculovirus particle). In some embodiments, the first baculovirus particle and the second baculovirus particle are contacted with the cell preparation (e.g., comprising Sf9 cells). In some embodiments, further baculovirus particles comprising one or more helper nucleic acids (e.g., comprising rep genes, cap genes, a E1a gene, a E1b gene, a E4 gene, a E2a gene, and/or a VA gene) are contacted with the cell preparation. In some embodiments, the one or more helper nucleic acids are stably integrated into the cell preparation such that the further baculovirus particles are optional.

An exemplary, non-limiting, infection method is described next. Sf9-based producer stable cell lines are infected with a first recombinant baculovirus comprising the first nucleic acid vector and the second recombinant baculovirus comprising the second nucleic acid vector.

In some embodiments, when the cell preparation is contacted with the first and second nucleic acid vector via infection, the initial ratio of the first nucleic acid vector to the second nucleic acid vector is the ratio of the multiplicity of infection of the first nucleic acid vector to the multiplicity of infection of the second nucleic acid vector. Multiplicity of infection or MOI is a term known in the art and refers to the ratio of infectious agents (e.g., HSV or baculovirus) to infection targets (e.g., cells).

The first and second rAAV particle, once produced by the cell preparation using any method described herein, may be isolated using any method known in the art or described herein. In some embodiments, isolation comprises lysing the cell preparation and extracting the first rAAV particle and the second rAAV particle. The first rAAV particle and the second rAAV particle may be extracted from the cell preparation simultaneously (e.g., a population of rAAV particles that comprises both the first rAAV particle and the second rAAV particle is extracted from the cell preparation such as using a purification method described herein) or separately. In some embodiments, extraction comprises purification, e.g., by iodixanol step gradient, CsCl gradient, chromatography, or polyethylene glycol (PEG) precipitation.

The first and second rAAV particle (and optionally third, fourth, fifth, etc. rAAV particles) produced by a method described herein may be of any AAV serotype, including any derivative or pseudotype (e.g., 1, 2, 3, 4, 5, 6, 7, 8, 9, or 10, or pseudotypes/derivatives thereof). In some embodiments, the first and second rAAV particle (and optionally third, fourth, fifth, etc. rAAV particles) are of the same serotype. In some embodiments, the first and second rAAV particle (and optionally third, fourth, fifth, etc. rAAV particles) are of the different serotypes. Non-limiting examples of derivatives and pseudotypes include rAAV2/1, rAAV2/5, rAAV2/8, rAAV2/9, AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6(Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J.). In some embodiments, the first and second rAAV particle (and optionally third, fourth, fifth, etc. rAAV particles) are pseudotyped rAAV particles. In some embodiments, the pseudotyped rAAV particle comprises (a) a nucleic acid vector comprising AAV2 ITRs and (b) a capsid comprised of capsid proteins derived from AAVx (e.g., AAV1, AAV3, AAV4, AAV5, AAV6, AAV7, AAV8, AAV9, or AAV10). Exemplary rAAV pseudotyped particles include, but are not limited to rAAV2/1, rAAV2/5, rAAV2/8, and rAAV2/9 particles. Methods for producing and using pseudotyped rAAV particles are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Exemplary rAAV Co-Production Protocol

Introduction

To date adeno-associated virus (AAV) has been used in over 100 gene therapy clinical trials. The widespread tropism, sustained gene expression and excellent safety data that exist for AAV are only a few of the reasons it has reached such popularity. As a non-pathogenic shuttle for therapeutic genes capable of delivering its payload to many cell types, the basic biological processes governing the behavior of the many AAV serotypes has been an extensive area of research for many years (Zincarelli et al., 2008; Asokan et al., 2012; Gurda et al., 2012; Aschauer et al., 2013; Asokan and Samulski 2013; Rayaprolu et al., 2013). With its success in correcting the pathology associated with diseases such as seen in the multitude of metabolic myopathies and hematological disorders, AAV is quickly becoming the gene therapy vector of choice for initiating large animal studies and clinical trials (Markusic and Herzog 2012; Mah et al., 2013).

However, among its drawbacks are host immune responses against the capsid and/or transgene (Boutin et al., 2010; Rogers et al., 2011; Faust et al., 2013; Mingozzi and High 2013), appropriate transduction of the target tissue (Zincarelli et al., 2008; Pulicherla et al., 2011; Aschauer et al., 2013), size limitation, with an optimal packaging size of ~4.7 kb (Dong et al., 1996), and the challenges to produce high titer vectors in a cost and time effective manner (Clément et al., 2009; Doria et al., 2013). Implementation towards large-scale manufacturing of AAV using infection-based systems (herpes simplex virus type 1 and baculovirus systems) rather than transfection will certainly become useful to address the large quantities of virus needed for FDA required extensive pre-clinical studies, as well as clinical studies. Yet transfection remains the current standard of vector production in most laboratories and manufacturing cores. Furthermore, some indications may require the use of two or more vector constructs. To palliate the inability of AAV genomes to carry long therapeutic cDNA, the packaging capacity may be expanded by splitting the genome and rely on what has been referred to as the fragment AAV reassembly model (Rabinowitz et al., 2002; Hirsch et al., 2013). Gene expression using fragmented vectors relies on the host recombination machinery to splice together one expression cassette containing a splice donor site to another encoding a compatible splice acceptor region (Ghosh et al., 2011). Encouraging results using this strategy have been reported for Duchenne's muscular dystrophy (Lai et al., 2005; Zhang and Duan 2012; Zhang et al., 2013; Koo et al., 2014) and Usher 1 (Lopes et al., 2013; Dyka et al., 2014).

However there are many other instances where the simultaneous delivery of more than one AAV vector may be required. Such as for indications where two or more subunits are needed (e.g., hexosaminidase A and B for Tay-Sachs disease) or indications where the expression of the therapeutic gene needs to be elevated in specific tissues; which could be mediated by the use of different promoters upstream of the same therapeutic transgene (Pacak et al., 2009; Palfi et al., 2012; Fagoe et al., 2013). For instance, targeting gene expression to the liver for the purposes of immune tolerance induction while providing an additional vector to correct systemic pathology would allow for the simultaneous treatment of many congenital metabolic myopathies wherein immune responses have proven deleterious to the efficacy of gene therapy.

Clinical applications using two or more AAV constructs would be time and cost prohibitive if each construct was produced separately. To facilitate the use and production of multiple vectors, a novel production method was investigated that exploited the stoichiometric properties of AAV in that only one expression plasmid is packaged per encapsidated virus. A method was developed that allowed for the production of multiple vectors in a single transfection step. Combining reporter expression cassettes to be packaged at a known input ratio, it was shown through quantitative PCR (qPCR) and in vitro infectivity assays that the output vector preparation closely recapitulated the input ratios. Additionally, it was shown that therapeutic constructs containing unique promoter elements could be co-packaged and were able to be differentially titrated. These results indicate that, at minimum, two vectors containing either separate transgenes or regulatory elements can be co-packaged and subsequently characterized independently.

Methods

Construction of rAAV Vector Plasmids

Recombinant vectors containing GFP (pTRUF11) and mCherry (pTRUF11-mCherry) were assembled using the pTR-UF backbone previously described (Zolotukhin et al., 1996). The sequences of PTR-UF and PTR-UF11 are provided below.

pTR-UF: (SEQ ID NO: 1)

5'-
AGGAACCCCTAGTGATGGAGTTGGCCACTCCCTCTCTGCGCGCTCGCTCG
CTCACTGAGGCCGCCCGGGCAAAGCCCGGGCGTCGGGCGACCTTTGGTCG
CCCGGCCTCAGTGAGCGAGCGAGCGCGCAGAGAGGGAGTGGCCAACCCCC
CCCCCCCCCCCCCTGCAGCCCTGCATTAATGAATCGGCCAACGCGCGGGG
AGAGGCGGTTTGCGTATTGGGCGCTCTTCCGCTTCCTCGCTCACTGACTC
GCTGCGCTCGGTCGTTCGGCTGCGGCGAGCGGTATCAGCTCACTCAAAGG
CGGTAATACGGTTATCCACAGAATCAGGGGATAACGCAGGAAAGAACATG
TGAGCAAAAGGCCAGCAAAAGGCCAGGAACCGTAAAAAGGCCGCGTTGCT
GGCGTTTTTCCATAGGCTCCGCCCCCCTGACGAGCATCACAAAAATCGAC
GCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTC
AATGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATC
CGGTAACTATCGTCTTGAGTCCAACCCGGTAAGACACGACTTATCGCCAC
TGGCAGCAGCCACTGGTAACAGGATTAGCAGAGCGAGGTATGTAGGCGGT
GCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGA
TCCTTTGATCTTTTCTACGGGGTCTGACGCTCAGTGGAACGAAAACTCAC
GTTAAGGGATTTTGGTCATGAGATTATCAAAAAGGATCTTCACCTAGATC
CTTTTAAATTAAAAATGAAGTTTTAAATCAATCTAAAGTATATATGAGTA
AACTTGGTCTGACAGTTACCAATGCTTAATCAGTGAGGCACCTATCTCAG
CGATCTGTCTATTTCGTTCATCCATAGTTGCCTGACTCCCCGTCGTGTAG
ATAACTACGATACGGGAGGGCTTACCATCTGGCCCCAGTGCTGCAATGAT
ACCGCGAGACCCACGCTCACCGGCTCCAGATTTATCAGCAATAAACCAGC
CAGCCGGAAGGGCCGAGCGCAGAAGTGGTCCTGCAACTTTATCCGCCTCC

ATCCAGTCTATTAATTGTTGCCGGGAAGCTAGAGTAAGTAGTTCGCCAGT
TAATAGTTTGCGCAACGTTGTTGCCATTGCTACAGGCATCGTGGTGTCAC
GCTCGTCGTTTGGTATGGCTTCATTCAGCTCCGGTTCCCAACGATCAAGG
CGAGTTACATGATCCCCCATGTTGTGCAAAAAAGCGGTTAGCTCCTTCGG
TCCTCCGATCGTTGTCAGAAGTAAGTTGGCCGCAGTGTTATCACTCATGG
TTATGGCAGCACTGCATAATTCTCTTACTGTCATGCCATCCGTAAGATGC
TTTTCTGTGACTGGTGAGTACTCAACCAAGTCATTCTGAGAATAGTGTAT
GCGGCGACCGAGTTGCTCTTGCCCGGCGTCAATACGGGATAATACCGCGC
CACATAGCAGAACTTTAAAAGTGCTCATCATTGGAAAACGTTCTTCGGGG
CGAAAACTCTCAAGGATCTTACCGCTGTTGAGATCCAGTTCGATGTAACC
CACTCGTGCACCCAACTGATCTTCAGCATCTTTTACTTTCACCAGCGTTT
CTGGGTGAGCAAAAACAGGAAGGCAAAATGCCGCAAAAAAGGGAATAAGG
GCGACACGGAAATGTTGAATACTCATACTCTTCCTTTTTCAATATTATTG
AAGCATTTATCAGGGTTATTGTCTCATGAGCGGATACATATTTGAATGTA
TTTAGAAAAATAAACAAATAGGGGTTCCGCGCACATTTCCCCGAAAAGTG
CCACCTGACGTCTAAGAAACCATTATTATCATGACATTAACCTATAAAAA
TAGGCGTATCACGAGGCCCTTTCGTCTCGCGCGTTTCGGTGATGACGGTG
AAAACCTCTGACACATGCAGCTCCCGGAGACGGTCACAGCTTGTCTGTAA
GCGGATGCCGGGAGCAGACAAGCCCGTCAGGGCGCGTCAGCGGGTGTTGG
CGGGTGTCGGGGCTGGCTTAACTATGCGGCATCAGAGCAGATTGTACTGA
GAGTGCACCATATGCGGTGTGAAATACCGCACAGATGCGTAAGGAGAAAA
TACCGCATCAGGAAATTGTAAACGTTAATATTTTGTTAAAATTCGCGTTA
AATTTTTGTTAAATCAGCTCATTTTTTAACCAATAGGCCGAAATCGGCAA
AATCCCTTATAAATCAAAAGAATAGACCGAGATAGGGTTGAGTGTTGTTC
CAGTTTGGAACAAGAGTCCACTATTAAAGAACGTGGACTCCAACGTCAAA
GGGCGAAAAACCGTCTATCAGGGCGATGGCCCACTACGTGAACCATCACC
CTAATCAAGTTTTTTGGGGTCGAGGTGCCGTAAAGCACTAAATCGGAACC
CTAAAGGGAGCCCCCGATTTAGAGCTTGACGGGGAAAGCCGGCGAACGTG
GCGAGAAAGGAAGGGAAGAAAGCGAAAGGAGCGGGCGCTAGGGCGCTGGC
AAGTGTAGCGGTCACGCTGCGCGTAACCACCACACCCGCCGCGCTTAATG
CGCCGCTACAGGGCGCGTCGCGCCATTCGCCATTCAGGCTACGCAACTGT
TGGGAAGGGCGATCGGTGCGGGCCTCTTCGCTATTACGCCAGGCTGCAGG
GGGGGGGGGGGGGGTTGGCCACTCCCTCTCTGCGCGCTCGCTCGCTCA
CTGAGGCCGGGCGACCAAAGGTCGCCCGACGCCCGGGCTTTGCCCGGGCG
GCCTCAGTGAGCGAGCGAGCGCGCAGAGAGGGAGTGGCCAACTCCATCAC
TAGGGGTTCCT pTR-UF11: (SEQ ID NO: 2)

5'-
GGGGGGGGGGGGGGGGGTTGGCCACTCCCTCTCTGCGCGCTCGCTCGCT
CACTGAGGCCGGGCGACCAAAGGTCGCCCGACGCCCGGGCTTTGCCCGGG
CGGCCTCAGTGAGCGAGCGAGCGCGCAGAGAGGGAGTGGCCAACTCCATC

```
ACTAGGGGTTCCTAGATCTGAATTCGGTACCCTAGTTATTAATAGTAATC
AATTACGGGGTCATTAGTTCATAGCCCATATATGGAGTTCCGCGTTACAT
AACTTACGGTAAATGGCCCGCCTGGCTGACCGCCCAACGACCCCCGCCCA
TTGACGTCAATAATGACGTATGTTCCCATAGTAACGCCAATAGGGACTTT
CCATTGACGTCAATGGGTGGACTATTTACGGTAAACTGCCCACTTGGCAG
TACATCAAGTGTATCATATGCCAAGTACGCCCCCTATTGACGTCAATGAC
GGTAAATGGCCCGCCTGGCATTATGCCCAGTACATGACCTTATGGGACTT
TCCTACTTGGCAGTACATCTACGTATTAGTCATCGCTATTACCATGGTCG
AGGTGAGCCCCACGTTCTGCTTCACTCTCCCCATCTCCCCCCCCTCCCCA
CCCCCAATTTTGTATTTATTTATTTTTAATTATTTTGTGCAGCGATGGG
GGCGGGGGGGGGGGGGGGCGCGCGCCAGGCGGGGCGGGGCGGGGCGAGG
GGCGGGGCGGGGCGAGGCGGAGAGGTGCGGCGGCAGCCAATCAGAGCGGC
GCGCTCCGAAAGTTTCCTTTTATGGCGAGGCGGCGGCGGCGGCGGCCCTA
TAAAAAGCGAAGCGCGCGGCGGGCGGGAGTCGCTGCGACGCTGCCTTCGC
CCCGTGCCCCGCTCCGCCGCCGCCTCGCGCCGCCCGCCCCGGCTCTGACT
GACCGCGTTACTCCCACAGGTGAGCGGGCGGGACGGCCCTTCTCCTCCGG
GCTGTAATTAGCGCTTGGTTTAATGACGGCTTGTTTCTTTTCTGTGGCTG
CGTGAAAGCCTTGAGGGGCTCCGGGAGGGCCCTTTGTGCGGGGGGGAGCG
GCTCGGGGGTGCGTGCGTGTGTGTGCGTGGGGAGCGCCGCGTGCGGC
CCGCGCTGCCCGGCGGCTGTGAGCGCTGCGGGCGCGGCGCGGGGCTTTGT
GCGCTCCGCAGTGTGCGCGAGGGGAGCGCGGCCGGGGCGGTGCCCCGCG
GTGCGGGGGGGCTGCGAGGGGAACAAAGGCTGCGTGCGGGTGTGTGCG
TGGGGGGTGAGCAGGGGTGTGGGCGCGGCGGTCGGGCTGTAACCCCCC
CCTGCACCCCCTCCCCGAGTTGCTGAGCACGGCCCGGCTTCGGGTGCGG
GGCTCCGTACGGGGCGTGGCGCGGGGCTCGCCGTGCCGGGCGGGGGTGG
CGGCAGGTGGGGGTGCCGGGCGGGGCGGGGCCGCCTCGGGCCGGGGAGGG
CTCGGGGAGGGGGCGCGGCGGCCCCCGGAGCGCCGGCGGCTGTCGAGGCG
CGGCGAGCCGCAGCCATTGCCTTTTATGGTAATCGTGCGAGAGGGCGCAG
GGACTTCCTTTGTCCCAAATCTGTGCGGAGCCGAAATCTGGGAGGCGCCG
CCGCACCCCCTCTAGCGGGCGCGGGGCGAAGCGGTGCGGCGCCGGCAGGA
AGGAAATGGGCGGGAGGGCCTTCGTGCGTCGCCGCGCCGCCGTCCCCTT
CTCCCTCTCCAGCCTCGGGGCTGTCCGCGGGGGACGGCTGCCTTCGGGG
GGGACGGGGCAGGGCGGGGTTCGGCTTCTGGCGTGTGACCGGCGGCTCTA
GAGCCTCTGCTAACCATGTTCATGCCTTCTTCTTTTTCCTACAGCTCCTG
GGCAACGTGCTGGTTATTGTGCTGTCTCATCATTTTGGCAAAGAATTCCT
CGAAGATCTAGGCCTGCAGGCGGCCGCCGCCACCATGAGCAAGGGCGAGG
AACTGTTCACTGGCGTGGTCCCAATTCTCGTGGAACTGGATGGCGATGTG
AATGGGCACAAATTTTCTGTCAGCGGAGAGGGTGAAGGTGATGCCACATA
CGGAAAGCTCACCCTGAAATTCATCTGCACCACTGGAAAGCTCCCTGTGC
CATGGCCAACACTGGTCACTACCCTGACCTATGGCGTGCAGTGCTTTTCC
AGATACCCAGACCATATGAAGCAGCATGACTTTTTCAAGAGCGCCATGCC
CGAGGGCTATGTGCAGGAGAGAACCATCTTTTTCAAAGATGACGGGAACT
ACAAGACCCGCGCTGAAGTCAAGTTCGAAGGTGACACCCTGGTGAATAGA
ATCGAGCTGAAGGGCATTGACTTTAAGGAGGATGGAAACATTCTCGGCCA
CAAGCTGGAATACAACTATAACTCCCACAATGTGTACATCATGGCCGACA
AGCAAAAGAATGGCATCAAGGTCAACTTCAAGATCAGACACAACATTGAG
GATGGATCCGTGCAGCTGGCCGACCATTATCAACAGAACACTCCAATCGG
CGACGGCCCTGTGCTCCTCCCAGACAACCATTACCTGTCCACCCAGTCTG
CCCTGTCTAAAGATCCCAACGAAAAGAGAGACCACATGGTCCTGCTGGAG
TTTGTGACCGCTGCTGGGATCACACATGGCATGGACGAGCTGTACAAGTG
AGCGGCCGCGGGGATCCAGACATGATAAGATACATTGATGAGTTTGGACA
AACCACAACTAGAATGCAGTGAAAAAAATGCTTTATTTGTGAAATTTGTG
ATGCTATTGCTTTATTTGTAACCATTATAAGCTGCAATAAACAAGTTAAC
AACAACAATTGCATTCATTTTATGTTTCAGGTTCAGGGGGAGGTGTGGGA
GGTTTTTTAGTCGACCTCGAGCAGTGTGGTTTTGCAAGAGGAAGCAAAAA
GCCTCTCCACCCAGGCCTGGAATGTTTCCACCCAAGTCGAAGGCAGTGTG
GTTTTGCAAGAGGAAGCAAAAAGCCTCTCCACCCAGGCCTGGAATGTTTC
CACCCAATGTCGAGCAACCCCGCCCAGCGTCTTGTCATTGGCGAATTCGA
ACACGCAGATGCAGTCGGGGCGGCGCGGTCCCAGGTCCACTTCGCATATT
AAGGTGACGCGTGTGGCCTCGAACACCGAGCGACCCTGCAGCCAATATGG
GATCGGCCATTGAACAAGATGGATTGCACGCAGGTTCTCCGGCCGCTTGG
GTGGAGAGGCTATTCGGCTATGACTGGGCACAACAGACAATCGGCTGCTC
TGATGCCGCCGTGTTCCGGCTGTCAGCGCAGGGGCGCCCGGTTCTTTTTG
TCAAGACCGACCTGTCCGGTGCCCTGAATGAACTGCAGGACGAGGCAGCG
CGGCTATCGTGGCTGGCCACGACGGGCGTTCCTTGCGCAGCTGTGCTCGA
CGTTGTCACTGAAGCGGGAAGGGACTGGCTGCTATTGGGCGAAGTGCCGG
GGCAGGATCTCCTGTCATCTCACCTTGCTCCTGCCGAGAAAGTATCCATC
ATGGCTGATGCAATGCGGCGGCTGCATACGCTTGATCCGGCTACCTGCCC
ATTCGACCACCAAGCGAAACATCGCATCGAGCGAGCACGTACTCGGATGG
AAGCCGGTCTTGTCGATCAGGATGATCTGGACGAAGAGCATCAGGGGCTC
GCGCCAGCCGAACTGTTCGCCAGGCTCAAGGCGCGCATGCCCGACGGCGA
GGATCTCGTCGTGACCCATGGCGATGCCTGCTTGCCGAATATCATGGTGG
AAAATGGCCGCTTTTCTGGATTCATCGACTGTGGCCGGCTGGGTGTGGCG
GACCGCTATCAGGACATAGCGTTGGCTACCCGTGATATTGCTGAAGAGCT
TGGCGGCGAATGGGCTGACCGCTTCCTCGTGCTTTACGGTATCGCCGCTC
CCGATTCGCAGCGCATCGCCTTCTATCGCCTTCTTGACGAGTTCTTCTGA
GGGGATCCGTCGACTAGAGCTCGCTGATCAGCCTCGACTGTGCCTTCTAG
TTGCCAGCCATCTGTTGTTTGCCCCTCCCCCGTGCCTTCCTTGACCCTGG
AAGGTGCCACTCCCACTGTCCTTTCCTAATAAAATGAGGAAATTGCATCG
CATTGTCTGAGTAGGTGTCATTCTATTCTGGGGGGTGGGGTGGGGCAGGA
CAGCAAGGGGGAGGATTGGGAAGACAATAGCAGGCATGCTGGGGAGAGAT
CTAGGAACCCCTAGTGATGGAGTTGGCCACTCCCTCTCTGCGCGCTCGCT
```

-continued
CGCTCACTGAGGCCGCCCGGGCAAAGCCCGGGCGTCGGGCGACCTTTGGT

CGCCCGGCCTCAGTGAGCGAGCGAGCGCGCAGAGAGGGAGTGGCCAACCC

CCCCCCCCCCCCCCCTGCAGCCCTGCATTAATGAATCGGCCAACGCGCGG

GGAGAGGCGGTTTGCGTATTGGGCGCTCTTCCGCTTCCTCGCTCACTGAC

TCGCTGCGCTCGGTCGTTCGGCTGCGGCGAGCGGTATCAGCTCACTCAAA

GGCGGTAATACGGTTATCCACAGAATCAGGGGATAACGCAGGAAAGAACA

TGTGAGCAAAAGGCCAGCAAAAGGCCAGGAACCGTAAAAAGGCCGCGTTG

CTGGCGTTTTTCCATAGGCTCCGCCCCCCTGACGAGCATCACAAAAATCG

ACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCG

CTTACCGGATACCTGTCCGCCTTTCTCCCTTCGGGAAGCGTGGCGCTTTC

TCAATGCTCACGCTGTAGGTATCTCAGTTCGGTGTAGGTCGTTCGCTCCA

AGCTGGGCTGTGTGCACGAACCCCCCGTTCAGCCCGACCGCTGCGCCTTA

TCCGGTAACTATCGTCTTGAGTCCAACCCGGTAAGACACGACTTATCGCC

ACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGG

ACAGTATTTGGTATCTGCGCTCTGCTGAAGCCAGTTACCTTCGGAAAAAG

AGTTGGTAGCTCTTGATCCGGCAAACAAACCACCGCTGGTAGCGGTGGTT

TTTTTGTTTGCAAGCAGCAGATTACGCGCAGAAAAAAAGGATCTCAAGAA

GATCCTTTGATCTTTTCTACGGGGTCTGACGCTCAGTGGAACGAAAACTC

ACGTTAAGGGATTTTGGTCATGAGATTATCAAAAGGATCTTCACCTAGA

TCCTTTTAAATTAAAAATGAAGTTTTAAATCAATCTAAAGTATATATGAG

TAAACTTGGTCTGACAGTTACCAATGCTTAATCAGTGAGGCACCTATCTC

AGCGATCTGTCTATTTCGTTCATCCATAGTTGCCTGACTCCCCGTCGTGT

AGATAACTACGATACGGGAGGGCTTACCATCTGGCCCCAGTGCTGCAATG

ATACCGCGAGACCCACGCTCACCGGCTCCAGATTTATCAGCAATAAACCA

GCCAGCCGGAAGGGCCGAGCGCAGAAGTGGTCCTGCAACTTTATCCGCCT

CCATCCAGTCTATTAATTGTTGCCGGGAAGCTAGAGTAAGTAGTTCGCCA

GTTAATAGTTTGCGCAACGTTGTTGCCATTGCTACAGGCATCGTGGTGTC

ACGCTCGTCGTTTGGTATGGCTTCATTCAGCTCCGGTTCCCAACGATCAA

GGCGAGTTACATGATCCCCCATGTTGTGCAAAAAAGCGGTTAGCTCCTTC

GGTCCTCCGATCGTTGTCAGAAGTAAGTTGGCCGCAGTGTTATCACTCAT

GGTTATGGCAGCACTGCATAATTCTCTTACTGTCATGCCATCCGTAAGAT

GCTTTTCTGTGACTGGTGAGTACTCAACCAAGTCATTCTGAGAATAGTGT

ATGCGGCGACCGAGTTGCTCTTGCCCGGCGTCAATACGGGATAATACCGC

GCCACATAGCAGAACTTTAAAAGTGCTCATCATTGGAAAACGTTCTTCGG

GGCGAAAACTCTCAAGGATCTTACCGCTGTTGAGATCCAGTTCGATGTAA

CCCACTCGTGCACCCAACTGATCTTCAGCATCTTTTACTTTCACCAGCGT

TTCTGGGTGAGCAAAAACAGGAAGGCAAAATGCCGCAAAAAAGGGAATAA

GGGCGACACGGAAATGTTGAATACTCATACTCTTCCTTTTTCAATATTAT

TGAAGCATTTATCAGGGTTATTGTCTCATGAGCGGATACATATTTGAATG

-continued
TATTTAGAAAAATAAACAAATAGGGGTTCCGCGCACATTTCCCCGAAAAG

TGCCACCTGACGTCTAAGAAACCATTATTATCATGACATTAACCTATAAA

AATAGGCGTATCACGAGGCCCTTTCGTCTCGCGCGTTTCGGTGATGACGG

TGAAAACCTCTGACACATGCAGCTCCCGGAGACGGTCACAGCTTGTCTGT

AAGCGGATGCCGGGAGCAGACAAGCCCGTCAGGGCGCGTCAGCGGGTGTT

GGCGGGTGTCGGGGCTGGCTTAACTATGCGGCATCAGAGCAGATTGTACT

GAGAGTGCACCATATGCGGTGTGAAATACCGCACAGATGCGTAAGGAGAA

AATACCGCATCAGGAAATTGTAAACGTTAATATTTTGTTAAAATTCGCGT

TAAATTTTTGTTAAATCAGCTCATTTTTTAACCAATAGGCCGAAATCGGC

AAAATCCCTTATAAATCAAAAGAATAGACCGAGATAGGGTTGAGTGTTGT

TCCAGTTTGGAACAAGAGTCCACTATTAAAGAACGTGGACTCCAACGTCA

AAGGGCGAAAAACCGTCTATCAGGGCGATGGCCCACTACGTGAACCATCA

CCCTAATCAAGTTTTTTGGGGTCGAGGTGCCGTAAAGCACTAAATCGGAA

CCCTAAAGGGAGCCCCCGATTTAGAGCTTGACGGGGAAAGCCGGCGAACG

TGGCGAGAAAGGAAGGGAAGAAAGCGAAAGGAGCGGGCGCTAGGGCGCTG

GCAAGTGTAGCGGTCACGCTGCGCGTAACCACCACACCCGCCGCGCTTAA

TGCGCCGCTACAGGGCGCGTCGCGCCATTCGCCATTCAGGCTACGCAACT

GTTGGGAAGGGCGATCGGTGCGGGCCTCTTCGCTATTACGCCAGGCTGCA

The red fluorescent protein mCherry was cloned in lieu of GFP in the pTRUF11 construct using standard techniques. mCherry was amplified from pRSETB-mCherry (obtained from Dr. R. Tsien, University of California, San Diego) using primers mcherryNotI-F 3'ATAAGAATGCGGCCGC-CACCATGGTGAG (SEQ ID NO: 3) and mcherryNotI-R 3' ATAAGAATGCGGCCGCCCACGATGGTGTAGTCC (SEQ ID NO: 4) to introduce two Not I sites flanking the amplicon. The amplicon was digested with NotI and ligated into pTRUF11 NotI. A human codon-optimized acid α-glucosidase cDNA (coGAA) (GENEART®, LIFE TECHNOLOGIES) was cloned into a desmin promoter construct (pTR-DES) previously described (Pacak et al., 2009; Falk et al., 2013). The liver-specific promoter (LSP) (GENEART®, LIFE TECHNOLOGIES™) contains the apolipoprotein E—hepatocyte control region (Miao et al., 2000; Manno et al., 2006; Cao et al., 2007), the human α1-antitrypsin promoter (Cresawn et al., 2005) and 5' UTR and was sub-cloned into pTR-DES-coGAA in lieu of the DES promoter (BglII and SalI). The sequences of the DES promoter and the LSP are provided below.

DES Promoter
(SEQ ID NO: 5)
5'-GATCTTACCCCCTGCCCCCCACAGCTCCTCTCCTGTGCCTTGTT

TCCCAGCCATGCGTTCTCCTCTATAAATACCCGCTCTGGTATTTGGGTT

GGCAGCTGTTGCTGCCAGGGAGATGGTTGGGTTGACATGCGGCTCCTGAC

AAAACACAAACCCCTGGTGTGTGTGGGCGTGGGTGGTGTGAGTAGGGGA

TGAATCAGGGAGGGGGCGGGGACCCAGGGGGCAGGAGCCACACAAAGTC

TGTGCGGGGTGGGAGCGCACATAGCAATTGGAAACTGAAAGCTTATCAG

ACCCTTTCTGGAAATCAGCCCACTGTTTATAAACTTGAGGCCCCACCCTC

-continued
GAGATAACCAGGGCTGAAAGAGGCCCGCCTGGGGGCTGGAGACATGCTTG

CTGCCTGCCCTGGCGAAGGATTGGCAGGCTTGCCCGTCACAGGACCCCCG

CTGGCTGACTCAGGGGCGCAGGCCTCTTGCGGGGGAGCTGGCCTCCCCGC

CCCCACGGCCACGGGCCGCCCTTTCCTGGCAGGACAGCGGGATCTTGCAG

CTGTCAGGGGAGGGAGGCGGGGGCTGATGTCAGGAGGGATACAAATAGT

GCCGACGGCTGGGGGCCCTGTCTCCCCTCGCCGCATCCACTCTCCGGCCG

GCCGCCTGTCCGCCGCCTCCTCCGTGCGCCCGCCAGCCTCGCCCGCGCCG

TCACCGTGAGGCACTGGG

ApoE-HCR-hAAT-5'UTR [Liver Specific Promoter
(LSP)] Sequence:
(SEQ ID NO: 6)
5'-CCCTAAAATGGGCAAACATTGCAAGCAGCAAACAGCAAACACAC

AGCCCTCCCTGCCTGCTGACCTTGGAGCTGGGGCAGAGGTCAGAGACCTC

TCTGGGGACTGTCCCAGGTCAGTGGTGGTGCCTGAAGCTGAGGAGACAGG

GCCCTGTCCTCGTCCGTATTTAAGCAGTGGATCCAGAGGGGCAACGGGGG

AGGCTGCTGGTGAATATTAACCAAGGTCACCCCAGTTATCGGAGGAGCAA

-continued
ACAGGGGCTAAGTCCACTGGCTGGGATCTGAGTCGCCCGCCTACGCTGCC

CGGACGCTTTGCCTGGGCAGTGTACAGCTTCCACTGCACTTACCGAAAGG

AGTCATTGTAGGGCCCTGTCTCCTCAGCTTCAGGCACCACCACTGACCTG

GGACAGTGAATCCGGA

AAV9 Production

Recombinant adeno-associated viral (AAV) vectors were produced and purified as previously described (Zolotukhin et al., 2002). HEK293 cells were cultured in 5% FBS and antibiotic supplemented Dulbecco's modified Eagle's medium. Plasmid DNA was propagated in SURE2 cells (Agilent Technologies, Inc., Santa Clara, Calif.) and isolated using Qiagen plasmid purification reagents or obtained from Aldevron (Fargo, N. Dak.). Cells were seeded in 150 mm dishes at $5.0\times10^6$ cells 24 hours prior to transfection. The calcium phosphate precipitate was formed by combining the total amount of expression plasmids, with the equivalent concentration of the capsid plasmid rep2/cap9 and twice the concentration of the Ad helper plasmid pXX6-80 in 2.5M $CaCl_2$) followed by the addition of 2×HBS, pH 7.05. Sequences of these plasmids are below.

rep2/cap9 Sequence:
(SEQ ID NO: 7)
5'-TCGAGGACAACCTTAGTGAAGGAATTCGCGAGTGGTGGGCTTTGAAACCTGGAG

CCCCTCAACCCAAGGCAAATCAACAACATCAAGACAACGCTCGAGGTCTTGTGC

TTCCGGGTTACAAATACCTTGGACCCGGCAACGGACTCGACAAGGGGGAGCCGG

TCAACGCAGCAGACGCGGCGGCCCTCGAGCACGACAAGGCCTACGACCAGCAGC

TCAAGGCCGGAGACAACCCGTACCTCAAGTACAACCACGCCGACGCCGAGTTCC

AGGAGCGGCTCAAAGAAGATACGTCTTTTGGGGGCAACCTCGGGCGAGCAGTCT

TCCAGGCCAAAAAGAGGCTTCTTGAACCTCTTGGTCTGGTTGAGGAAGCGGCTAA

GACGGCTCCTGGAAAGAAGAGGCCTGTAGAGCAGTCTCCTCAGGAACCGGACTC

CTCCGCGGGTATTGGCAAATCGGGTGCACAGCCCGCTAAAAAGAGACTCAATTT

CGGTCAGACTGGCGACACAGAGTCAGTCCCAGACCCTCAACCAATCGGAGAACC

TCCCGCAGCCCCCTCAGGTGTGGGATCTCTTACAATGGCTTCAGGTGGTGGCGCA

CCAGTGGCAGACAATAACGAAGGTGCCGATGGAGTGGGTAGTTCCTCGGGAAAT

TGGCATTGCGATTCCCAATGGCTGGGGGACAGAGTCATCACCACCAGCACCCGA

ACCTGGGCCCTGCCCACCTACAACAATCACCTCTACAAGCAAATCTCCAACAGCA

CATCTGGAGGATCTTCAAATGACAACGCCTACTTCGGCTACAGCACCCCCTGGGG

GTATTTTGACTTCAACAGATTCCACTGCCACTTCTCACCACGTGACTGGCAGCGA

CTCATCAACAACAACTGGGGATTCCGGCCTAAGCGACTCAACTTCAAGCTCTTCA

ACATTCAGGTCAAAGAGGTTACGGACAACAATGGAGTCAAGACCATCGCCAATA

ACCTTACCAGCACGGTCCAGGTCTTCACGGACTCAGACTATCAGCTCCCGTACGT

GCTCGGGTCGGCTCACGAGGGCTGCCTCCCGCCGTTCCCAGCGGACGTTTTCATG

ATTCCTCAGTACGGGTATCTGACGCTTAATGATGGAAGCCAGGCCGTGGGTCGTT

CGTCCTTTTACTGCCTGGAATATTTCCCGTCGCAAATGCTAAGAACGGGTAACAA

CTTCCAGTTCAGCTACGAGTTTGAGAACGTACCTTTCCATAGCAGCTACGCTCAC

-continued

```
AGCCAAAGCCTGGACCGACTAATGAATCCACTCATCGACCAATACTTGTACTATC

TCTCAAAGACTATTAACGGTTCTGGACAGAATCAACAAACGCTAAAATTCAGTGT

GGCCGGACCCAGCAACATGGCTGTCCAGGGAAGAAACTACATACCTGGACCCAG

CTACCGACAACAACGTGTCTCAACCACTGTGACTCAAAACAACAACAGCGAATT

TGCTTGGCCTGGAGCTTCTTCTTGGGCTCTCAATGGACGTAATAGCTTGATGAAT

CCTGGACCTGCTATGGCCAGCCACAAAGAAGGAGAGGACCGTTTCTTTCCTTTGT

CTGGATCTTTAATTTTTGGCAAACAAGGAACTGGAAGAGACAACGTGGATGCGG

ACAAAGTCATGATAACCAACGAAGAAGAAATTAAAACTACTAACCCGGTAGCAA

CGGAGTCCTATGGACAAGTGGCCACAAACCACCAGAGTGCCCAAGCACAGGCGC

AGACCGGCTGGGTTCAAAACCAAGGAATACTTCCGGGTATGGTTTGGCAGGACA

GAGATGTGTACCTGCAAGGACCCATTTGGGCCAAAATTCCTCACACGGACGGCA

ACTTTCACCCTTCTCCGCTGATGGGAGGGTTTGGAATGAAGCACCCGCCTCCTCA

GATCCTCATCAAAAACACACCTGTACCTGCGGATCCTCCAACGGCCTTCAACAAG

GACAAGCTGAACTCTTTCATCACCCAGTATTCTACTGGCCAAGTCAGCGTGGAGA

TCGAGTGGGAGCTGCAGAAGGAAAACAGCAAGCGCTGGAACCCGGAGATCCAG

TACACTTCCAACTATTACAAGTCTAATAATGTTGAATTTGCTGTTAATACTGAAG

GTGTATATAGTGAACCCCGCCCCATTGGCACCAGATACCTGACTCGTAATCTGTA

ATTGCTTGTTAATCAATAAACCGTTTAATTCGTTTCAGTTGAACTTTGGTCTCTGC

GAAGGGCGAATTCGTTTAAACCTGCAGGACTAGAGTCCTGTATTAGAGGTCACGT

GAGTGTTTTGCGACATTTTGCGACACCATGTGGTCACGCTGGGTATTTAAGCCCG

AGTGAGCACGCAGGGTCTCCATTTTGAAGCGGGAGGTTTGAACGCGCAGCCGCC

AAGCCGAATTCTGCAGATATCCATCACACTGGCGGCCGCTCGACTAGAGCGGCC

GCCACCGCGGTGGAGCTCCAGCTTTTGTTCCCTTTAGTGAGGGTTAATTGCGCGC

TTGGCGTAATCATGGTCATAGCTGTTTCCTGTGTGAAATTGTTATCCGCTCACAAT

TCCACACAACATACGAGCCGGAAGCATAAAGTGTAAAGCCTGGGGTGCCTAATG

AGTGAGCTAACTCACATTAATTGCGTTGCGCTCACTGCCCGCTTTCCAGTCGGGA

AACCTGTCGTGCCAGCTGCATTAATGAATCGGCCAACGCGCGGGGAGAGGCGGT

TTGCGTATTGGGCGCTCTTCCGCTTCCTCGCTCACTGACTCGCTGCGCTCGGTCGT

TCGGCTGCGGCGAGCGGTATCAGCTCACTCAAAGGCGGTAATACGGTTATCCAC

AGAATCAGGGGATAACGCAGGAAAGAACATGTGAGCAAAAGGCCAGCAAAAGG

CCAGGAACCGTAAAAAGGCCGCGTTGCTGGCGTTTTTCCATAGGCTCCGCCCCCC

TGACGAGCATCACAAAAATCGACGCTCAAGTCAGAGGTGGCGAAACCCGACAGG

ACTATAAAGATACCAGGCGTTTCCCCCTGGAAGCTCCCTCGTGCGCTCTCCTGTT

CCGACCCTGCCGCTTACCGGATACCTGTCCGCCTTTCTCCCTTCGGGAAGCGTGG

CGCTTTCTCATAGCTCACGCTGTAGGTATCTCAGTTCGGTGTAGGTCGTTCGCTCC

AAGCTGGGCTGTGTGCACGAACCCCCCGTTCAGCCCGACCGCTGCGCCTTATCCG

GTAACTATCGTCTTGAGTCCAACCCGGTAAGACACGACTTATCGCCACTGGCAGC

AGCCACTGGTAACAGGATTAGCAGAGCGAGGTATGTAGGCGGTGCTACAGAGTT

CTTGAAGTGGTGGCCTAACTACGGCTACACTAGAAGGACAGTATTTGGTATCTGC

GCTCTGCTGAAGCCAGTTACCTTCGGAAAAAGAGTTGGTAGCTCTTGATCCGGCA

AACAAACCACCGCTGGTAGCGGTGGTTTTTTTGTTTGCAAGCAGCAGATTACGCG
```

-continued

```
CAGAAAAAAAGGATCTCAAGAAGATCCTTTGATCTTTTCTACGGGGTCTGACGCT

CAGTGGAACGAAAACTCACGTTAAGGGATTTTGGTCATGAGATTATCAAAAAGG

ATCTTCACCTAGATCCTTTTAAATTAAAAATGAAGTTTTAAATCAATCTAAAGTA

TATATGAGTAAACTTGGTCTGACAGTTACCAATGCTTAATCAGTGAGGCACCTAT

CTCAGCGATCTGTCTATTTCGTTCATCCATAGTTGCCTGACTCCCCGTCGTGTAGA

TAACTACGATACGGGAGGGCTTACCATCTGGCCCCAGTGCTGCAATGATACCGCG

AGACCCACGCTCACCGGCTCCAGATTTATCAGCAATAAACCAGCCAGCCGGAAG

GGCCGAGCGCAGAAGTGGTCCTGCAACTTTATCCGCCTCCATCCAGTCTATTAAT

TGTTGCCGGGAAGCTAGAGTAAGTAGTTCGCCAGTTAATAGTTTGCGCAACGTTG

TTGCCATTGCTACAGGCATCGTGGTGTCACGCTCGTCGTTTGGTATGGCTTCATTC

AGCTCCGGTTCCCAACGATCAAGGCGAGTTACATGATCCCCCATGTTGTGCAAAA

AAGCGGTTAGCTCCTTCGGTCCTCCGATCGTTGTCAGAAGTAAGTTGGCCGCAGT

GTTATCACTCATGGTTATGGCAGCACTGCATAATTCTCTTACTGTCATGCCATCCG

TAAGATGCTTTCTGTGACTGGTGAGTACTCAACCAAGTCATTCTGAGAATAGTGT

ATGCGGCGACCGAGTTGCTCTTGCCCGGCGTCAATACGGGATAATACCGCGCCAC

ATAGCAGAACTTTAAAAGTGCTCATCATTGGAAAACGTTCTTCGGGGCGAAAACT

CTCAAGGATCTTACCGCTGTTGAGATCCAGTTCGATGTAACCCACTCGTGCACCC

AACTGATCTTCAGCATCTTTTACTTTCACCAGCGTTTCTGGGTGAGCAAAAACAG

GAAGGCAAAATGCCGCAAAAAAGGGAATAAGGGCGACACGGAAATGTTGAATA

CTCATACTCTTCCTTTTTCAATATTATTGAAGCATTTATCAGGGTTATTGTCTCAT

GAGCGGATACATATTTGAATGTATTTAGAAAAATAAACAAATAGGGGTTCCGCG

CACATTTCCCCGAAAAGTGCCACCTAAATTGTAAGCGTTAATATTTTGTTAAAAT

TCGCGTTAAATTTTTGTTAAATCAGCTCATTTTTTAACCAATAGGCCGAAATCGGC

AAAATCCCTTATAAATCAAAAGAATAGACCGAGATAGGGTTGAGTGTTGTTCCA

GTTTGGAACAAGAGTCCACTATTAAAGAACGTGGACTCCAACGTCAAAGGGCGA

AAAACCGTCTATCAGGGCGATGGCCCACTACGTGAACCATCACCCTAATCAAGTT

TTTTGGGGTCGAGGTGCCGTAAAGCACTAAATCGGAACCCTAAAGGGAGCCCCC

GATTTAGAGCTTGACGGGGAAAGCCGGCGAACGTGGCGAGAAAGGAAGGGAAG

AAAGCGAAAGGAGCGGGCGCTAGGGCGCTGGCAAGTGTAGCGGTCACGCTGCGC

GTAACCACCACACCCGCCGCGCTTAATGCGCCGCTACAGGGCGCGTCCCATTCGC

CATTCAGGCTGCGCAACTGTTGGGAAGGGCGATCGGTGCGGGCCTCTTCGCTATT

ACGCCAGCTGGCGAAAGGGGGATGTGCTGCAAGGCGATTAAGTTGGGTAACGCC

AGGGTTTTCCCAGTCACGACGTTGTAAAACGACGGCCAGTGAGCGCGCGTAATA

CGACTCACTATAGGGCGAATTGGGTACCGGGCCCCCCCTCGATCGAGGTCGACG

GTATCGGGGGAGCTCGGATCCACTAGTAACGGCCGCCAGTGTGCTGGATTCGGCT

TTATTTAAGCCCGAGTGAGCACGCAGGGTCTCCATTTTGAAGCGGGAGGTTTGAA

CGCGCAGCCGCCATGCCGGGGTTTTACGAGATTGTGATTAAGGTCCCCAGCGACC

TTGACGGGCATCTGCCCGGCATTTCTGACAGCTTTGTGAACTGGGTGGCCGAGAA

GGAATGGGAGTTGCCGCCAGATTCTGACATGGATCTGAATCTGATTGAGCAGGC

ACCCCTGACCGTGGCCGAGAAGCTGCAGCGCGACTTTCTGACGGAATGGCGCCG

TGTGAGTAAGGCCCCGGAGGCCCTTTTCTTTGTGCAATTTGAGAAGGGAGAGAGC
```

-continued

```
TACTTCCACATGCACGTGCTCGTGGAAACCACCGGGGTGAAATCCATGGTTTTGG
GACGTTTCCTGAGTCAGATTCGCGAAAAACTGATTCAGAGAATTTACCGCGGGAT
CGAGCCGACTTTGCCAAACTGGTTCGCGGTCACAAAGACCAGAAATGGCGCCGG
AGGCGGGAACAAGGTGGTGGATGAGTGCTACATCCCCAATTACTTGCTCCCCAA
AACCCAGCCTGAGCTCCAGTGGGCGTGGACTAATATGGAACAGTATTTAAGCGC
CTGTTTGAATCTCACGGAGCGTAAACGGTTGGTGGCGCAGCATCTGACGCACGTG
TCGCAGACGCAGGAGCAGAACAAAGAGAATCAGAATCCCAATTCTGATGCGCCG
GTGATCAGATCAAAAACTTCAGCCAGGTACATGGAGCTGGTCGGGTGGCTCGTG
GACAAGGGGATTACCTCGGAGAAGCAGTGGATCCAGGAGGACCAGGCCTCATAC
ATCTCCTTCAATGCGGCCTCCAACTCGCGGTCCCAAATCAAGGCTGCCTTGGACA
ATGCGGGAAAGATTATGAGCCTGACTAAAACCGCCCCCGACTACCTGGTGGGCC
AGCAGCCCGTGGAGGACATTTCCAGCAATCGGATTTATAAAATTTTGGAACTAAA
CGGGTACGATCCCCAATATGCGGCTTCCGTCTTTCTGGGATGGGCCACGAAAAAG
TTCGGCAAGAGGAACACCATCTGGCTGTTTGGGCCTGCAACTACCGGGAAGACC
AACATCGCGGAGGCCATAGCCCACACTGTGCCCTTCTACGGGTGCGTAAACTGG
ACCAATGAGAACTTTCCCTTCAACGACTGTGTCGACAAGATGGTGATCTGGTGGG
AGGAGGGGAAGATGACCGCCAAGGTCGTGGAGTCGGCCAAAGCCATTCTCGGAG
GAAGCAAGGTGCGCGTGGACCAGAAATGCAAGTCCTCGGCCCAGATAGACCCGA
CTCCCGTGATCGTCACCTCCAACACCAACATGTGCGCCGTGATTGACGGGAACTC
AACGACCTTCGAACACCAGCAGCCGTTGCAAGACCGGATGTTCAAATTTGAACTC
ACCCGCCGTCTGGATCATGACTTTGGGAAGGTCACCAAGCAGGAAGTCAAAGAC
TTTTTCCGGTGGGCAAAGGATCACGTGGTTGAGGTGGAGCATGAATTCTACGTCA
AAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCT
TCGATCAACTACGCGGACAGGTACCAAAACAAATGTTCTCGTCACGTGGGCATG
AATCTGATGCTGTTTCCCTGCAGACAATGCGAGAGACTGAATCAGAATTCAAATA
TCTGCTTCACTCACGGTGTCAAAGACTGTTTAGAGTGCTTTCCCGTGTCAGAATCT
CAACCCGTTTCTGTCGTCAAAAAGGCGTATCAGAAACTGTGCTACATTCATCACA
TCATGGGAAAGGTGCCAGACGCTTGCACTGCTTGCGACCTGGTCAATGTGGACTT
GGATGACTGTGTTTCTGAACAATAAATGACTTAAACCAGGTATGGCTGCCGATGG
TTATCTTCCAGATTGGC
``` pXX6-80 Sequence:
(SEQ ID NO: 8)
```
5'-TCTTCCGCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCATCACAA
AAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTA
CCGGATACCTGTCCGCCTTTCTCCCTTCGGGAAGCGTGGCGCTTTCTCATAGCTCA
CGCTGTAGGTATCTCAGTTCGGTGTAGGTCGTTCGCTCCAAGCTGGGCTGTGTGC
ACGAACCCCCCGTTCAGCCCGACCGCTGCGCCTTATCCGGTAACTATCGTCTTGA
```

-continued

```
GTCCAACCCGGTAAGACACGACTTATCGCCACTGGCAGCAGCCACTGGTAACAG

GATTAGCAGAGCGAGGTATGTAGGCGGTGCTACAGAGTTCTTGAAGTGGTGGCC

TAACTACGGCTACACTAGAAGAACAGTATTTGGTATCTGCGCTCTGCTGAAGCCA

GTTACCTTCGGAAAAAGAGTTGGTAGCTCTTGATCCGGCAAACAAACCACCGCTG

GTAGCGGTGGTTTTTTTGTTTGCAAGCAGCAGATTACGCGCAGAAAAAAAGGATC

TCAAGAAGATCCTTTGATCTTTTCTACGGGGTCTGACGCTCAGTGGAACGAAAAC

TCACGTTAAGGGATTTTGGTCATGAGATTATCAAAAAGGATCTTCACCTAGATCC

TTTTAAATTAAAAATGAAGTTTTAAATCAATCTAAAGTATATATGAGTAAACTTG

GTCTGACAGTTACCAATGCTTAATCAGTGAGGCACCTATCTCAGCGATCTGTCTA

TTTCGTTCATCCATAGTTGCCTGACTCCCCGTCGTGTAGATAACTACGATACGGG

AGGGCTTACCATCTGGCCCCAGTGCTGCAATGATACCGCGAGACCCACGCTCACC

GGCTCCAGATTTATCAGCAATAAACCAGCCAGCCGGAAGGGCCGAGCGCAGAAG

TGGTCCTGCAACTTTATCCGCCTCCATCCAGTCTATTAATTGTTGCCGGGAAGCTA

GAGTAAGTAGTTCGCCAGTTAATAGTTTGCGCAACGTTGTTGCCATTGCTACAGG

CATCGTGGTGTCACGCTCGTCGTTTGGTATGGCTTCATTCAGCTCCGGTTCCCAAC

GATCAAGGCGAGTTACATGATCCCCCATGTTGTGCAAAAAAGCGGTTAGCTCCTT

CGGTCCTCCGATCGTTGTCAGAAGTAAGTTGGCCGCAGTGTTATCACTCATGGTT

ATGGCAGCACTGCATAATTCTCTTACTGTCATGCCATCCGTAAGATGCTTTTCTGT

GACTGGTGAGTACTCAACCAAGTCATTCTGAGAATAGTGTATGCGGCGACCGAG

TTGCTCTTGCCCGGCGTCAATACGGGATAATACCGCGCCACATAGCAGAACTTTA

AAAGTGCTCATCATTGGAAAACGTTCTTCGGGGCGAAAACTCTCAAGGATCTTAC

CGCTGTTGAGATCCAGTTCGATGTAACCCACTCGTGCACCCAACTGATCTTCAGC

ATCTTTTACTTTCACCAGCGTTTCTGGGTGAGCAAAAACAGGAAGGCAAAATGCC

GCAAAAAAGGGAATAAGGGCGACACGGAAATGTTGAATACTCATACTCTTCCTT

TTTCAATATTATTGAAGCATTTATCAGGGTTATTGTCTCATGAGCGGATACATATT

TGAATGTATTTAGAAAAATAAACAAATAGGGGTTCCGCGCACATTTCCCCGAAA

AGTGCCACCTGACGTCTAAGAAACCATTATTATCATGACATTAACCTATAAAAAT

AGGCGTATCACGAGGCCCTTTCGTCTCGCGCGTTTCGGTGATGACGGTGAAAACC

TCTGACACATGCAGCTCCCGGAGACGGTCACAGCTTGTCTGTAAGCGGATGCCGG

GAGCAGACAAGCCCGTCAGGGCGCGTCAGCGGGTGTTGGCGGGTGTCGGGCTG

GCTTAACTATGCGGCATCAGAGCAGATTGTACTGAGAGTGCACCATAAAATTGTA

AACGTTAATATTTTGTTAAAATTCGCGTTAAATTTTGTTAAATCAGCTCATTTTT

TAACCAATAGGCCGAAATCGGCAAAATCCCTTATAAATCAAAAGAATAGCCCGA

GATAGGGTTGAGTGTTGTTCCAGTTTGGAACAAGAGTCCACTATTAAAGAACGTG

GACTCCAACGTCAAAGGGCGAAAAACCGTCTATCAGGGCGATGGCCCACTACGT

GAACCATCACCCAAATCAAGTTTTTTGGGGTCGAGGTGCCGTAAAGCACTAAATC

GGAACCCTAAAGGGAGCCCCCGATTTAGAGCTTGACGGGGAAAGCCGGCGAACG

TGGCGAGAAAGGAAGGGAAGAAAGCGAAAGGAGCGGGCGCTAGGGCGCTGGCA

AGTGTAGCGGTCACGCTGCGCGTAACCACCACACCCGCCGCGCTTAATGCGCCGC

TACAGGGCGCGTACTATGGTTGCTTTGACGTATGCGGTGTGAAATACCGCACAGA

TGCGTAAGGAGAAAATACCGCATCAGGCGCCATTCGCCATTCAGGCTGCGCAAC
```

-continued

```
TGTTGGGAAGGGCGATCGGTGCGGGCCTCTTCGCTATTACGCCAGCTGGCGAAA
GGGGGATGTGCTGCAAGGCGATTAAGTTGGGTAACGCCAGGGTTTTCCCAGTCA
CGACGTTGTAAAACGACGGCCAGTGCCAAGCTTAAGGTGCACGGCCCACGTGGC
CACTAGTACTTCTCGACAGAAGCACCATGTCCTTGGGTCCGGCCTGCTGAATGCG
CAGGCGGTCGGCCATGCCCCAGGCTTCGTTTTGACATCGGCGCAGGTCTTTGTAG
TAGTCTTGCATGAGCCTTTCTACCGGCACTTCTTCTTCTCCTTCCTCTTGTCCTGCA
TCTCTTGCATCTATCGCTGCGGCGGCGGCGGAGTTTGGCCGTAGGTGGCGCCCTC
TTCCTCCCATGCGTGTGACCCCGAAGCCCCTCATCGGCTGAAGCAGGGCTAGGTC
GGCGACAACGCGCTCGGCTAATATGGCCTGCTGCACCTGCGTGAGGGTAGACTG
GAAGTCATCCATGTCCACAAAGCGGTGGTATGCGCCCGTGTTGATGGTGTAAGTG
CAGTTGGCCATAACGGACCAGTTAACGGTCTGGTGACCCGGCTGCGAGAGCTCG
GTGTACCTGAGACGCGAGTAAGCCCTCGAGTCAAATACGTAGTCGTTGCAAGTCC
GCACCAGGTACTGGTATCCCACCAAAAAGTGCGGCGGCGGCTGGCGGTAGAGGG
GCCAGCGTAGGGTGGCCGGGGCTCCGGGGGCGAGATCTTCCAACATAAGGCGAT
GATATCCGTAGATGTACCTGGACATCCAGGTGATGCCGGCGGCGGTGGTGGAGG
CGCGCGGAAAGTCGCGGACGCGGTTCCAGATGTTGCGCAGCGGCAAAAAGTGCT
CCATGGTCGGGACGCTCTGGCCGGTCAGGCGCGCAATCGTTGACGCTCTACCG
TGCAAAAGGAGAGCCTGTAAGCGGGCACTCTTCCGTGGTCTGGTGGATAAATTC
GCAAGGGTATCATGGCGGACGACCGGGGTTCGAGCCCCGTATCCGGCCGTCCGC
CGTGATCCATGCGGTTACCGCCCGCGTGTCGAACCCAGGTGTGCGACGTCAGACA
ACGGGGGAGTGCTCCTTTTGGCTTCCTTCCAGGCGCGGCGGCTGCTGCGCTAGCT
TTTTTGGCCACTGGCCGCGCGCAGCGTAAGCGGTTAGGCTGGAAAGCGAAAGCA
TTAAGTGGCTCGCTCCCTGTAGCCGGAGGGTTATTTTCCAAGGGTTGAGTCGCGG
GACCCCCGGTTCGAGTCTCGGACCGGCCGGACTGCGGCGAACGGGGGTTTGCCT
CCCCGTCATGCAAGACCCCGCTTGCAAATTCCTCCGGAAACAGGGACGAGCCCCT
TTTTTGCTTTTCCCAGATGCATCCGGTGCTGCGGCAGATGCGCCCCCCTCCTCAGC
AGCGGCAAGAGCAAGAGCAGCGGCAGACATGCAGGGCACCCTCCCCTCCTCCTA
CCGCGTCAGGAGGGGCGACATCCGCGGTTGACGCGGCAGCAGATGGTGATTACG
AACCCCCGCGGCGCCGGGCCCGGCACTACCTGGACTTGGAGGAGGGCGAGGGCC
TGGCGCGGCTAGGAGCGCCCTCTCCTGAGCGGTACCCAAGGGTGCAGCTGAAGC
GTGATACGCGTGAGGCGTACGTGCCGCGGCAGAACCTGTTTCGCGACCGCGAGG
GAGAGGAGCCCGAGGAGATGCGGGATCGAAAGTTCCACGCAGGGCGCGAGCTG
CGGCATGGCCTGAATCGCGAGCGGTTGCTGCGCGAGGAGGACTTTGAGCCCGAC
GCGCGAACCGGGATTAGTCCCGCGCGCGCACACGTGGCGGCCGCCGACCTGGTA
ACCGCATACGAGCAGACGGTGAACCAGGAGATTAACTTTCAAAAAAGCTTTAAC
AACCACGTGCGTACGCTTGTGGCGCGCGAGGAGGTGGCTATAGGACTGATGCAT
CTGTGGGACTTTGTAAGCGCGCTGGAGCAAAACCCAAATAGCAAGCCGCTCATG
GCGCAGCTGTTCCTTATAGTGCAGCACAGCAGGGACAACGAGGCATTCAGGGAT
GCGCTGCTAAACATAGTAGAGCCCGAGGGCCGCTGGCTGCTCGATTTGATAAAC
ATCCTGCAGAGCATAGTGGTGCAGGAGCGCAGCTTGAGCCTGGCTGACAAGGTG
GCCGCCATCAACTATTCCATGCTTAGCCTGGGCAAGTTTTACGCCCGCAAGATAT
```

-continued

```
ACCATACCCCTTACGTTCCCATAGACAAGGAGGTAAAGATCGAGGGGTTCTACAT
GCGCATGGCGCTGAAGGTGCTTACCTTGAGCGACGACCTGGGCGTTTATCGCAAC
GAGCGCATCCACAAGGCCGTGAGCGTGAGCCGGCGGCGCGAGCTCAGCGACCGC
GAGCTGATGCACAGCCTGCAAAGGGCCCTGGCTGGCACGGGCAGCGGCGATAGA
GAGGCCGAGTCCTACTTTGACGCGGGCGCTGACCTGCGCTGGGCCCCAAGCCGA
CGCGCCCTGGAGGCAGCTGGGGCCGGACCTGGGCTGGCGGTGGCACCCGCGCGC
GCTGGCAACGTCGGCGGCGTGGAGGAATATGACGAGGACGATGAGTACGAGCCA
GAGGACGGCGAGTACTAAGCGGTGATGTTTCTGATCAGATGATGCAAGACGCAA
CGGACCCGGCGGTGCGGGCGGCGCTGCAGAGCCAGCCGTCCGGCCTTAACTCCA
CGGACGACTGGCGCCAGGTCATGGACCGCATCATGTCGCTGACTGCGCGCAATC
CTGACGCGTTCCGGCAGCAGCCGCAGGCCAACCGGCTCTCCGCAATTCTGGAAG
CGGTGGTCCCGGCGCGCGCAAACCCCACGCACGAGAAGGTGCTGGCGATCGTAA
ACGCGCTGGCCGAAAACAGGGCCATCCGGCCCGACGAGGCCGGCCTGGTCTACG
ACGCGCTGCTTCAGCGCGTGGCTCGTTACAACAGCGGCAACGTGCAGACCAACC
TGGACCGGCTGGTGGGGGATGTGCGCGAGGCCGTGGCGCAGCGTGAGCGCGCGC
AGCAGCAGGGCAACCTGGGCTCCATGGTTGCACTAAACGCCTTCCTGAGTACAC
AGCCCGCCAACGTGCCGCGGGGACAGGAGGACTACACCAACTTTGTGAGCGCAC
TGCGGCTAATGGTGACTGAGACACCGCAAAGTGAGGTGTACCAGTCTGGGCCAG
ACTATTTTTCCAGACCAGTAGACAAGGCCTGCAGACCGTAAACCTGAGCCAGGC
TTTCAAAAACTTGCAGGGGCTGTGGGGGGTGCGGGCTCCCACAGGCGACCGCGC
GACCGTGTCTAGCTTGCTGACGCCCAACTCGCGCCTGTTGCTGCTGCTAATAGCG
CCCTTCACGGACAGTGGCAGCGTGTCCCGGGACACATACCTAGGTCACTTGCTGA
CACTGTACCGCGAGGCCATAGGTCAGGCGCATGTGGACGAGCATACTTTCCAGG
AGATTACAAGTGTCAGCCGCGCGCTGGGGCAGGAGGACACGGGCAGCCTGGAGG
CAACCCTAAACTACCTGCTGACCAACCGGCGGCAGAAGATCCCCTCGTTGCACA
GTTTCGCACCCTTTGGCGCATCCCATTCTCCAGTAACTTTATGTCCATGGGCGCAC
TCACAGACCTGGGCCAAAACCTTCTCTACGCCAACTCCGCCCACGCGCTAGACAT
GACTTTTGAGGTGGATCCCATGGACGAGCCCACCCTTCTTTATGTTTTGTTTGAAG
TCTTTGACGTGGTCCGTGTGCACCGGCCGCACCGCGGCGTCATCGAAACCGTGTA
CCTGCGCACGCCCTTCTCGGCCGGCAACGCCACAACATAAAGAAGCAAGCAACA
TCAACAACAGCTGCCGCCATGGGCTCCAGTGAGCAGGAACTGAAAGCCATTGTC
AAAGATCTTGGTTGTGGGCCATATTTTTTGGGCACCTATGACAAGCGCTTTCCAG
GCTTTGTTTCTCCACACAAGCTCGCCTGCGCCATAGTCAATACGGCCGGTCGCGA
GACTGGGGGCGTACACTGGATGGCCTTTGCCTGGAACCCGCACTCAAAAACATG
CTACCTCTTTGAGCCCTTTGGCTTTTCTGACCAGCGACTCAAGCAGGTTTACCAGT
TTGAGTACGAGTCACTCCTGCGCCGTAGCGCCATTGCTTCTTCCCCCGACCGCTGT
ATAACGCTGGAAAAGTCCACCCAAAGCGTACAGGGGCCCAACTCGGCCGCCTGT
GGACTATTCTGCTGCATGTTTCTCCACGCCTTTGCCAACTGGCCCCAAACTCCCAT
GGATCACAACCCCACCATGAACCTTATTACCGGGGTACCCAACTCCATGCTCAAC
AGTCCCCAGGTACAGCCCACCCTGCGTCGCAACCAGGAACAGCTCTACAGCTTCC
TGGAGCGCCACTCGCCCTACTTCCGCAGCCACAGTGCGCAGATTAGGAGCGCCA
```

-continued

```
CTTCTTTTTGTCACTTGAAAAACATGTAAAAATAATGTACTAGAGACACTTTCAA
TAAAGGCAAATGCTTTTATTTGTACACTCTCGGGTGATTATTTACCCCCACCCTTG
CCGTCTGCGCCGTTTAAAAATCAAAGGGGTTCTGCCGCGCATCGCTATGCGCCAC
TGGCAGGGACACGTTGCGATACTGGTGTTTAGTGCTCCACTTAAACTCAGGCACA
ACCATCCGCGGCAGCTCGGTGAAGTTTTCACTCCACAGGCTGCGCACCATCACCA
ACGCGTTTAGCAGGTCGGGCGCCGATATCTTGAAGTCGCAGTTGGGGCCTCCGCC
CTGCGCGCGCGAGTTGCGATACACAGGGTTGCAGCACTGGAACACTATCAGCGC
CGGGTGGTGCACGCTGGCCAGCACGCTCTTGTCGGAGATCAGATCCGCGTCCAG
GTCCTCCGCGTTGCTCAGGGCGAACGGAGTCAACTTTGGTAGCTGCCTTCCCAAA
AAGGGCGCGTGCCCAGGCTTTGAGTTGCACTCGCACCGTAGTGGCATCAAAAGG
TGACCGTGCCCGGTCTGGGCGTTAGGATACAGCGCCTGCATAAAAGCCTTGATCT
GCTTAAAAGCCACCTGAGCCTTTGCGCCTTCAGAGAAGAACATGCCGCAAGACTT
GCCGGAAAACTGATTGGCCGGACAGGCCGCGTCGTGCACGCAGCACCTTGCGTC
GGTGTTGGAGATCTGCACCACATTTCGGCCCCACCGGTTCTTCACGATCTTGGCC
TTGCTAGACTGCTCCTTCAGCGCGCGCTGCCCGTTTTCGCTCGTACATCCATTTC
AATCACGTGCTCCTTATTTATCATAATGCTTCCGTGTAGACACTTAAGCTCGCCTT
CGATCTCAGCGCAGCGGTGCAGCCACAACGCGCAGCCCGTGGGCTCGTGATGCT
TGTAGGTCACCTCTGCAAACGACTGCAGGTACGCCTGCAGGAATCGCCCCATCAT
CGTCACAAAGGTCTTGTTGCTGGTGAAGGTCAGCTGCAACCCGCGGTGCTCCTCG
TTCAGCCAGGTCTTGCATACGGCCGCCAGAGCTTCCACTTGGTCAGGCAGTAGTT
TGAAGTTCGCCTTTAGATCGTTATCCACGTGGTACTTGTCCATCAGCGCGCGCGC
AGCCTCCATGCCCTTCTCCCACGCAGACACGATCGGCACACTCAGCGGGTTCATC
ACCGTAATTTCACTTTCCGCTTCGCTGGGCTCTTCCTCTTCCTCTTGCGTCCGCAT
ACCACGCGCCACTGGGTCGTCTTCATTCAGCCGCCGCACTGTGCGCTTACCTCCTT
TGCCATGCTTGATTAGCACCGGTGGGTTGCTGAAACCCACCATTTGTAGCGCCAC
ATCTTCTCTTTCTTCCTCGCTGTCCACGATTACCTCTGGTGATGGCGGGCGCTCGG
GCTTGGGAGAAGGGCGCTTCTTTTTCTTCTTGGGCGCAATGGCCAAATCCGCCGC
CGAGGTCGATGGCCGCGGGCTGGGTGTGCGCGGCACCAGCGCGTCTTGTGATGA
GTCTTCCTCGTCCTCGGACTCGATACGCCGCCTCATCCGCTTTTTTGGGGCGCCC
GGGGAGGCGGCGGCGACGGGGACGGGGACGACACGTCCTCCATGGTTGGGGA
CGTCGCGCCGCACCGCGTCCGCGCTCGGGGGTGGTTTCGCGCTGCTCCTCTTCCC
GACTGGCCATTTCCTTCTCCTATAGGCAGAAAAAGATCATGGAGTCAGTCGAGAA
GAAGGACAGCCTAACCGCCCCCTCTGAGTTCGCCACCACCGCCTCCACCGATGCC
GCCAACGCGCCTACCACCTTCCCCGTCGAGGCACCCCCGCTTGAGGAGGAGGAA
GTGATTATCGAGCAGGACCCAGGTTTTGTAAGCGAAGACGACGAGGACCGCTCA
GTACCAACAGAGGATAAAAAGCAAGACCAGGACAACGCAGAGGCAAACGAGGA
ACAAGTCGGGCGGGGGACGAAAGGCATGGCGACTACCTAGATGTGGGAGACG
ACGTGCTGTTGAAGCATCTGCAGCGCCAGTGCGCCATTATCTGCGACGCGTTGCA
AGAGCGCAGCGATGTGCCCCTCGCCATAGCGGATGTCAGCCTTGCCTACGAACG
CCACCTATTCTCACCGCGCGTACCCCCCAAACGCCAAGAAAACGGCACATGCGA
GCCCAACCCGCGCCTCAACTTCTACCCCGTATTTGCCGTGCCAGAGGTGCTTGCC
```

-continued

```
ACCTATCACATCTTTTTCCAAAACTGCAAGATACCCCTATCCTGCCGTGCCAACC

GCAGCCGAGCGGACAAGCAGCTGGCCTTGCGGCAGGGCGCTGTCATACCTGATA

TCGCCTCGCTCAACGAAGTGCCAAAAATCTTTGAGGGTCTTGGACGCGACGAGA

AGCGCGCGGCAAACGCTCTGCAACAGGAAAACAGCGAAAATGAAAGTCACTCTG

GAGTGTTGGTGGAACTCGAGGGTGACAACGCGCGCCTAGCCGTACTAAAACGCA

GCATCGAGGTCACCCACTTTGCCTACCCGGCACTTAACCTACCCCCCAAGGTCAT

GAGCACAGTCATGAGTGAGCTGATCGTGCGCCGTGCGCAGCCCCTGGAGAGGGA

TGCAAATTTGCAAGAACAAACAGAGGAGGGCCTACCCGCAGTTGGCGACGAGCA

GCTAGCGCGCTGGCTTCAAACGCGCGAGCCTGCCGACTTGGAGGAGCGACGCAA

ACTAATGATGGCCGCAGTGCTCGTTACCGTGGAGCTTGAGTGCATGCAGCGGTTC

TTTGCTGACCCGGAGATGCAGCGCAAGCTAGAGGAAACATTGCACTACACCTTTC

GACAGGGCTACGTACGCCAGGCCTGCAAGATCTCCAACGTGGAGCTCTGCAACC

TGGTCTCCTACCTTGGAATTTTGCACGAAAACCGCCTTGGGCAAAACGTGCTTCA

TTCCACGCTCAAGGGCGAGGCGCGCCGCGACTACGTCCGCGACTGCGTTTACTTA

TTTCTATGCTACACCTGGCAGACGGCCATGGGCGTTTGGCAGCAGTGCTTGGAGG

AGTGCAACCTCAAGGAGCTGCAGAAACTGCTAAAGCAAAACTTGAAGGACCTAT

GGACGGCCTTCAACGAGCGCTCCGTGGCCGCGCACCTGGCGGACATCATTTTCCC

CGAACGCCTGCTTAAAACCCTGCAACAGGGTCTGCCAGACTTCACCAGTCAAAG

CATGTTGCAGAACTTTAGGAACTTTATCCTAGAGCGCTCAGGAATCTTGCCCGCC

ACCTGCTGTGCACTTCCTAGCGACTTTGTGCCCATTAAGTACCGCGAATGCCCTC

CGCCGCTTTGGGGCCACTGCTACCTTCTGCAGCTAGCCAACTACCTTGCCTACCA

CTCTGACATAATGGAAGACGTGAGCGGTGACGGTCTACTGGAGTGTCACTGTCGC

TGCAACCTATGCACCCCGCACCGCTCCCTGGTTTGCAATTCGCAGCTGCTTAACG

AAAGTCAAATTATCGGTACCTTTGAGCTGCAGGGTCCCTCGCCTGACGAAAAGTC

CGCGGCTCCGGGGTTGAAACTCACTCCGGGGCTGTGGACGTCGGCTTACCTTCGC

AAATTTGTACCTGAGGACTACCACGCCCACGAGATTAGGTTCTACGAAGACCAAT

CCCGCCCGCCAAATGCGGAGCTTACCGCCTGCGTCATTACCCAGGGCCACATTCT

TGGCCAATTGCAAGCCATCAACAAAGCCCGCCAAGAGTTTCTGCTACGAAAGGG

ACGGGGGTTTACTTGGACCCCCAGTCCGGCGAGGAGCTCAACCCAATCCCCCC

GCCGCCGCAGCCCTATCAGCAGCAGCCGCGGGCCCTTGCTTCCCAGGATGGCACC

CAAAAGAAGCTGCAGCTGCCGCCGCCACCCACGGACGAGGAGGAATACTGGG

ACAGTCAGGCAGAGGAGGTTTTGGACGAGGAGGAGGAGGACATGATGGAAGAC

TGGGAGAGCCTAGACGAGGAAGCTTCCGAGGTCGAAGAGGTGTCAGACGAAAC

ACCGTCACCCTCGGTCGCATTCCCCTCGCCGGCGCCCCAGAAATCGGCAACCGGT

TCCAGCATGGCTACAACCTCCGCTCCTCAGGCGCCGCCGGCACTGCCCGTTCGCC

GACCCAACCGTAGATGGGACACCACTGGAACCAGGGCCGGTAAGTCCAAGCAGC

CGCCGCCGTTAGCCCAAGAGCAACAACAGCGCCAAGGCTACCGCTCATGGCGCG

GGCACAAGAACGCCATAGTTGCTTGCTTGCAAGACTGTGGGGGCAACATCTCCTT

CGCCCGCCGCTTTCTTCTCTACCATCACGGCGTGGCCTTCCCCCGTAACATCCTGC

ATTACTACCGTCATCTCTACAGCCCATACTGCACCGGCGGCAGCGGCAGCGGCAG

CAACAGCAGCGGCCACACAGAAGCAAAGGCGACCGGATAGCAAGACTCTGACA
```

-continued

```
AAGCCCAAGAAATCCACAGCGGCGGCAGCAGCAGGAGGAGGAGCGCTGCGTCT

GGCGCCCAACGAACCCGTATCGACCCGCGAGCTTAGAAACAGGATTTTTCCCACT

CTGTATGCTATATTTCAACAGAGCAGGGGCCAAGAACAAGAGCTGAAAATAAAA

AACAGGTCTCTGCGATCCCTCACCCGCAGCTGCCTGTATCACAAAAGCGAAGATC

AGCTTCGGCGCACGCTGGAAGACGCGGAGGCTCTCTTCAGTAAATACTGCGCGCT

GACTCTTAAGGACTAGTTTCGCGCCCTTTCTCAAATTTAAGCGCGAAAACTACGT

CATCTCCAGCGGCCACACCCGGCGCCAGCACCTGTCGTCAGCGCCATTATGAGCA

AGGAAATTCCCACGCCCTACATGTGGAGTTACCAGCCACAAATGGGACTTGCGG

CTGGAGCTGCCCAAGACTACTCAACCCGAATAAACTACATGAGCGCGGGACCCC

ACATGATATCCCGGGTCAACGGAATCCGCGCCCACCGAAACCGAATTCTCTTGGA

ACAGGCGGCTATTACCACCACACCTCGTAATAACCTTAATCCCCGTAGTTGGCCC

GCTGCCCTGGTGTACCAGGAAAGTCCCGCTCCCACCACTGTGGTACTTCCCAGAG

ACGCCCAGGCCGAAGTTCAGATGACTAACTCAGGGGCGCAGCTTGCGGGCGGCT

TTCGTCACAGGGTGCGGTCGCCCGGGCAGGGTATAACTCACCTGACAATCAGAG

GGCGAGGTATTCAGCTCAACGACGAGTCGGTGAGCTCCTCGCTTGGTCTCCGTCC

GGACGGGACATTTCAGATCGGCGGCGCCGGCCGTCCTTCATTCACGCCTCGTCAG

GCAATCCTAACTCTGCAGACCTCGTCCTCTGAGCCGCGCTCTGGAGGCATTGGAA

CTCTGCAATTTATTGAGGAGTTTGTGCCATCGGTCTACTTTAACCCCTTCTCGGGA

CCTCCCGGCCACTATCCGGATCAATTTATTCCTAACTTTGACGCGGTAAAGGACT

CGGCGGACGGCTACGACTGAATGTTAAGTGGAGAGGCAGAGCAACTGCGCCTGA

AACACCTGGTCCACTGTCGCCGCCACAAGTGCTTTGCCCGCGACTCCGGTGAGTT

TTGCTACTTTGAATTGCCCGAGGATCATATCGAGGGCCCGGCGCACGGCGTCCGG

CTTACCGCCCAGGGAGAGCTTGCCCGTAGCCTGATTCGGGAGTTTACCCAGCGCC

CCCTGCTAGTTGAGCGGGACAGGGGACCCTGTGTTCTCACTGTGATTTGCAACTG

TCCTAACCTTGGATTACATCAAGATCCTCTAGTTAATTAACTAGAGTACCCGGGG

ATCTTATTCCCTTTAACTAATAAAAAAAAATAATAAAGCATCACTTACTTAAAAT

CAGTTAGCAAATTTCTGTCCAGTTTATTCAGCAGCACCTCCTTGCCCTCCTCCCAG

CTCTGGTATTGCAGCTTCCTCCTGGCTGCAAACTTTCTCCACAATCTAAATGGAAT

GTCAGTTTCCTCCTGTTCCTGTCCATCCGCACCCACTATCTTCATGTTGTTGCAGA

TGAAGCGCGCAAGACCGTCTGAAGATACCTTCAACCCCGTGTATCCATATGACAC

GGAAACCGGTCCTCCAACTGTGCCTTTTCTTACTCCTCCCTTTGTATCCCCCAATG

GGTTTCAAGAGAGTCCCCCTGGGGTACTCTCTTTGCGCCTATCCGAACCTCTAGTT

ACCTCCAATGGCATGCTTGCGCTCAAAATGGGCAACGGCCTCTCTCTGGACGAGG

CCGGCAACCTTACCTCCCAAAATGTAACCACTGTGAGCCCACCTCTCAAAAAAAC

CAAGTCAAACATAAACCTGGAAATATCTGCACCCCTCACAGTTACCTCAGAAGCC

CTAACTGTGGCTGCCGCCGCACCTCTAATGGTCGCGGGCAACACACTCACCATGC

AATCACAGGCCCCGCTAACCGTGCACGACTCCAAACTTAGCATTGCCACCCAAG

GACCCCTCACAGTGTCAGAAGGAAAGCTAGCCCTGCAAACATCAGGCCCCCTCA

CCACCACCGATAGCAGTACCCTTACTATCACTGCCTCACCCCCTCTAACTACTGC

CACTGGTAGCTTGGGCATTGACTTGAAAGAGCCCATTTATACACAAAATGGAAA

ACTAGGACTAAAGTACGGGGCTCCTTTGCATGTAACAGACGACCTAAACACTTTG
```

-continued

```
ACCGTAGCAACTGGTCCAGGTGTGACTATTAATAATACTTCCTTGCAAACTAAAG
TTACTGGAGCCTTGGGTTTTGATTCACAAGGCAATATGCAACTTAATGTAGCAGG
AGGACTAAGGATTGATTCTCAAAACAGACGCCTTATACTTGATGTTAGTTATCCG
TTTGATGCTCAAAACCAACTAAATCTAAGACTAGGACAGGGCCCTCTTTTTATAA
ACTCAGCCCACAACTTGGATATTAACTACAACAAAGGCCTTTACTTGTTTACAGC
TTCAAACAATTCCAAAAAGCTTGAGGTTAACCTAAGCACTGCCAAGGGGTTGAT
GTTTGACGCTACAGCCATAGCCATTAATGCAGGAGATGGGCTTGAATTTGGTTCA
CCTAATGCACCAAACACAAATCCCCTCAAAACAAAAATTGGCCATGGCCTAGAA
TTTGATTCAAACAAGGCTATGGTTCCTAAACTAGGAACTGGCCTTAGTTTTGACA
GCACAGGTGCCATTACAGTAGGAAACAAAAATAATGATAAGCTAACTTTGTGGA
CCACACCAGCTCCATCTCCTAACTGTAGACTAAATGCAGAGAAAGATGCTAAACT
CACTTTGGTCTTAACAAAATGTGGCAGTCAAATACTTGCTACAGTTTCAGTTTTG
GCTGTTAAAGGCAGTTTGGCTCCAATATCTGGAACAGTTCAAAGTGCTCATCTTA
TTATAAGATTTGACGAAAATGGAGTGCTACTAAACAATTCCTTCCTGGACCCAGA
ATATTGGAACTTTAGAAATGGAGATCTTACTGAAGGCACAGCCTATACAAACGCT
GTTGGATTTATGCCTAACCTATCAGCTTATCCAAAATCTCACGGTAAAACTGCCA
AAAGTAACATTGTCAGTCAAGTTTACTTAAACGGAGACAAAACTAAACCTGTAA
CACTAACCATTACACTAAACGGTACACAGGAAACAGGAGACACAACTCCAAGTG
CATACTCTATGTCATTTTCATGGGACTGGTCTGGCCACAACTACATTAATGAAAT
ATTTGCCACATCCTCTTACACTTTTTCATACATTGCCCAAGAATAAAGAATCGTTT
GTGTTATGTTTCAACGTGTTTATTTTTCAATTGCAGAAAATTTCAAGTCATTTTTC
ATTCAGTAGTATAGCCCCACCACCACATAGCTTATACAGATCACCGTACCTTAAT
CAAACTCACAGAACCCTAGTATTCAACCTGCCACCTCCCTCCCAACACACAGAGT
ACACAGTCCTTTCTCCCCGGCTGGCCTTAAAAAGCATCATATCATGGGTAACAGA
CATATTCTTAGGTGTTATATTCCACACGGTTTCCTGTCGAGCCAAACGCTCATCAG
TGATATTAATAAACTCCCCGGGCAGCTCACTTAAGTTCATGTCGCTGTCCAGCTG
CTGAGCCACAGGCTGCTGTCCAACTTGCGGTTGCTTAACGGGCGGCGAAGGAGA
AGTCCACGCCTACATGGGGGTAGAGTCATAATCGTGCATCAGGATAGGGCGGTG
GTGCTGCAGCAGCGCGCGAATAAACTGCTGCCGCCGCCGCTCCGTCCTGCAGGA
ATACAACATGGCAGTGGTCTCCTCAGCGATGATTCGCACCGCCCGCAGCATAAG
GCGCCTTGTCCTCCGGGCACAGCAGCGCACCCTGATCTCACTTAAATCAGCACAG
TAACTGCAGCACAGCACCACAATATTGTTCAAAATCCCACAGTGCAAGGCGCTGT
ATCCAAAGCTCATGGCGGGGACCACAGAACCCACGTGGCCATCATACCACAAGC
GCAGGTAGATTAAGTGGCGACCCCTCATAAACACGCTGGACATAAACATTACCT
CTTTTGGCATGTTGTAATTCACCACCTCCCGGTACCATATAAACCTCTGATTAAAC
ATGGCGCCATCCACCACCATCCTAAACCAGCTGGCCAAAACCTGCCCGCCGGCTA
TACACTGCAGGGAACCGGGACTGGAACAATGACAGTGGAGAGCCCAGGACTCGT
AACCATGGATCATCATGCTCGTCATGATATCAATGTTGGCACAACACAGGCACAC
GTGCATACACTTCCTCAGGATTACAAGCTCCTCCCGCGTTAGAACCATATCCCAG
GGAACAACCCATTCCTGAATCAGCGTAAATCCACACTGCAGGGAAGACCTCGC
ACGTAACTCACGTTGTGCATTGTCAAAGTGTTACATTCGGGCAGCAGCGGATGAT
```

-continued

```
CCTCCAGTATGGTAGCGCGGGTTTCTGTCTCAAAAGGAGGTAGACGATCCCTACT
GTACGGAGTGCGCCGAGACAACCGAGATCGTGTTGGTCGTAGTGTCATGCCAAA
TGGAACGCCGGACGTAGTCATATTTCCTGAAGCAAAACCAGGTGCGGGCGTGAC
AAACAGATCTGCGTCTCCGGTCTCGCCGCTTAGATCGCTCTGTGTAGTAGTTGTA
GTATATCCACTCTCTCAAAGCATCCAGGCGCCCCTGGCTTCGGGTTCTATGTAA
ACTCCTTCATGCGCCGCTGCCCTGATAACATCCACCACCGCAGAATAAGCCACAC
CCAGCCAACCTACACATTCGTTCTGCGAGTCACACACGGGAGGAGCGGGAAGAG
CTGGAAGAACCATGTTTTTTTTTTATTCCAAAAGATTATCCAAAACCTCAAAAT
GAAGATCTATTAAGTGAACGCGCTCCCCTCCGGTGGCGTGGTCAAACTCTACAGC
CAAAGAACAGATAATGGCATTTGTAAGATGTTGCACAATGGCTTCCAAAAGGCA
AACGGCCCTCACGTCCAAGTGGACGTAAAGGCTAAACCCTTCAGGGTGAATCTC
CTCTATAAACATTCCAGCACCTTCAACCATGCCCAAATAATTCTCATCTCGCCAC
CTTCTCAATATATCTCTAAGCAAATCCCGAATATTAAGTCCGGCCATTGTAAAAA
TCTGCTCCAGAGCGCCCTCCACCTTCAGCCTCAAGCAGCGAATCATGATTGCAAA
AATTCAGGTTCCTCACAGACCTGTATAAGATTCAAAAGCGGAACATTAACAAAA
ATACCGCGATCCCGTAGGTCCCTTCGCAGGGCCAGCTGAACATAATCGTGCAGGT
CTGCACGGACCAGCGCGGCCACTTCCCCGCCAGGAACCTTGACAAAAGAACCCA
CACTGATTATGACACGCATACTCGGAGCTATGCTAACCAGCGTAGCCCCGATGTA
AGCTTTGTTGCATGGGCGGCGATATAAAATGCAAGGTGCTGCTCAAAAAATCAG
GCAAAGCCTCGCGCAAAAAAGAAAGCACATCGTAGTCATGCTCATGCAGATAAA
GGCAGGTAAGCTCCGGAACCACCACAGAAAAAGACACCATTTTTCTCTCAAACA
TGTCTGCGGGTTTCTGCATAAACACAAAATAAAATAACAAAAAAACATTTAAAC
ATTAGAAGCCTGTCTTACAACAGGAAAAACAACCCTTATAAGCATAAGACGGAC
TACGGCCATGCCGGCGTGACCGTAAAAAAACTGGTCACCGTGATTAAAAAGCAC
CACCGACAGCTCCTCGGTCATGTCCGGAGTCATAATGTAAGACTCGGTAAACACA
TCAGGTTGATTCATCGGTCAGTGCTAAAAAGCGACCGAAATAGCCCGGGGGAAT
ACATACCCGCAGGCGTAGAGACAACATTACAGCCCCCATAGGAGGTATAACAAA
ATTAATAGGAGAGAAAAACACATAAACACCTGAAAAACCCTCCTGCCTAGGCAA
AATAGCACCCTCCCGCTCCAGAACAACATACAGCGCTTCACAGCGGCAGCCTAA
CAGTCAGCCTTACCAGTAAAAAAGAAAACCTATTAAAAAAACACCACTCGACAC
GGCACCAGCTCAATCAGTCACAGTGTAAAAAAGGGCCAAGTGCAGAGCGAGTAT
ATATAGGACTAAAAAATGACGTAACGGTTAAAGTCCACAAAAAACACCCAGAAA
ACCGCACGCGAACCTACGCCCAGAAACGAAAGCCAAAAAACCCACAACTTCCTC
AAATCGTCACTTCCGTTTTCCCACGTTACGTAACTTCCCATTTTAAGAAAACTACA
ATTCCCAACACATACAAGTTACTCCGCCCTAAAACCTACGTCACCCGCCCCGTTC
CCACGCCCCGCGCCACGTCACAAACTCCACCCCCTCATTATCATATTGGCTTCAA
TCCAAAATAAGGTATATTATTGATGATTTATTTTGGATTGAAGCCAATATGATAA
TGAGGGGGTGGAGTTTGTGACGTGGCGCGGGCGTGGGAACGGGGCGGGTGACG
TAGTAGTGTGGCGGAAGTGTGATGTTGCAAGTGTGGCGGAACACATGTAAGCGA
CGGATGTGGCAAAAGTGACGTTTTTGGTGTGCGCCGGATCCACAGGACGGGTGT
GGTCGCCATGATCGCGTAGTCGATAGTGGCTCCAAGTAGCGAAGCGAGCAGGAC
```

```
-continued
TGGGCGGCGGCCAAAGCGGTCGGACAGTGCTCCGAGAACGGGTGCGCATAGAAA

TTGCATCAACGCATATAGCGCTAGCAGCACGCCATAGTGACTGGCGATGCTGTCG

GAATGGACGATATCCCGCAAGAGGCCCGGCAGTACCGGCATAACCAAGCCTATG

CCTACAGCATCCAGGGTGACGGTGCCGAGGATGACGATGAGCGCATTGTTAGAT

TTCATACACGGTGCCTGACTGCGTTAGCAATTTAACTGTGATAAACTACCGCATT

AAAGCTTATCGAATTCGTAATCATGGTCATAGCTGTTTCCTGTGTGAAATTGTTAT

CCGCTCACAATTCCACACAACATACGAGCCGGAAGCATAAAGTGTAAAGCCTGG

GGTGCCTAATGAGTGAGCTAACTCACATTAATTGCGTTGCGCTCACTGCCCGCTT

TCCAGTCGGGAAACCTGTCGTGCCAGCTGCATTAATGAATCGGCCAACGCGCGG

GGAGAGGCGGTTTGCGTATTGGGCGC
```

For co-packaging experiments, ratios of the two expression constructs were varied between 1:9, 1:1 and 9:1 ratios and determined off of the total amount of expression plasmid DNA necessary and the total base pair size of the individual constructs to retain equimolar ratio with the helpers; at the surface area of 148 cm², the final amounts of plasmids were 16 µg of expression plasmids, 16 µg of rep2/cap9, and 38 µg of pXX6-80. Cells were incubated at 37° C. at 5% CO2 for 60 hours, washed in PBS, harvested in PBS-5 mM EDTA and centrifuged at 1000 g for 10 minutes at 4° C. Cells were resuspended in lysis buffer (150 mM NaCl, 50 mM Tris, pH 8.4) and subjected to three freeze/thaw cycles between a −80° C. freezer and 37° C. water bath. Benzonase (50 U/mL) and MgCl2 were added to the cell lysate and incubated for 30 minutes at 37° C. The crude lysate was clarified by centrifugation at 3400 g for 20 minutes at 4° C. The vector-containing supernatant was used for quantitative PCR (qPCR) or further purified by iodixanol step gradients (Zolotukhin et al., 2002). Final formulations of iodixanol purified vectors were concentrated in PBS (Apollo® Concentrators, Orbital Biosciences, Topsfield, Mass.). Each ratio of co-packaged vectors was performed independently in triplicate.

Titration of AAV Vectors

DNA from all AAV vectors, both from crude lysate or iodixanol purified preparations, was extracted using Qiagen reagents. 100 µL of vector from clarified lysate or 10 µL of iodixanol purified vector were treated with proteinase K (Qiagen; 0.2 mg/ml, 55° C., 30 min) followed by DNA extraction following manufacturer's instructions.

For AAV9-GFP and AAV9-mCherry, primers designed for the cytomegalovirus enhancer were used to determine total titer (primer set 1; see Table 2 for primer sequences). Additional forward and reverse primers designed uniquely to the GFP and mCherry transgenes (primer sets 2 and 3, respectively) were also used to determine the individual contribution of each construct to the total vector preparation. Endpoint PCR was optimized by amplifying 0.5 ng of extracted DNA on a 3-step cycling protocol across a temperature gradient (30 cycles: 94° C. for 15 sec, 46-50° C. for 15 sec, 72° C. for 30 sec) preceded by a 2 minute 94° C. incubation and followed by a 1 minute 72° C. elongation. QPCR titration was optimized by amplifying 1 ng of extracted DNA on a 2-step cycling protocol across a temperature gradient (50 cycles: 95° C. for 10 sec, 57-63° C. for 1 min) preceded by a 10 min 95° C. incubation and followed with a melt curve protocol (95° C. for 1 min, 63° C. for 1 min, 65-95° C. for 5 sec in 0.5° C. increments). An annealing temperature of 50° C. was used for all primer sets and combinations for endpoint PCR experiments. For qPCR, CMV targeted primers were annealed at 63° C., GFP and mCherry primers were annealed at 50° C. The primers below are SEQ ID NOs: 9-17 from top to bottom.

TABLE 2

Primer Sequences for PCR (SEQ ID NO: 9)
(SEQ ID NO: 10)
(SEQ ID NO: 11)
(SEQ ID NO: 12)
(SEQ ID NO: 13)
(SEQ ID NO: 14)
(SEQ ID NO: 15)
(SEQ ID NO: 16)
(SEQ ID NO: 17)

TABLE 1

Primer Sequences for PCR

| Set | Primer | Sequence |
|---|---|---|
| 1 | CB2-F | 5'-TCCCATAGTAACGCCAATAGG-3' |
|   | CB2-R | 5'-CTTGGCATATGATACACTTGATG-3' |
| 2 | GFP-F | 5'-ATGGAAACATTCTCGGCCACAAGC-3' |
|   | GFP-R | 5'-TCGCCGATTGGAGTGTTCTGTTG-3' |
| 3 | mCherry-F | 5'-GGACGGCGAGTTCATCTACA-3' |
|   | mCherry-R | 5'-TTGACCTCAGCGTCGTAGTG-3' |
| 4 | DES-F | 5'-GGCTGATGTCAGGAGGGATA-3' |
|   | LSP-F | 5'-GGGACAGTGAATCCGGAAAG-3' |
|   | coGAA-R | 5'-AAGTCGTGCAGCAGGATATG-3' |

CB, CMV enhancer/chicken β-actin promoter
DES, desmin promoter,
LSP, liver specific promoter
coGAA, human codon optimized acid alpha-glucosidase To titrate co-packaged AAV9-LSP-coGAA and AAV9-DES-coGAA, forward primers unique to the promoter sequences were used in conjunction with a reverse primer anchored within the transgene shared by both constructs (primer set 4). Endpoint and qPCR performed on co-packaged AAV9-LSP-coGAA and AAV9-DES-coGAA was optimized and performed identically as with co-packaged AAV9-GFP and AAV9-mCherry. For qPCR, LSP, DES and coGAA primers were annealed at 60° C.

Standard curves were generated by using 109-105 total copies, as well as the inclusion of a non-template control, of the relevant expression plasmids either singly or in combination with the additional co-packaged construct. For each endpoint or qPCR reaction of single or combined expression plasmids, the corresponding primers were also used individually or in combination. For example, 4 standard curves of pTRUF11 were amplified individually with primers targeting the CMV enhancer (primer set 1), GFP (primer set 2), mCherry (primer set 3), or a combination of GFP and mCherry (primer sets 2 and 3). Likewise, 4 standard curves of combined pTRUF11 and pTRUF11-mCherry were amplified individually with primers targeting the CMV enhancer (primer set 1), GFP (primer set 2), mCherry (primer set 3), or a combination of GFP and mCherry (primer sets 2 and 3). Each combination of primer sets and plasmids was investigated to ensure the specificity of amplification.

Endpoint PCR was conducted using ILLUSTRA™ PURETAQ™ READY-TO-GO™ PCR beads (GE Healthcare, Buckinghamshire, UK). 0.5 ng of DNA was amplified from each preparation and ran on a 2% agarose gel at 100 V for 90 minutes for GFP and mCherry vectors or on a 1.5% agarose gel at 110 V for 50 minutes for LSP and DES vectors. QPCR was performed with ITAQ™ Universal SYBR® Green Supermix using 1 ng of DNA on a BIO-RAD™ CFX96™ Real-Time PCR Detection System and analyzed using BIO-RAD™ CFX MANAGER™ v. 3.1 software (Bio-Rad Laboratories, Inc., Hercules, Calif.). A multiplication factor of two was included when determining vector genomes per milliliter (vg/mL) to account for the packaging of positive- and negative-sense viral genomes.

Single Cell Fluorescence Assay

The infectious titer of AAV9-GFP and AAV9-mCherry was determined essentially as described previously (Zolotukhin et al., 2002). C12 cells were seeded at $2\times10^4$ cells in a 96-well plate and infected 18 hours later with the co-packaged vectors in a serial 10-fold dilution series. Due to the low in vitro transduction efficiency of AAV9, co-infection with Ad5 (MOI of 20) was implemented. 40 hours later, red and green cells were counted using a fluorescent microscope and the infectious titer was calculated based on dilution. Each ratio, packaged in triplicate, was assayed in duplicate. The particle-to-infectivity ratio was then determined by the qPCR titer divided by the infectious titer.

Statistical Analysis

Figures and statistical analysis was performed using GraphPad Prism v. 5.0 (GraphPad Software, La Jolla, Calif.).

Results

AAV Packages Expression Plasmids in a Defined Stoichiometry

To facilitate the use and production of multiple vectors, a novel co-packaging method was investigated that would allow for the generation of a heterogeneous population of AAV vectors in a single manufacturing step. It was hypothesized that combining plasmids to be packaged at a known input ratio would result in an output vector preparation containing the equivalent ratio. To demonstrate this hypothesis, two vectors that only differed by the reporter gene, GFP or mCherry, were co-packaged into AAV serotype 9 (AAV9). The vectors were co-packaged at 1:9, 1:1 and 9:1 molar ratios, respectively. Vector DNA extracted either from crude lysates or from purified vectors were first analyzed by endpoint PCR (FIG. 1). Semi-quantitative end-point PCR revealed that each vector preparation differentially packaged each transgene, recapitulating the ratios that were transfected into the cells.

Figure 2:
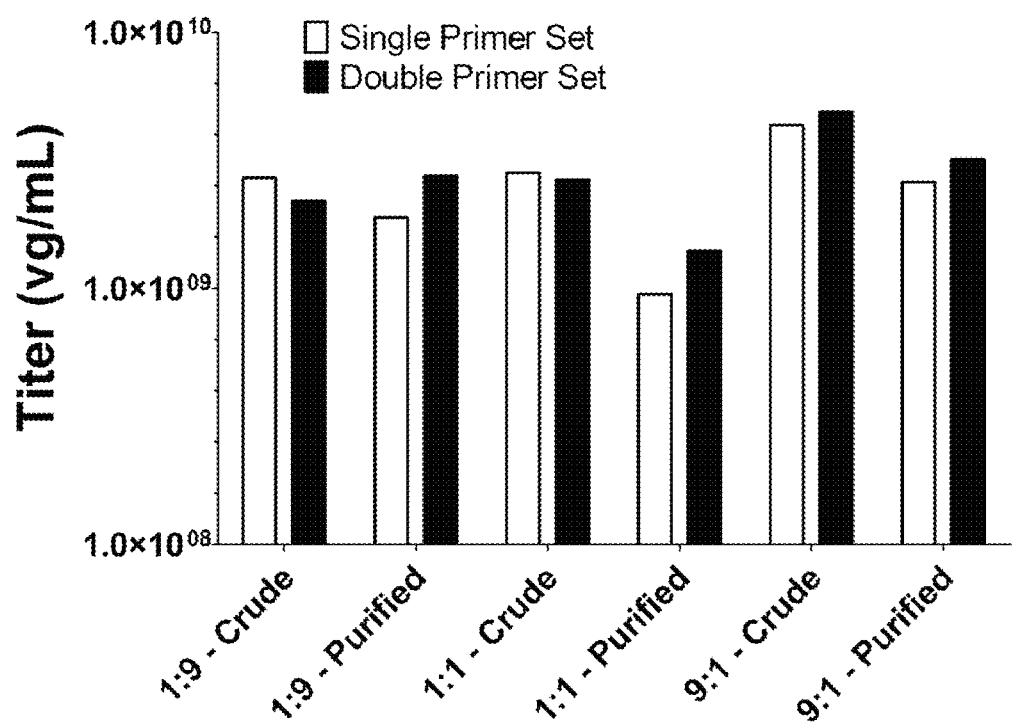
FIG. 2 is a graph showing total vector genomes resulting from co-packaging. DNA was extracted from post-benzonase treated crude lysates (Crude) or after iodixanol purification (Purified) of GFP and mCherry vectors co-packaged at 1:9, 1:1 or 9:1 ratios, respectively. Total vector genome titer was determined either directly, using a common CMV enhancer (Single Primer Set), or from the summation of each vector titer using transgene specific primers (Double Primer Set). Data represent the average total titer from crude (final volume of 3 mL) or purified samples (final volume of 0.2 mL) at each ratio assayed in triplicate.
Figure 3:
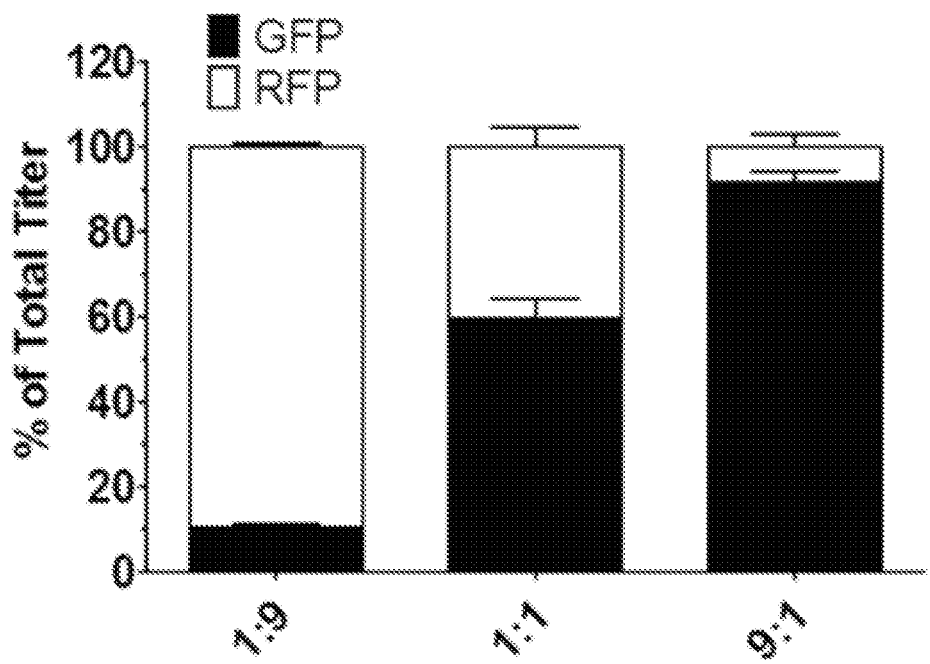
FIG. 3 is a graph showing that two expression cassettes can be packaged at predicted ratios combined prior to transfection. Quantitative PCR using transgene specific primers on iodixanol purified GFP or mCherry vectors was performed to determine the respective contribution of each individual vector in the total preparation when co-packaged at 1:9, 1:1 and 9:1 ratios, respectively. Each vector yield is expressed as a percentage of total vector genome, with 100% obtained from the summation of the titers determined using transgene specific primers for either GFP or mCherry. Data represent the average of three separate experiments for each ratio.

Each dual vector preparation was then subject to quantitative PCR (qPCR) analysis for a more robust quantification assessment. To determine the overall vector titer primers targeted towards the CMV enhancer region of the shared promoter to both AAV9-GFP and AAV9-mCherry were used (see "Methods—Titration of AAV Vectors"). At a scale of production using 150 mm tissue culture dishes, it was determined that an overall titer ranging from $\sim1\times10^9$ to $5\times10^9$ vg/mL in the crude lysate (volume 3 mL) and after iodixanol purification (volume 0.2 mL) (FIG. 2). The use of a single primer set or a combination of transgene specific primers simultaneously did not significantly affect the titration outcome (FIG. 2). In addition it was verified that the results obtained from purified vector preparations confirmed those obtained from crude lysates, which excluded potential risks of plasmid carry over or contamination from the transfection precipitate in benzonase-digested crude lysates. Titers determined from the transgene specific primers revealed that the predicted ratios of 1:9, 1:1 and 9:1 AAV9-GFP to AAV9-mCherry were recapitulated (FIG. 3). Corroborating what was observed using endpoint PCR, at the 1:9, 1:1 and 9:1 GFP to mCherry ratios, the mean percentage of their respective contribution to the total titer was: 11.03% to 88.97%, 64.12% to 35.88%, and 94.19% to 5.81% over the three independent packaging experiments. These data strongly support the hypothesis that AAV can package more than one expression plasmid combined at a predetermined ratio in a reproducible and predictable manner.

Ratios of Co Packaged Vectors are Maintained in In Vitro Cell Transduction

Figure 4:
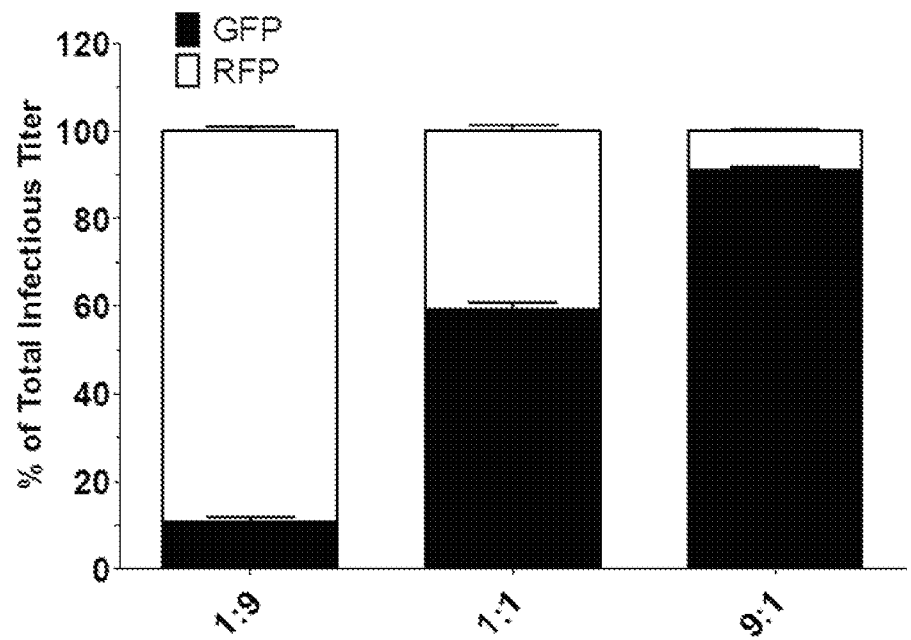
FIG. 4 is a graph showing in vitro characterization of co-packaged reporter vectors. The percent contribution of either AAV9-GFP or AAV9-mCherry to the total infectious titer (GFP+mCherry) was determined via single cell fluorescence assay in C12 cells. Data represent the average of two separate experiments for each ratio.

An established method of vector quality control is the infectivity or transduction assay. For marker gene carrying vectors, the assay is based on single cell fluorescence (Zolotukhin et al., 2002). To determine the infectious titer, C12 cells were transduced in the presence of Ad5 (MOI of 20), with purified AAV9-GFP and AAV9-mCherry co-packaged at the above ratios. Two days post-infection, green and red cells were visually counted independently. The infectious titer ranged from $8.5\times10^3$ to $1.25\times10^4$ IU/mL closely mirroring the vector genome titers. Furthermore the average particle-to-infectivity ratios ranged from $2.1\times10^5$ to $4.9\times10^5$, which were consistent with ratios observed for AAV9 preparations, and more importantly, the particle-to-infectivity ratios were not significantly different between the two marker constructs or at the different packaging ratios (data not shown). The mean respective contribution of green and red cells to the total infectious titer was: 10.85% to 89.15%, 59.34% to 40.66%, and 91.22% to 8.78% (FIG. 4). These results indicate that co-packaged vectors also display transduction profiles in the ratios at which they were co-packaged.

Therapeutic Constructs can be Differentially Packaged

It may prove efficacious in some instances to use multiple vectors that target transgene expression to specific tissues. Therefore this method was applied to the production of therapeutically relevant constructs differing in transcription elements. Vectors containing human codon-optimized acid α-glucosidase (coGAA) with different promoter elements that target expression to the liver [ApoE-HCR-hAAT promoter (LSP)] or cardiac, skeletal, and neuronal tissue [desmin promoter (DES)] were co-packaged and purified at the above ratios in AAV9 in 150 mm tissue culture dishes. Dual vector preparations were analyzed in a similar manner as the marker containing vectors. Titers were assessed using forward primers within the individual promoters (LSP or DES) and a shared, reverse primer anchored in the transgene (GAA; Table 2). Endpoint PCR confirmed the differential contribution of the two constructs to the total vector production (FIG. 5A). Resulting overall titers ranged from $1\times10^9$ to $3\times10^9$ vg/mL. Similarly, qPCR revealed the output ratio recapitulated the predicted ratios as was observed when AAV9-GFP and AAV9-mCherry were co-packaged (FIG. 5B). The mean percentage of the total titer consisting of AAV9-LSP-coGAA or AAV9-DES-coGAA was: 9.09% to 90.91%, 57.10% to 42.90%, and 93.83% to 6.17%. The data presented support the hypothesis that packaging predetermined ratios of input plasmid containing different transcriptional elements results in a heterogeneous population containing multiple vectors with the potential of expressing in discrete tissues. These results also indicate that production of multiple vectors in a single transfection step can produce dual, or potentially more, vectors at a predetermined ratio reproducibly and at the proportion of the investigator's choice.

Discussion

The widespread use of AAV for gene therapy applications emphasizes its utility and diverse capabilities but the limitations of manufacturing and packaging size have dampened the rapid successes observed in preclinical models to translation in the clinic. Many groups have investigated manners in which greater quantities of vector can be made quickly and efficiently with varying degrees of success. The most standard protocol to produce recombinant AAV, both at research and clinical grade, is a transfection method using two or sometimes three plasmids to provide all the cis and trans functions necessary to package AAV (Zolotukhin et al., 2002). However, transfection-based methods are inherently difficult to adapt to large scale platforms and methods using baculovirus (Kotin 2011; Mietzsch et al., 2014) or herpes simplex virus 1 (HSV) systems (Clément et al., 2009), together with producer cells grown in suspension, are rapidly improving and paving the way to future manufacturing campaigns. Despite these quick and impressive advancements toward infection-based methods, transfection remains the most versatile and cost effective method at small and medium scale preparations enabling researchers to develop proof-of-principle concepts.

Current methods of AAV production are directed towards the manufacturing of a single vector at a purity and titer conducive for preclinical studies or early phase clinical trials. In some instances, the use of more than one AAV may be beneficial or even required as a therapeutic approach. For some diseases, the production of multiple vectors containing fragmented genomes is required when the constructs exceed the carrying capacity of the vector. Duchenne's muscular dystrophy, hemophilia A, Tay-Sachs disease and Usher 1 are only a few of the diseases that would rely on multiple gene products or trans-splicing vectors to provide for therapeutic benefit (Mah et al., 2003; Cachón-González et al., 2012; Lopes et al., 2013; Koo et al., 2014; Lostal et al., 2014; Dyka et al., 2014). Similarly, it may prove necessary to coordinate and differentially control transgene expression to different target regions with tissue restricted promoters, such as the central nervous system, eye or systemically, while avoiding expression in antigen presenting cells and provoking a deleterious immune response (Zhang et al., 2012; Palfi et al., 2012; Fagoe et al., 2013). The benefit of altering the construct and not the capsid lies in that the coordination of expression may be contingent upon the tropism of a particular serotype and it has already been shown that much of the population is already seropositive for many of the serotypes in clinical trial (Boutin et al., 2010). It would behoove an investigator then to ensure that all cell and tissue types are transduced at a minimal degree of exposure of the animal or individual to multiple serotypes. This immunization against the various serotypes would preclude any subsequent attempts using different capsid variants without substantial immunomodulation as well as potentially prime innate and adaptive responses against viral components; all of which have been shown to be detrimental to long-term efficacy (Cresawn et al., 2005; Jayandharan et al., 2011; Wang et al., 2011; Sudres et al., 2012; Mingozzi and High 2013). Based on these considerations, the method described herein is being used to develop a single gene therapy product that will allow for the simultaneous induction of immune tolerance and physiologic correction of Pompe disease that may prove beneficial for other metabolic myopathies characterized by systemic pathology and are prone to immune responses to the therapeutic protein.

When more than one vector is necessary to the therapeutic approach, investigators have the sole choice of producing and testing each vector preparation independently, followed by co-administration of the two vectors at time of dosing. As an obvious consequence, processing times are often increased and cost doubled; aspects all the more relevant for clinical manufacturing. Clinical manufacturing and release testing of AAV in compliance with FDA-regulated Good-Manufacturing Practices (GMP) is extremely costly and time consuming, a non-trivial aspect of designing an AAV gene therapy trial. Furthermore, pre-clinical toxicology studies would need to integrate additional animals and controls to evaluate safety of each single vector separately, as well as in combination, and again, resulting in dramatic increases in cost and time toward protocol validation.

The necessity of novel production methods to provide for multiple constructs in an efficient and reliable manner currently stands as an unmet need in the field. This study focused on the development of such a method. Here it was revealed that vectors containing either different transgenes or transcriptional elements could be combined in predetermined ratios and produce an output of vector that recapitulated that prediction. Although a method for developing mosaic capsids by co-transfection has been previously attempted (Gigout et al., 2005), this study is the first instance of constructing a heterogeneous population of vectors containing different payloads in a single manufacturing step.

Here it was demonstrated that disparate ratios (1:9 or 9:1) provided for the greatest reliability in titration and infectivity, at least in vitro. In all cases the favored construct was the smaller of the two, emphasizing the care with which the plasmids should be combined when packaging taking into account the total size of the plasmid and maintaining precise molar ratios. Co-packaging may therefore provide as an alternative method of vector production where more than one gene product is necessary, and providing as a novel platform for treating diverse congenital disorders for which AAV mediated gene therapy is applicable. Moreover, this technique could theoretically expand to infection-based systems as the expression cassettes to be packaged could be provided at varying multiplicities of infection to produce a heterogeneous population of vectors similar to results here using transfection.

With respect to regulatory aspects of AAV clinical manufacturing, the main advantage of this strategy is related to being extremely cost and time effective, as developed earlier. The dual vector preparation should be considered as one single new investigational drug (IND) for each given ratio. This advantage may also be a challenge, as precise methods to characterize each vector contribution must be developed and well controlled, and reproducibility of the production method established. To facilitate FDA review and approval, the chosen dual vector at the therapeutic ratio, similar to a single AAV drug, will undergo extensive toxicology and dose assessment studies. The ratio must remain unchanged throughout the protocol validation, at least within the margin of errors of the methods used to produce and characterize the vector preparation. Identity testing, including whole genome sequencing, will be a challenge. However new next generation sequencers allow for Massive Parallel Sequencing (MSP) to provide full sequencing of multiple species in one given sample, which would also confirm the ratio of each vector construct. From this study, and for the constructs tested here, it is believed that with appropriate characterization tools, both vectors can be accurately titrated and that predicted ratios are consistent across several production attempts.

Example 2. Exemplary rAAV Co-Production Protocol

To date adeno-associated virus (AAV) has been used in 109 gene therapy clinical trials. The widespread tropism, sustained gene expression and excellent safety data that exist for AAV are only a few of the reasons it has reached such popularity. Among its drawbacks though are size limitation, with an optimal packaging size of ~4.7 kb, and the challenges to produce high titer vectors in a cost and time effective manner. Furthermore, some indications may require the use of two or more vector constructs. For instance, different promoters may be used to support specific tissue targeting. For long cDNA, the packaging capacity may be expanded by splitting the cDNA and using cis- or trans-splicing elements. Clinical applications using two or more AAV constructs would be time and cost prohibitive if each construct was produced separately. To facilitate the use and production of multiple vectors, a novel production method was explored that exploited the stoichiometric properties of the virus in that only one expression plasmid is packaged per encapsidated virus. The tested hypothesis was that combining plasmids prior to packaging at a known input ratio would result in an output vector preparation containing the equivalent ratio.

Methods

AA V9 Vector Production and Purification

AAV vectors were produced in 150 mm tissue culture dishes via CaPO4 transfection GFP+mCherry and LSP+DES vectors were co-packaged at 1:9, 1:1, and 9:1 ratios The amount of expression plasmid for co-packaging was determined by the total amount of DNA necessary and the total base pair size of the individual constructs to retain equimolar ratios. Post-benzonase treated, vector-containing supernatant was used for quantitative PCR (qPCR) or further purified using discontinuous iodixanol step gradients for qPCR and infectivity assays.

Titration of Vectors

Primers were designed for the shared CMV enhancer of the GFP and mCherry vectors as well as unique fragments within the transgenes. The LSP and DES vectors were titrated using unique forward primers within the promoter and a shared reverse primer anchored within the transgene. Standard curves were generated by using $10^{10}$-$10^5$ total copies of the relevant expression plasmids either singly or in combination with a non-template control. QPCR was performed with iTaq™ Universal SYBR® Green Supermix on a BIO-RAD™ CFX96™ Real-Time PCR Detection System and analyzed using BIO-RAD™ CFX MANAGER™ v. 3.1.

Single Cell Fluorescence Assay

C12 cells were seeded at $2 \times 10^4$ cells in a 96-well plate and infected 18 hours later with the co-packaged vectors in a 10-fold dilution series in the presence of Ad5 (MOI 20). 40 hours later, red and green cells were counted using a fluorescent microscope and the infectious titer was calculated based on dilution.

Results

Figure 6:
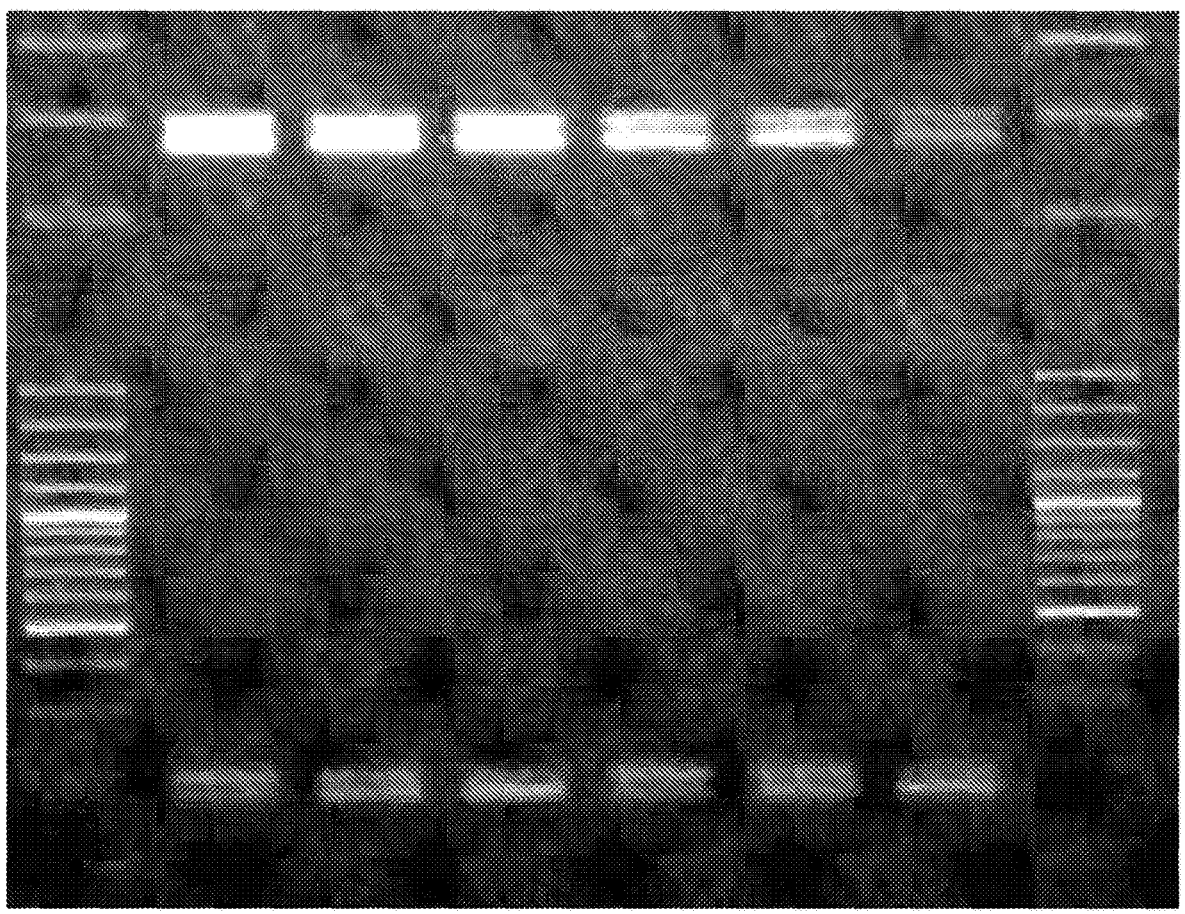
FIG. 6 is a photograph of a DNA gel showing vectors co-packaged at ratios 1:9 GFP to mCherry, 1:1, and 9:1. Top: Standard of $10^{10}$ to $10^5$ total copies of the combined constructs. GFP band is 171 bp and mCherry is 191 bp. Bottom: Lanes 1-3 contain DNA amplified from vectors in crude lysate (post-benzonase treatment); lanes 4-6 contain DNA amplified from vectors purified via iodixanol gradient.

As shown in FIG. 6, vectors were co-packaged at ratios 1:9 GFP to mCherry, 1:1, and 9:1. The differential packaging of the vectors was evident. The use of multiple primer sets and different sources of vector DNA had no effect on PCR efficiency.

As shown in FIG. 2 and FIG. 3, the titer of co-packaged GFP and mCherry (RFP) vectors using a single primer set targeting a shared CMV enhancer compared to the sum of titers determined from transgene specific primers used simultaneously showed no significant difference. Additionally, titers determined from crude lysate or iodixanol purified vector did not impact total quantification. QPCR titration determined from the transgene specific primers revealed that the respective contribution of each vector to the total titer corroborated the predicted ratios of GFP to mCherry prior to transfection.

As shown in FIG. 4, as a measure of infectivity, a single cell fluorescence assay was performed on C12 cells. The individual contribution of each vector to the total infectious titer also repeated the predicted ratios.

Figure 5:
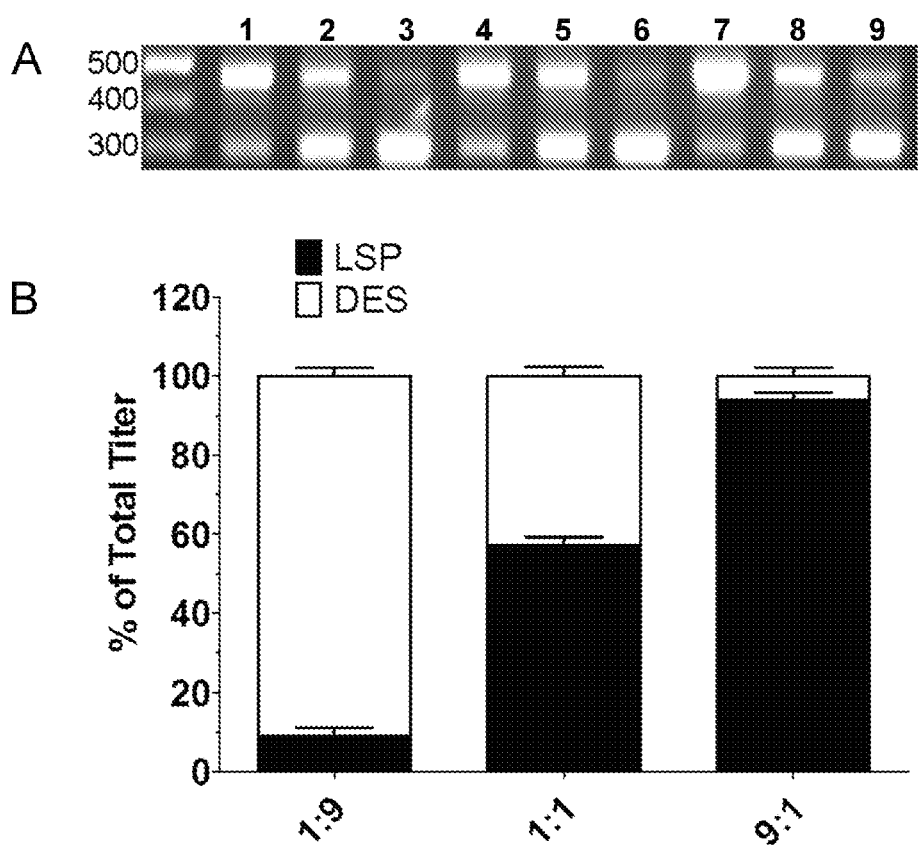
FIGS. 5A and B are a photograph and a graph showing co-packaging of therapeutic constructs.
FIG. 5B) DNA extracted from co-packaged AAV9-LSP-coGAA and AAV9-DES-coGAA was subjected to quantitative PCR to determine the respective contribution of each individual vector in the total preparation when co-packaged at 1:9, 1:1 and 9:1 ratios, respectively. Each vector yield is expressed as a percentage of total vector genome, with 100% obtained from the summation of the titers determined using promoter specific primers for either LSP or DES. Data represent the average of three separate experiments for each ratio. LSP, liver specific promoter; DES, desmin promoter; coGAA, human codon-optimized acid α-glucosidase.

As shown in FIG. 5, therapeutic constructs differing in promoter elements (liver specific promoter—LSP; desmin promoter—DES) driving human codon-optimized acid α-glucosidase were co-packaged at 1:9, 1:1, and 9:1 ratios. The observed percent contribution of each vector to the total titer validated the predicted ratios.

CONCLUSION

During transfection, AAV will co-package reporter constructs combined at a predetermined ratio predictably and reproducibly to generate a heterogeneous population of vectors. Co-packaged vectors transduce C12 cells in the predicted ratios. Therapeutic constructs differing in promoter elements were also co-packaged in a reliable method. At least two constructs, differing in either transgene or transcription elements, can be efficiently co-packaged and return vector in equivalent ratios.

REFERENCES

Aschauer, D. F., Kreuz, S., Rumpel, S. (2013). Analysis of transduction efficiency, tropism and axonal transport of AAV serotypes 1, 2, 5, 6, 8 and 9 in the mouse brain. PLoS One 8, e76310.

Asokan, A., Samulski, R. J. (2013). An emerging adeno-associated viral vector pipeline for cardiac gene therapy. Hum. Gene Ther. 24, 906-913.

Asokan, A., Schaffer, D. V., Samulski, R. J. (2012). The AAV vector toolkit: poised at the clinical crossroads. Mol. Ther. 20, 699-708.

Boutin, S., Monteilhet, V., Veron, P, et al. (2010). Prevalence of serum IgG and neutralizing factors against adeno-associated virus (AAV) types 1, 2, 5, 6, 8, and 9 in the healthy population: implications for gene therapy using AAV vectors. Hum. Gene Ther. 21, 704-712.

Cachón-González, M. B., Wang, S. Z., McNair, R., et al. (2012). Gene transfer corrects acute GM2 gangliosidosis—potential therapeutic contribution of perivascular enzyme flow. Mol. Ther. 20, 1489-500.

Cao, O., Dobrzynski, E., Wang, L, et al. (2007). Induction and role of regulatory CD4+CD25+ T cells in tolerance to the transgene product following hepatic in vivo gene transfer. Blood 110, 1132-1140.

Clément, N., Knop, D. R., Byrne, B. J. (2009). Large-scale adeno-associated viral vector production using a herpesvirus-based system enables manufacturing for clinical studies. Hum. Gene Ther. 20, 796-806.

Cresawn, K. O., Fraites, T. J., Wasserfall, C., et al. (2005). Impact of humoral immune response on distribution and efficacy of recombinant adeno-associated virus-derived acid alpha-glucosidase in a model of glycogen storage disease type II. Hum. Gene Ther. 16, 68-80.

Dong, J. Y., Fan, P. D., Frizzell, R. A. (1996). Quantitative analysis of the packaging capacity of recombinant adeno-associated virus. Hum. Gene Ther. 7, 2101-2112.

Doria, M., Ferrara, A., Auricchio, A. (2013). AAV2/8 vectors purified from culture medium with a simple and rapid protocol transduce murine liver, muscle, and retina efficiently. Hum. Gene Ther. Methods 24, 392-398.

Dyka, F. M., Boye, S. L., Chiodo, V. A., et al. (2014). Dual adeno-associated virus vectors result in efficient in vitro and in vivo expression of an oversized gene, MYO7A. Hum. Gene Ther. Methods 25, 166-177.

Fagoe, N. D., Eggers, R., Verhaagen, J., Mason, M. R. (2013). A compact dual promoter adeno-associated viral vector for efficient delivery of two genes to dorsal root ganglion neurons. Gene Ther. 21, 242-252.

Falk, D. J., Mah, C. S., Soustek, M. S., et al. (2013). Intrapleural administration of AAV9 improves neural and cardiorespiratory function in Pompe disease. Mol. Ther. 21, 1661-1667.

Faust, S. M., Bell, P., Cutler, B. J., et al. (2013). CpG-depleted adeno-associated virus vectors evade immune detection. J. Clin. Invest. 123, 2994-3001.

Ghosh, A., Yue, Y., Duan, D. (2011). Efficient transgene reconstitution with hybrid dual AAV vectors carrying the minimized bridging sequences. Hum. Gene Ther. 22, 77-83.

Gigout, L., Rebollo, P., Clement, N. et al. (2005). Altering AAV tropism with mosaic viral capsids. Mol. Ther. 11, 856-865.

Gurda, B. L., Raupp, C., Popa-Wagner, R., et al. (2012). Mapping a neutralizing epitope onto the capsid of adeno-associated virus serotype 8. J. Virol. 86, 7739-7751.

Hirsch, M. L., Li, C., Bellon, I., et al. (2013). Oversized AAV transduction is mediated via a DNA-PKcs-independent, Rad51C-dependent repair pathway. Mol. Ther. 21, 2205-2216.

Jayandharan, G. R., Aslanidi, G., Martino, A. T., et al. (2011.) Activation of the NF-kappaB pathway by adeno-associated virus (AAV) vectors and its implications in immune response and gene therapy. Proc. Natl. Acad. Sci. USA 108, 3743-3748.

Koo, T., Popplewell, L., Athanasopoulos, T., Dickson, G. (2014). Triple trans-splicing adeno-associated virus vectors capable of transferring the coding sequence for full-length dystrophin protein into dystrophic mice. Hum. Gene Ther. 25, 98-108.

Kotin, R. M. (2011). Large-scale recombinant adeno-associated virus production. Hum. Mol. Genet. 20, R2-6.

Lai, Y., Yue, Y., Liu, M., et al. (2005). Efficient in vivo gene expression by trans-splicing adeno-associated viral vectors. Nat. Biotechnol. 23, 1435-1439.

Lopes, V. S., Boye, S. E., Louie, C. M., et al. (2013). Retinal gene therapy with a large MYO7A cDNA using adeno-associated virus. Gene Ther. 20, 824-833.

Lostal, W., Kodippili, K., Yue, Y., Duan, D. (2014). Full-length dystrophin reconstitution with adeno-associated viral vectors. Hum. Gene Ther. 25, 1-11.

Mah, C., Sarkar, R., Zolotukhin, I., et al. (2003). Dual vectors expressing murine factor VIII result in sustained correction of hemophilia A mice. Hum. Gene Ther. 14, 143-152.

Mah, C. S., Soustek, M. S., Todd, A. G., et al. (2013). Adeno-associated virus-mediated gene therapy for metabolic myopathy. Hum. Gene Ther. 24, 928-936.

Manno, C. S., Pierce, G. F., Arruda, V. R., et al. (2006). Successful transduction of liver in hemophilia by AAV-Factor IX and limitations imposed by the host immune response. Nat. Med. 12, 342-347.

Markusic, D. M., Herzog, R. W. (2012). Liver-directed adeno-associated viral gene therapy for hemophilia. J. Genet. Syndr. Gene Ther. 1, 1-9.

Miao, C. H., Ohashi, K., Patijn, G. A., et al. (2000). Inclusion of the hepatic locus control region, an intron, and untranslated region increases and stabilizes hepatic factor IX gene expression in vivo but not in vitro. Mol. Ther. 1, 522-532.

Mietzsch, M., Grasse, S., Zurawski, C., et al. (2014). One-Bac: Platform for scalable and high-titer production of adeno-associated virus serotype 1-12 vectors for gene therapy. Hum. Gene Ther. 25, 212-222.

Mingozzi, F., High, K. A. (2013). Immune responses to AAV vectors: overcoming barriers to successful gene therapy. Blood 122, 23-36.

Pacak, C. A., Sakai, Y., Thattaliyath, B. D., et al. (2009). Tissue specific promoters improve specificity of AAV9 mediated transgene expression following intra-vascular gene delivery in neonatal mice. Genet. Vaccines Ther. 6, 13.

Palfi, A., Chadderton, N., McKee, A. G., et al. (2012). Efficacy of codelivery of dual AAV2/5 vectors in the murine retina and hippocampus. Hum. Gene Ther. 23, 847-858.

Pulicherla, N., Shen, S., Yadav, S., et al. (2011). Engineering liver-detargeted AAV9 vectors for cardiac and musculoskeletal gene transfer. Mol. Ther. 19, 1070-1078.

Rabinowitz, J. E., Rolling, F., Li, C., et al. (2002). Cross-packaging of a single adeno-associated virus (AAV) type 2 vector genome into multiple AAV serotypes enables transduction with broad specificity. J. Virol. 76, 791-801.

Rayaprolu, V., Kruse, S., Kant, R., et al. (2013). Comparative analysis of adeno-associated virus capsid stability and dynamics. J. Virol. 87, 13150-13160.

Rogers, G. L., Martino, A. T., Aslanidi, G. V., et al. (2011). Innate immune responses to AAV vectors. Front. Microbiol. 2, 194.

Sudres, M., Ciré, S., Vasseur, V., et al. (2012). MyD88 signaling in B cells regulates the production of Th1-dependent antibodies to AAV. Mol. Ther. 20, 1571-1581.

Wang, L., Calcedo, R., Bell, P., et al. (2011). Impact of pre-existing immunity on gene transfer to nonhuman primate liver with adeno-associated virus 8 vectors. Hum. Gene Ther. 22, 1389-1401.

Zhang, P., Sun, B., Osada, T., et al. (2012). Immunodominant liver-specific expression suppresses transgene-directed immune responses in murine pompe disease. Hum. Gene Ther. 23, 460-472.

Zhang, Y., Duan, D. (2012). Novel mini-dystrophin gene dual adeno-associated virus vectors restore neuronal nitric oxide synthase expression at the sarcolemma. Hum. Gene Ther. 23, 98-103.

Zhang, Y., Yue, Y., Li, L., et al. (2013). Dual AAV therapy ameliorates exercise-induced muscle injury and functional ischemia in murine models of Duchenne muscular dystrophy. Hum. Mol. Genet. 22, 3720-3729.

Zincarelli, C., Soltys, S., Rengo, G., Rabinowitz, J. E. (2008). Analysis of AAV serotypes 1-9 mediated gene expression and tropism in mice after systemic injection. Mol. Ther. 16, 1073-1080.

Zolotukhin, S., Potter, M., Hauswirth, W. W., et al. (1996). A "humanized" green fluorescent protein cDNA adapted for high-level expression in mammalian cells. J. Virol. 70, 4646-4654.

Zolotukhin, S., Potter, M., Zolotukhin, I., et al. (2002). Production and purification of serotype 1, 2, and 5 recombinant adeno-associated viral vectors. Methods 28, 158-167.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of producing a recombinant adeno-associated virus (rAAV) particle preparation having a target ratio of a first rAAV particle to a second rAAV particle, the method comprising:
   (a) contacting a producer cell preparation with:
      (i) a first nucleic acid vector containing a first construct comprising a heterologous nucleic acid region encoding a first protein or polypeptide and nucleic acid regions comprising an inverted terminal repeat (ITR) flanking each side of the heterologous nucleic acid region;
      (ii) a second nucleic acid vector containing a second construct comprising a heterologous nucleic acid region encoding a second protein or polypeptide and nucleic acid regions comprising an inverted terminal repeat (ITR) flanking each side of the heterologous nucleic acid region; and
      iii) one or more helper nucleic acids,
      wherein the producer cell preparation is contacted under conditions sufficient for producing a heterogeneous mixture of rAAV particles comprising a first rAAV particle comprising the first construct and a second rAAV particle comprising the second construct and
   (b) isolating the heterogeneous mixture of rAAV particles from the producer cell preparation, thereby producing a heterogeneous rAAV preparation having a target ratio of the first rAAV particle to the second rAAV particle, wherein the target ratio of the first rAAV particle to the second rAAV particle is within 10% of the initial ratio of the first nucleic acid vector to the second nucleic acid vector when contacted with the cell preparation.

2. The method of claim 1, wherein the cell preparation is contacted simultaneously with the first nucleic acid vector and the second nucleic acid vector.

3. The method of claim 1, wherein the initial ratio is 1:1, 1:9 or 9:1 of the first nucleic acid vector to the second nucleic acid vector.

4. The method of claim 1, wherein the target ratio of the first rAAV particle to the second rAAV particle is measured after isolating the first rAAV particle and the second rAAV particle from the cell preparation.

5. The method of claim 4, wherein the target ratio of the first rAAV particle to the second rAAV particle is measured by measuring a level of DNA from the first rAAV particle and a level of DNA from the second rAAV particle.

6. The method of claim 5, wherein the level of DNA is measured using PCR, sequencing or flow cytometry.

7. The method of claim 1, wherein step (a) comprises transfecting the cell preparation with the first nucleic acid vector and the second nucleic acid vector.

8. The method of claim 1, wherein the first nucleic acid vector and the second nucleic acid vector are a first plasmid and a second plasmid.

9. The method of claim 8, wherein the one or more helper nucleic acids comprise at least one helper plasmid.

10. The method of claim 9, wherein the at least one helper plasmid is a first helper plasmid comprising a rep gene and a cap gene and a second helper plasmid comprising a E1a gene, a E1b gene, a E4 gene, a E2a gene, and a VA gene.

11. The method of claim 1, wherein step (a) comprises infecting the cell preparation with the first nucleic acid vector and the second nucleic acid vector.

12. The method of claim 11, wherein the first nucleic acid vector is contained within a first herpes simplex virus type 1 (HSV) particle and the second nucleic acid vector is contained within a second HSV particle.

13. The method of claim 11, wherein the first nucleic acid vector is contained within a first baculovirus particle and the second nucleic acid vector is contained within a second baculovirus particle.

14. The method of claim 1, wherein step (a) comprises incubating the cell preparation for at least 60 hours after contacting the cell preparation with the first nucleic acid vector and the second nucleic acid vector.

15. The method of claim 1, wherein step (b) comprises lysing the cell preparation and extracting the first rAAV particle and the second rAAV particle.

16. The method of claim 15, wherein the first rAAV particle and the second rAAV particle are extracted simultaneously.

17. The method of claim 1, wherein the first rAAV particle and the second rAAV particle are each rAAV 2/9 pseudotyped particles.

18. The method of claim 1, wherein the initial ratio is 1:10, 10:1, 1:8 or 8:1 of the first nucleic acid vector to the second nucleic acid vector.

19. The method of claim 1, wherein the target ratio of the first rAAV particle to the second rAAV particle is within 5% of the initial ratio of the first nucleic acid vector to the second nucleic acid vector.

* * * * *